United States Patent
Barden et al.

(10) Patent No.: US 9,428,587 B2
(45) Date of Patent: Aug. 30, 2016

(54) ANTIBODIES TO NON-FUNCTIONAL OLIGOMERIC P2X7 RECEPTORS AND METHODS OF USE THEREOF

(71) Applicant: Biosceptre International Limited, North Ryde, NSW (AU)

(72) Inventors: Julian Alexander Barden, North Ryde (AU); Angus Gidley-Baird, North Ryde (AU); Glenn Ronald Pilkington, North Ryde (AU)

(73) Assignee: BIOSCEPTRE INTERNATIONAL LIMITED (AU)

( * ) Notice: Subject to any disclaimer, the term of this patent is extended or adjusted under 35 U.S.C. 154(b) by 0 days.

(21) Appl. No.: 14/456,898

(22) Filed: Aug. 11, 2014

(65) Prior Publication Data

US 2015/0218283 A1 Aug. 6, 2015

Related U.S. Application Data

(63) Continuation of application No. 13/518,382, filed as application No. PCT/AU2010/001741 on Dec. 23, 2010, now Pat. No. 8,835,609.

(30) Foreign Application Priority Data

Dec. 24, 2009 (AU) ................................ 2009906286

(51) Int. Cl.
  *C07K 16/30* (2006.01)
  *C07K 16/28* (2006.01)
  *A61K 39/00* (2006.01)
  *G01N 33/574* (2006.01)
  *A61K 39/395* (2006.01)

(52) U.S. Cl.
  CPC .............. *C07K 16/30* (2013.01); *A61K 39/395* (2013.01); *C07K 16/2869* (2013.01); *G01N 33/57484* (2013.01); *A61K 39/00* (2013.01); *A61K 2039/505* (2013.01); *C07K 2317/34* (2013.01); *C07K 2317/52* (2013.01); *C07K 2317/55* (2013.01); *C07K 2317/565* (2013.01); *C07K 2317/622* (2013.01); *C07K 2317/73* (2013.01); *C07K 2317/76* (2013.01); *C07K 2317/92* (2013.01); *C07K 2319/00* (2013.01)

(58) Field of Classification Search
  CPC .............. C07K 16/2869; C07K 16/30; G01N 33/57484; A61K 39/00; A61K 39/395
  See application file for complete search history.

(56) References Cited

U.S. PATENT DOCUMENTS

| | | | |
|---|---|---|---|
| 6,133,434 A | 10/2000 | Buell et al. | |
| 6,303,338 B1 | 10/2001 | Ni et al. | |
| 6,306,393 B1 | 10/2001 | Goldenberg et al. | |
| 6,329,503 B1 | 12/2001 | Afar et al. | |
| 6,709,832 B1 | 3/2004 | Von Knebel Doeberitz | |
| 7,183,064 B1 | 2/2007 | Slater et al. | |
| 7,326,415 B2 | 2/2008 | Barden et al. | |
| 7,531,171 B2 | 5/2009 | Barden et al. | |
| 7,767,789 B2 | 8/2010 | Gorodeski et al. | |
| 7,888,473 B2 | 2/2011 | Barden et al. | |
| 8,067,550 B2 | 11/2011 | Barden et al. | |
| 8,080,635 B2 | 12/2011 | Barden et al. | |
| 8,293,491 B2 | 10/2012 | Gidley-Baird et al. | |
| 8,399,617 B2 | 3/2013 | Barden et al. | |
| 8,440,186 B2 | 5/2013 | Barden et al. | |
| 8,597,643 B2 | 12/2013 | Barden et al. | |
| 8,658,385 B2 | 2/2014 | Gidley-Baird et al. | |
| 8,709,425 B2 | 4/2014 | Barden et al. | |
| 8,835,609 B2 | 9/2014 | Barden et al. | |
| 2004/0067542 A1 | 4/2004 | Barden et al. | |
| 2007/0020706 A1 | 1/2007 | Gorodeski et al. | |
| 2007/0248963 A1 | 10/2007 | Slater et al. | |
| 2008/0131438 A1 | 6/2008 | Barden et al. | |
| 2008/0227122 A1 | 9/2008 | Barden et al. | |
| 2009/0215727 A1 | 8/2009 | Douglas | |
| 2010/0036101 A1 | 2/2010 | Gidley-Baird et al. | |
| 2011/0111431 A1 | 5/2011 | Slater et al. | |
| 2012/0282278 A1 | 11/2012 | Barden et al. | |
| 2013/0266592 A1 | 10/2013 | Barden et al. | |
| 2013/0273085 A1 | 10/2013 | Barden et al. | |
| 2014/0135475 A1 | 5/2014 | Barden et al. | |
| 2014/0323693 A1 | 10/2014 | Barden et al. | |
| 2015/0004179 A1 | 1/2015 | Barden et al. | |

FOREIGN PATENT DOCUMENTS

| | | |
|---|---|---|
| AU | 64184/98 B2 | 10/1998 |
| CA | 2284859 C | 1/2007 |
| EP | 1006186 A1 | 10/1998 |
| WO | WO 92/16558 A1 | 10/1992 |
| WO | WO 95/33048 A2 | 12/1995 |
| WO | WO 97/06256 A2 | 2/1997 |
| WO | WO 97/41222 A1 | 11/1997 |
| WO | WO 98/42835 A1 | 10/1998 |
| WO | WO 00/50458 A1 | 8/2000 |
| WO | WO 01/06259 A1 | 1/2001 |
| WO | WO 01/30964 A2 | 5/2001 |
| WO | WO 02/48395 A1 | 6/2002 |
| WO | WO 02/057306 A1 | 7/2002 |

(Continued)

OTHER PUBLICATIONS

U.S. Appl. No. 60/686,770, filed Jun. 2, 2005, Gorodeski et al.

(Continued)

*Primary Examiner* — Robert Landsman
(74) *Attorney, Agent, or Firm* — Alston & Bird LLP

(57) ABSTRACT

The invention relates to purinergic receptors, to antibodies and related fragments thereof for binding to said receptors, to production of said antibodies and fragments and to sue of said antibodies and fragments for cancer detection and therapy. In particular the antibodies described bind specifically to non-functional P2X& receptors expressed by live cells.

13 Claims, 32 Drawing Sheets

(56) References Cited

FOREIGN PATENT DOCUMENTS

| | | |
|---|---|---|
| WO | WO 03/020762 A1 | 3/2003 |
| WO | WO 2004/092384 A2 | 10/2004 |
| WO | WO 2008/043145 A2 | 4/2008 |
| WO | WO 2008/043145 A1 | 4/2008 |
| WO | WO 2009/033233 A1 | 3/2009 |
| WO | WO 2009/033234 A1 | 3/2009 |
| WO | WO 2010/000041 A1 | 7/2010 |
| WO | WO 2011/020155 A1 | 2/2011 |
| WO | WO 2011/075789 A1 | 6/2011 |
| WO | WO 2011/131472 A1 | 10/2011 |
| WO | WO 2012/031333 A1 | 3/2012 |
| WO | WO 2013/003895 A1 | 1/2013 |
| WO | WO 2007/027957 A2 | 11/2014 |

OTHER PUBLICATIONS

U.S. Appl. No. 60/778,993, filed Mar. 3, 2006, Gorodeski et al.
Ayyanathan et al., "Cloning and chromosomal localisation of the human P2Y1 purinoceptor," Biochem Biophys Res Commun, 218(3):783-788, (1996).
Barden et al., "Specific detection of non-functional human P2X7 receptos in HEK293 cells and B-lymphocytes," FEBS Letters, 538:159-162, (2003).
Bird et al., "Single-Chain Antigen-Binding Proteins," Science, 242(4877):423-426, (1988).
Bowler et al., "Identification and cloning of human P2U purinoceptor present in osteoclastoma, bone, and osteoblasts," J Bone Min Res, 10(7):1137-1145, (1995).
Buell et al., "P2X receptors: am emerging channel family," Eur J Neurosci., 8:2221-2228, (1996).
Buell et al., "Blockade of Human P2X7 Receptor Function With a Monoclonal Antibody," Blood, 92:3521-3528, (1998).
Burnstock et al., "P2 Purinergic Receptors: Modulation of Cell Function and Therapeutic Potential," J Pharm Exp Therap, 295:862-869, (2000).
Casset et al., "A peptide mimetic of an anti-CD4 monoclonal antibody by rational design," Biochemical and Biophysical Research Communications, 307:198-205, (2003).
Chan et al., "Localization of P2X1 purinoceptors by autoradiography and immunohistochemistry in rat kidneys," Am J Physiol Renal Physiol, 274(4(2)): F799-804, (1998).
Cheewatrakoolpong et al., "Identification and charaterization of splice variants of the human P2X7 ATP channel," Biochem Biophys Res Comm., 332:17-27, (2005).
Chessell et al., "Dynamics of P2X7 receptor pore dilation: pharmacological and functional consequences," Drug Dev Res, 53(2-3):60-65, (2001).
Colman, "Effects of amino acid sequence changes on antibody-antigen interactions," Research in Immunology, A Structural View of Immune Recongnition by Antibodies, 55th Forum in Immunology, 145:33-36, (1994).
Communi et al., "Cloning and Functional Expression of a Human Uridine Nucleotide Receptor," J Biol Chem, 270(52): 30849-30852, (1995).
Communi et al., "Cloning, Functional Expression and Tissue Distribution of the Human P2Y6 Receptor," Biochem Biophys Res Commun, 222:303-308, (1996).
Dangl et al., "Rapid Isolation of Cloned Isotype Switch Variants Using Fluorescence Activated Cell Sorting," Cytometry, 2:395-401, (1982).
DeRisi et al., "Exploring the Metabolic and Genetic Control of Gene Expression on a Genomic Scale," Science, 278: 680-686, (1997).
Di Virgilio et al., "Responses of mouse lymphocytes to extracellular adenosine 5'triphosphaste (ATP)," J Immunol 143:1955-1960, (1989).
Di Virgiolio et al., "Purinergic P2X7 receptor: a pivotal role in inflammation and immunomodulation," Drug Dev Res, 45:207-213, (1998).

Dixon et al, "Extracellular nucleotides stimulate proliferation in MCF-7 breast cancer cells via P2-purinoceptors," Br J Cancer, 75(1):34-39, (1997).
Dubyak et al., "Signal transduction via P2-purinergic receptors for extracellular ATP and other nucleotides," Am. J Physiol 265:C577-C606,(1993).
European Search Report of Sep. 18, 2008 for application EP08156593 (published as EP1961767).
Feng et al, "A truncated P2X7 receptor variant (P2X7-j) endogenously expressed in cervical cancer cells antagonizes the full-length P2X7 receptor through hetero-oligomerization," J Biol Chem, 281:17228-17237, (2006).
Feng et al, "ATP stimulates GRK-3 phosphoryation and 3-arrestin-2-dependent inernalizaton of P2X7 receptor," Am J Physiol Cell Physiol, 288:C1342-C1356, (2005).
Ferrari et al., "P2Z purinoreceptor ligation induces activation of caspases with distinct roles in apoptotic and necrotic alterations of cell death," FEBS Lett., 447:71-75, (1999).
Ferrari et al., "ATP-mediated cytoxicity in microglial cells," Neuropharmacology, 36 (9):1295-1301, (1997).
Foster et al., "Cellular and molecular pathology of prostate cancer precursors," Scand J Urol Nephrol Suppl.,34(205):19-43, (2000).
Galfre et al., "Antibodies to major histocompatability antigens produced by hybrid cell lines," Nature, 266:550-552, (1977).
Galfre et al., "Rat x rat hybrid myelomas and a monoclonal anti-Fd portion of mouse IgG," Nature, 277:131-133, (1979).
Gefter et al., "A simple method for polyethylene glycol-promoted hybridization of mouse myeloma cells," Somatic Cell Genet., 3(2):231, (1977).
GenBank: Accession No. Y09561, versions Y09561.1, "*H. sapiens* mRNA for P2X7 receptor". [Retrieved from the Internet May 24, 2011 : <URL:http://www.ncbi.nlm.nih.gov/nuccore/y09561 >].
Georgiou et al., "Human Epidermal and Monocyte-Derived Langerhans Cells Express Functional P2X7 Receptors," J Invest Dermatology,125:482-490, (2005).
Giusti et al., "Somatic diversification of S107 from an antiphosphocholine to an anti-DNA autoantibody is due to a single base change in its heavy chain variable region," PNAS, 84:2926-2930, (1987).
Greenbaum et al., "Comparing protein abundance and mRNA expression levels on a genomic scale," Genome Biology, 4(9):117. 1-117.8, (2003).
Greig et al., "Expression of Purinergic Receptors in Non-melanoma Skin Cancers and Their Functional Roles in A431 Cells," J Invest Dermatol, 121:315-327, (2003).
Groschel-Stewart et al., "Localisation of P2X5 and P2X7 receptors by immunohistochemistry in rat stratified squamous epithelia," Cell Tissue Res, 296:599-605, (1999).
Gu et al, "A Glu-496 to Ala Polymorphism leads to loss of function of the human P2X7 receptor," J Biol Chem, 276(14):11135-11142, (2001).
Gu et al., "An Arg307 to Gin Polymorphism within the ATP-binding Site Causes Loss of Function of the Human P2X7 Receptor," J Biol Chem, 279 (30):31287-31295, (2004).
Gu et al., "Expression of P2X7 purinoceptors on human lymphocytes and monocytes: evidence for nonfunctional P2X 7 receptors," Am J Physiol Cell Physiol, 279:C1189-C1197, (2000).
Gussow et al., "Humanization of Monoclonal Antibodies," Methods in Enzymology, 203:99-121, (1991).
Hansen et al., "Structural Motif and Characteristics of the Extracellular Domain of P2X Receptors," Biochem and Biophys Res Comm, 236(3):670-675, (1997).
Hansen et al., "The distribution of single P (2×1)—receptor clusters on smooth muscle cells in relation to nerve varicosities in the rat urinary bladder," J Neurocytol, 27(7): 529-539, (1998).
Holliger et al., "Diabodies': Small bivalent and bispecific antibody fragments," Proc. Natl. Acad. Sci. USA, 90:6444-6448, (1993).
Hopfner et al, "Expression of functional P2-purinergic receptors in primary cultures of human colorectal carcinoma cells," Biochem and Biophys Res Comm, 251:811-817, (1998).
Humphrey, "Gleason grading and prognostic factors in carcinoma of the prostate," Modern Pathology, 17:292-306, (2004).

(56) References Cited

OTHER PUBLICATIONS

Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883, (1988).
Jacob et al., "Cytogenetic Profile of Chronic Myeloid Leukemias," Indian J Cancer, 39(2):61-65, (2002).
Jameison et al., "Extracellular ATP causes loss of L-selectin from human lymphocytes via occupancy of P2Z purinoceptors," J Cell Physiol, 166:637-642 (1996).
Janssens et al., "Effects of extracellular nucleotides and nucleosides on prostate carcinoma cells," Br J Pharmacol., 132: 536-46, (2001).
Jantzen et al., "Evidence for Two Distict G-proteion-coupled ADP Receptors Mediating Platelet Activation," Thromb and Haemost, 81:111-117, (1999).
Jones, "Critically assessing the state-of-the-art in protein structure prediction,"Pharmacogenomics Journal, 1:126-134, (2001).
Katzur et al., "Expression and responsiveness of P2Y2 receptors in human endometrial cancer cell lines," J Clin Endocrinol Metab., 84(11): 4085-4091, (1999).
Kennedy et al., "The discovery and development of P2 receptor subtypes," J Auto Nerv Syst, 81:158-163, (2000).
Kim et al., "Differential Assembly of Rat Purinergic P2X7 Receptor in Immune Cells of the Brain and Periphery," J Biol Chem, 276(26):23262-23267, (2001).
King et al., "Metabotropic receptors for ATP and UTP: exploring the correspondence between native and recombinant nucleotide receptors," TIPS, 19: 506-514, (1998).
Kishore et al., "Cellular localisation of P2Y2 purinoceptor in rat renal inner medulla and lung," Am J Physiol Renal Physiol, 278: F43-F51, (2000).
La Sala et al., "Alerting and tuning the immune response by extracellular Nucleotides," J Leukoc Biol, 73:339-343, (2003).
Lee et al., "P2X receptor immunoreactivity in the male genital organs of the rat," Cell Tissue Res, 300(2): 321-330, (2000).
Li et al., "P2X7 Receptor: A Novel Biomarker of Uterine Epithelial Cancers," Cancer Epidemiol Biomarkers Prev, 15(10)1906-1913, (2006).
MaCcallum et al, "Antibody-antigen Interactions: Contact Analysis and Binding Site Topography," J. Mol. Biol., 262:732-745, (1996).
Mager et al., "Prediction of the confirmation of the human P2X7 receptor," Letts Drug Des Discov, 3(10):675-682, (2006).
Maier et al., "Cloning of P2Y6 cDNAs and Identification of a Pseudogene: Comparison of P2Y Receptor Subtype Expression in Bone and Brain Tissues," Biochem and Biophys Res Comm, 237:297-302, (1997).
Mariuzza et at., "The structural basis of antigen-antibody recognition," Annual Review of Biophysics and Biophysical Chemistry, 16:139-159, (1987).
Mauro et al., "Chronic myelogenous leukaemia," Curr Opin Oncol, 13(1):3-7, (2001).
Meeker et al., "An additional breakpoint region in the BCL-1 locus associated with the t(11;14)(q13;q32) translocation of B-lymphocytic malignancy," Blood, 74:1801-1806, (1989).
Nawa et al., "Frequent loss of expression or aberrant alternative splicing of P2XM, a p53-inducible gene, in soft-tissue tumours," Br J Cancer, 80(8):1185-89, (1999).
Ngo et al "Computational complexity, protein structure prediction, and the Levinthal paradox," In Merz and Le Grand (eds), The protein folding problem and tertiary structure prediction, Birkhauser: Boston, pp. 491-495, (1994).
Nihei et al., "Pharmacologic properties of P2z/P2X7 receptor characterized in murine dendritic cells: role on the induction of apoptosis", Blood, 96(3)996-1005, (2000).
Parr et al., "Cloning and expression of a human P2U nucleotide receptor, a target for cystic fibrosis pharmacotherapy," Proc. Natl. Acad. Sci. USA, 91:3275-3279, (1994).
Paul, Fundamental Immunology, 3rd Edition, Raven Press, New York, Chapt. 9, pp. 292-295 (1993).
Paul, Fundamental Immunology, Lippincott Williams & Wilkins, p. 107, (1998).
PCT International Preliminary Examination Report of Mar. 14, 2003 for application PCT/AU2001/001614.
PCT International Preliminary Examination Report of May 1, 2003 for application PCT/AU02/00061.
PCT International Preliminary Examination Report of Aug. 1, 2001 for application PCT/AU00/00363.
PCT International Preliminary Examination Report of Dec. 17, 2003 for application PCT/AU02/001204.
PCT International Preliminary Report on Patentability of Jan. 5, 2011 for application PCT/AU09/000869.
PCT International Preliminary Report on Patentability of Jan. 16, 2014 for application PCT/AU2012/000795.
PCT International Preliminary Report on Patentability of Mar. 12, 2013 for application PCT/AU2011/001166.
PCT International Preliminary Report on Patentability of Mar. 16, 2010 for application PCT/AU08/001364.
PCT International Preliminary Report on Patentability of Mar. 16, 2010 for application PCT/AU08/001365.
PCT International Preliminary Report on Patentability of Apr. 15, 2009 for application PCT/AU07/001540.
PCT International Preliminary Report on Patentability of Apr. 15, 2009 for application PCT/AU07/001541.
PCT International Preliminary Report on Patentability of Jun. 26, 2012 for application PCT/AU2010/001741.
PCT International Search Report for application PCT/AU2010/001741 mailed Feb. 11, 2011.
PCT International Search Report of Feb. 5, 2002 for application PCT/AU2001/001614.
PCT International Search Report of Apr. 2, 2002 for application PCT/AU02/00061.
PCT International Search Report of Jul. 21, 2000 for application PCT/AU00/00363.
PCT International Search Report of Aug. 7, 2009 for application PCT/AU09/000869.
PCT International Search Report of Sep. 20, 2012 for applicatin PCT/AU2012/000795.
PCT International Search Report of Sep. 22, 2010 for application PCT/AU10/001070.
PCT International Search Report of Oct. 14, 2002 for application PCT/AU02/001204.
PCT International Search Report of Oct. 27, 2008 for application PCT/AU08/001364.
PCT International Search Report of Nov. 4, 2011 for application PCT/AU2011/001166.
PCT International Search Report of Nov. 9, 2007 for application PCT/AU07/001541.
PCT International Search Report of Nov. 21, 2008 for application PCT/AU08/001365.
PCT International Search Report of Nov. 2007 for application PCT/AU07/001540.
Peng et al., "P2Z purinoceptor, a special receptor for apoptosis induced by ATP in human leukemic lymphocytes," Chinese Med J, 112(4):356-362, (1999).
Perou et al., "Distinctive gene expression patterns in human mammary epithelial cells and breast cancers," Proc. Natl. Acad. Sci. USA, 96:9212-9217, (1999).
Poljak et al., "Production and structure of diabodies," Structure, 2:1121-1123, (1994).
Ralevic et al., "Receptors for Purines and Pyrimidines," Pharmacol Rev., 50(3):413-492, (1998).
Rassendren et al., "The permeabilizing ATP receptor, P2X7: Cloning and expression of a human cDNA," J Biol Chem, 272(9):5482-5486, (1997).
Ray et al., "Purinergic receptor distribution in endothelial cells in blood vessels: a basis for selection of coronary artery grafts," Atherosclerosis, 162:55-61, (2002).
Romagnoli et al., "Recent progress in the discovery of antagonists acting at P2X7 receptor," Expert Opinions Ther. Patents, 15(3):271-287, (2005).

(56) References Cited

OTHER PUBLICATIONS

Roman et al., "Cloning and Pharmacological Characterization of the Dog P2X7 Receptor," British Journal of Pharmacology, 158:1513-1526, (2009).
Rudikoff et al., "Single amino acid substitution altering antigen-binding specificity," PNAS, 79:1979-1983, (1982).
Sauer et al., "Calcium-dependence of hydrogen peroxide-induced c-fos expression and growth stimulation of multicellular prostate tumour spheroids," FEBS Left, 419: 201-205, (1997).
Schultze-Mosgau et al., "Characterization of calcium-mobilizing, purinergic P2Y2 receptors in human ovarian cancer cells," Mol Human Reproduct., 6(5): 435-442, (2000).
Slater et al. "Early prostate cancer detected using expression of non-functional cytolytic P2X7 receptors," Histopathology, 44:206-215, (2004).
Slater et al., "Detection of preneoplasia in histologically normal prostate biopsies," Prost Cancer Prostat Dis, 4:92-96, (2001).
Slater et al., "Differentiation between cancerous and normal hyperplastic lobules in breast lesions," Breast Cancer Res Treat, 83:1-10, (2004).
Slater et al., "Expression of the apoptotic calcium channel P2X7 in the glandular epithelium is a marker for early prostate cancer and correlates with increasing PSA levels," J Mol Histol., 36:159-165, (2005).
Slater et al., "Increased expression of apoptotic markers in melanoma," Melanoma Res, 13(2):137-145, (2003).
Slater et al., "Markers for the development of early prostate cancer," J Pathol,199:368-377,(2003).
Sluyter et at., "Extracellular ATP increases cation fluxes in human erthrocytes by activation of the P2X7 receptor," J Biol Chem, 279(43):44749-44756, (2004).
Spieker-Polet et al., "Rabbit monoclonal antibodies: Generating a fusion partner to produce rabbit-rabbit hybridomas," Proc. Natl. Acad. Sci USA, 92:9348-9352, (1995).
Supplementary European Search Report and European Search Opinion for application EP08800000 (published as EP2201026) mailed Oct. 29, 2012.
Supplementary European Search Report and European Search Opinion for application EP09771858 (published as EP2318438) mailed Oct. 24, 2012.
Supplementary European Search Report and European Search Opinion for application EP10838429 (published as EP2516470) mailed Apr. 13, 2013.
Supplementary European Search Report of Mar. 4, 2011 for application EP01270623 (published as EP1352085).
Supplementary European Search Report of May 21, 2010 for application EP07815345 (published as EP2082032).
Supplementary European Search Report of Aug. 16, 2010 for application EP08800001 (published as EP2201377).
Supplementary European Search Report of Nov. 8, 2002 for application EP00918600 (published as EP1179183).
Supplementary Partial European Search Report of Apr. 29, 2005 for application EP02715313 (published as EP1360203).
Surprenant et al., "The cytosolic P2Z receptor for extracellular ATP identified as a P2X receptor (P2X7)," Science, 272:735-738, (1996).
Tockman et al., "Considerations in Bringing a Cancer Biomarker to Clinical Application," Cancer Res, 52:2711s-2718s, (1992).
Torres et al., "Hetero-oligomeric Assembly of P2X Receptor Subunits," J Biol Chem, 274(10):6653-6659, (1999).
Tosatto et al., "Large-Scale Prediction of Protein Structure and Function from Sequence," Current Pharmaceutical Design, 12:2067-2086, (2006).
U.S. Appl. No. 10/019,356 (now U.S. Pat. No. 7,183,064), Final Office Action mailed May 9, 2006.
U.S. Appl. No. 10/019,356 (now U.S. Pat. No. 7,183,064), Non-Final Office Action mailed Jul. 19, 2005.
U.S. Appl. No. 10/019,356 (now U.S. Pat. No. 7,183,064), Notice of Allowance mailed Oct. 11, 2006.
U.S. Appl. No. 10/019,356 (now U.S. Pat. No. 7,183,064), Requirement for Restriction/Election mailed Mar. 18, 2005.
U.S. Appl. No. 10/450,205 (now Abandoned, Publication No. 2004/0067542), Final Office Action mailed Sep. 7, 2007.
U.S. Appl. No. 10/450,205 (now Abandoned, Publication No. 2004/0067542), Non-Final Office Action mailed Dec. 19, 2006.
U.S. Appl. No. 10/450,205 (now Abandoned, Publication No. 2004/0067542), Requirement for Restriction/Election mailed Sep. 6, 2006.
U.S. Appl. No. 10/622,313 (now U.S. Pat. No. 7,326,415), Non-Final Office Action mailed Nov. 30, 2006.
U.S. Appl. No. 10/622,313 (now U.S. Pat. No. 7,326,415), Notice of Allowance and Examiner Interview Summary Record mailed Sep. 5, 2007.
U.S. Appl. No. 10/622,313 (now U.S. Pat. No. 7,326,415), Requirement for Restriction/Election mailed Jun. 16, 2006.
U.S. Appl. No. 11/566,472 (now Abandoned, Publication No. 2007/0248963), Examiner Interview Summary Record mailed Dec. 30, 2009.
U.S. Appl. No. 11/566,472 (now Abandoned, Publication No. 2007/0248963), Final Office Action mailed Jan. 12, 2009.
U.S. Appl. No. 11/566,472 (now Abandoned, Publication No. 2007/0248963), Final Office Action mailed Mar. 9, 2010.
U.S. Appl. No. 11/566,472 (now Abandoned, Publication No. 2007/0248963), Non-Final Office Action mailed Jun. 16, 2008.
U.S. Appl. No. 11/566,472 (now Abandoned, Publication No. 2007/0248963), Non-Final Office Action mailed Aug. 26, 2009.
U.S. Appl. No. 11/566,472 (now Abandoned, Publication No. 2007/0248963), Requirement for Restriction/Election mailed Dec. 17, 2007.
U.S. Appl. No. 11/968,607 (now U.S. Pat. No. 7,531,171), Non-Final Office Action mailed Sep. 26, 2008.
U.S. Appl. No. 11/968,607 (now U.S. Pat. No. 7,531,171), Notice of Allowance mailed Jan. 9, 2009.
U.S. Appl. No. 11/968,607 (now U.S. Pat. No. 7,531,171), Requirement for Restriction/Election mailed Aug. 19, 2008.
U.S. Appl. No. 12/043,083 (now Abandoned, Publication No. 2008/0227122), Non-Final Office Action mailed Nov. 26, 2010.
U.S. Appl. No. 12/043,083 (now Abandoned, Publication No. 2008/0227122), Notice of Allowance mailed Aug. 5, 2011.
U.S. Appl. No. 12/043,083 (now Abandoned, Publication No. 2008/0227122), Requirement for Restriction/Election mailed Jul. 21, 2010.
U.S. Appl. No. 12/417,989 (now U.S. Pat. No. 7,888,473), Non-Final Office Action mailed Jun. 16, 2010.
U.S. Appl. No. 12/417,989 (now U.S. Pat. No. 7,888,473), Notice of Allowance mailed Sep. 24, 2010.
U.S. Appl. No. 12/445,258 (now Abandoned, Publication No. 2010/0036101), Non-Final Office Action mailed Oct. 18, 2011.
U.S. Appl. No. 12/445,258 (now Abandoned, Publication No. 2010/0036101), Requirement for Restriction/Election mailed May 6, 2011.
U.S. Appl. No. 12/445,273 (now U.S. Pat. No. 8,067,550), Non-Final Office Action mailed Oct. 1, 2010.
U.S. Appl. No. 12/445,273 (now U.S. Pat. No. 8,067,550), Notice of Allowance mailed Mar. 30, 2011.
U.S. Appl. No. 12/445,273 (now U.S. Pat. No. 8,067,550), Notice of Allowance mailed Jul. 8, 2011.
U.S. Appl. No. 12/445,273 (now U.S. Pat. No. 8,067,550), Requirement for Restriction/Election mailed Aug. 9, 2010.
U.S. Appl. No. 12/677,795 (now U.S. Pat. No. 8,293,491), Notice of Allowance mailed Jun. 22, 2012.
U.S. Appl. No. 12/677,795 (now U.S. Pat. No. 8,293,491), Restriction/Election Requirement mailed Oct. 12, 2011.
U.S. Appl. No. 12/677,799, Non-Final Office Action mailed Jun. 21, 2012.
U.S. Appl. No. 12/677,799, Notice of Allowance and Examiner Interview Summary Record mailed Dec. 10, 2012.
U.S. Appl. No. 12/677,799, Notice of Allowance mailed Jan. 9, 2013.
U.S. Appl. No. 12/677,799, Requirement for Restriction/Election mailed Feb. 23, 2012.
U.S. Appl. No. 12/878,865 (now Abandoned, Publication No. 2011/0111431), Non-Final Office Action mailed Oct. 20, 2011.

(56) References Cited

OTHER PUBLICATIONS

U.S. Appl. No. 12/878,865 (now Abandoned, Publication No. 2011/0111431), Requirement for Restriction/Election mailed Mar. 25, 2011.
U.S. Appl. No. 12/975,341 (now U.S. Pat. No. 8,080,635), Non-Final Office Action mailed Mar. 24, 2011.
U.S. Appl. No. 12/975,341 (now U.S. Pat. No. 8,080,635), Notice of Allowance mailed Aug. 17, 2011.
U.S. Appl. No. 13/002,647, Non-Final Office Action mailed Dec. 20, 2012.
U.S. Appl. No. 13/002,647, Notice of Allowance mailed Aug. 2, 2013.
U.S. Appl. No. 13/002,647, Requirement for Restriction/Election mailed Aug. 7, 2012.
U.S. Appl. No. 13/298,222, Final Office Action mailed Sep. 7, 2012.
U.S. Appl. No. 13/298,222, Non-Final Office Action mailed Feb. 13, 2012.
U.S. Appl. No. 13/298,222, Notice of Allowance and Examiner Interview Summary Record mailed Nov. 27, 2012.
U.S. Appl. No. 13/391,619, Requirement for Restriction/Election mailed Aug. 5, 2014.
U.S. Appl. No. 13/518,382, Final Office Action mailed Dec. 30, 2013.
U.S. Appl. No. 13/518,382, Non-Final Office Action mailed Jun. 18, 2013.
U.S. Appl. No. 13/518,382, Non-Final Office Action mailed Sep. 18, 2013.
U.S. Appl. No. 13/518,382, Notice of Allowance and Examiner Initiated Interview Summary mailed May 5, 2014.
U.S. Appl. No. 13/518,382, Requirement for Restriction/Election mailed Mar. 21, 2013.
U.S. Appl. No. 13/626,833, Non-Final Office Action mailed Jun. 13, 2013.
U.S. Appl. No. 13/626,833, Notice of Allowance and Examiner Initiated Interview Summary mailed Sep. 27, 2013.
U.S. Appl. No. 13/766,630, Non-Final Office Action mailed Aug. 19, 2013.
U.S. Appl. No. 13/766,630, Notice of Allowance and Examiner Initiated Interview Summary mailed Dec. 11, 2013.
U.S. Appl. No. 13/821,555, Requirement for Restriction/Election mailed Jun. 19, 2014.
U.S. Appl. No. 13/841,692, Requirement for Restriction/Election mailed Sep. 16, 2014.
U.S. Appl. No. 12/677,795 (now U.S. Pat. No. 8,293,491), Non-Final Office Action mailed Feb. 29, 2012.
Uniprot entry Q4VKI0_Human P2X7 Isoform E, UniProt Consortium, (2005).
Uniprot entry Q4VKI1_Human P2X7 Isoform F, UniProt Consortium, (2005).
Uniprot sequence entry: Accession No. Q4VKH8, "P2X7 isoform H," Jul. 2005. [Retrieved from the Internet Sep. 9, 2013: <URL: http:// www.ncbi.nlm.nih.gov/protein/Q4VKH8>].
Uniprot sequence entry: Accession No. Q4VKH9, "P2X7 isoform G," Jul. 2005. [Retrieved from the Internet Sep. 9, 2013: <URL: http:// www.ncbi.nlm.nih.gov/protein/Q4VKH9>].
Uniprot sequence entry: Accession No. Q4VKI2, "P2X7 isoform D," Jul. 2005. [Retrieved from the Internet Sep. 9, 2013: <URL: http:// www.ncbi.nlm.nih.gov/protein/Q4VKI2>].
Uniprot sequence entry: Accession No. Q4VKI4, "P2X7 isoform B," Jul. 2005 [Retrieved from the internet Sep. 9, 2013: <URL: http:// www.ncbi.nlm.nih.gov/protein/Q4VKI4>].
Urano et al., "Cloning of P2XM, a novel human P2X receptor gene regulated by p53, " Cancer Res, 57:3281-87, (1997).
Virginio et al., "Kinetics of cell lysis, dye uptake and permeability changes in cells expressing the rat P2X7 receptor," J Physiol., 519(2):335-346, (1999).

von Kugelgen et al., "Molecular Pharmacology of P2Y-receptors," Naunyn Scmiedebergs Arch Pharmacal, 362:(4-5)310-323, (2000).
Vulchanova et al., "Immunohistochemical study of the P2X2 and P2X3 receptor subunits in rat and monkey sensory neurons and their central terminals," Neuropharmacol, 36(9):1229-1242, (1997).
Wagstaff et al ., "Extracellular ATP activates multiple signalling pathways and potentiates growth factor-induced c-fos gene expression in MCF-7 breast cancer cells," Carcinogenesis 21(12):2175-2181, (2000).
Wang et al., "P2X7 receptor-mediated apoptosis of human cervical epithelial cells," Am. J Physiol, 287:1349-1358, (2004).
Ward et al., "Binding activities of a repertoire of single immunoglobulin variable domains secreted from Escherichia coli," Nature 341:544-546, (1989).
Wasilenko et al, "Calcium signaling in prostate cancer cells: Evidence for multiple receptors and enhanced sensitivity to bombesin/GRP," The Prostate 30:167-173 (1997).
Wells "Additivity of mutational effects in proteins," Biochemistry, 29(37):8509-8517, (1990).
White et al., "P2Y purinergic receptors regulate the growth of human melanomas," Cancer Letts, 224:81-91, (2005).
Wiley et al., "A single nucleotide polymorphism is associated with loss of function of the monocyte P2X7 receptor," Blood, 96(11):17, (2000). Abstract.
Wiley at al., "An Ile-568 to Asn polymorphism prevents normal trafficking and function of the human P2X7 receptor," J Biol Chem 278 (19):17108-17113, (2003).
Wiley et al., "Genetic polymorphisms of the human P2X7 receptor and relationship to function," Drug Dev Res, 53(2-3):72-76, (2001).
Williams at al., "Purinergic and pyrimidinergic receptors as potential drug targets," Biochem Pharm, 59:1173-1184, (2000).
Winkler et al., "Changing the antibody binding specificity by single point mutations of an Anti-p24 (HIV-1) antibody," Journal of Immunology, 165:4505-4514, (2000).
Worthington et al., "Point mutations confer loss of ATP-induced human P2X7 receptor function," FEBS Lett, 512:43-46, (2002).
Wurl et al., "High prognostic significance of Mdm2/p53 co-overexpression in soft tissue sarcomas of the extremities," Oncogene,16(9):1183-85, (1998).
U.S. Appl. No. 13/391,619, Notice of Allowance mailed Apr. 27, 2015.
U.S. Appl. No. 14/067,873, Requirement for Restriction/Election mailed Jun. 4, 2015.
Supplementary European Search Report and European Search Opinion for application EP10809371.7 (published as ER2467404) mailed Dec. 21, 2012.
Supplementary European Search Report and European Search Opinion for application EP11822941.8 (published as EP2613808) mailed Jan. 7, 2014.
Supplementary European Search Report and European Search Opinion for application EP12807960.5 (published as EP2726095) mailed Dec. 5, 2014.
U.S. Appl. No. 13/841,692, Non-Final Office Action mailed Feb. 26, 2015.
Muyldermans et al., "Nanobodies: Natural Single-Domain Antibodies," Annu. Rev. Biochem., 82:17.1-17.23, (2013).
U.S. Appl. No. 13/391,619, Non-Final Office Action mailed Dec. 23, 2014.
U.S. Appl. No. 14/218,935, Non-Final Office Action mailed Sep. 11, 2014.
Feng et al., "Endogenously Expressed Truncated P2X, Receptor Lacking the C-Terminal (P2X7-RTr) is Preferentially Upregulated in Epithelial Cancer Cells and Fails to Mediate Ligand-Induced Pore Formation and Apoptosis," 10th Symposium European Society for the Study of Purine and Pyrimidine Metabolism in Man, Abstract and Programme, Jun. 8-11, 2005.
Feng et al., "Endogenously Expressed Truncated P2X7 Receptor Lacking the C-Terminus is Preferentially Upregulated in Epithelial Cancer Cells and Fails to Mediate Ligand-induced Pore Formation and Apoptosis," Nucleosides, Nucleotides and Nucleic Acids, 25:1271-1276, (2006).

Figure 1

SEQ ID NO:1

```
  1    MPACCSCSDV  FQYETNKVTR  IQSMNYGTIK  WFFHVIIFSY  VCFALVSDKL  YQRKEPVISS
 61    VHTKVKGIAE  VKEEIVENGV  KKLVHSVFDT  ADYTFPLQGN  SFFVMTNFLK  TEGQEQRLCP
121    EYPTRRTLCS  SDRGCKKGWM  DPQSKGIQTG  RCVVHEGNQK  TCEVSAWCPI  EAVEEAPRPA
181    LLNSAENFTV  LIKNNIDFPG  HNYTTRNILP  GLNITCTFHK  TQNPQCPIFR  LGDIFRETGD
241    NFSDVAIQGG  IMGIEIYWDC  NLDRWFHHCR  PKYSFRRLDD  KTTNVSLYPG  YNFRYAKYYK
301    ENNVEKRTLI  KVFGIRFDIL  VFGTGGKFDI  IQLVVYIGST  LSYFGLAAVF  IDFLIDTYSS
361    NCCRSHIYPW  CKCCQPCVVN  EYYYRKKCES  IVEPKPTLKY  VSFVDESHIR  MVNQQLLGRS
421    LQDVKGQEVP  RPAMDFTDLS  RLPLALHDTP  PIPGQPEEIQ  LLRKEATPRS  RDSPVWCQCG
481    SCLPSQLPES  HRCLEELCCR  KKPGACITTS  ELFRKLVLSR  HVLQFLLLYQ  EPLLALDVDS
541    TNSRLRHCAY  RCYATWRFGS  QDMADFAILP  SCCRWRIRKE  FPKSEGQYSG  FKSPY
```

Figure 2

SEQ ID NO:2

```
  1    MPACCSCSDV FQYETNKVTR IQSMNYGTIK WFFHVIIFSY VCFALVSDKL YQRKEPVISS
 61    VHTKVKGIAE VKEEIVENGV KKLVHSVFDT ADYTFPLQGN SFFVMTNFLK TEGQEQRLCP
121    EYPTRRTLCS SDRGCKKGWM DPQSKGIQTG RCVVHEGNQK TCEVSAWCPI EAVEEAPRPA
181    LLNSAENFTV LIKNNIDFPG HNYTTRNILP GLNITCTFHK TQNPQCPIFR LGDIFRETGD
241    NFSDVAIQGG IMGIEIYWDC NLDRWFHHCR PKYSFRRLDD KTTNVSLYPG YNFRYAKYYK
301    ENNVEKRTLI KVFGIRFDIL VFGTGGKFDI IQLVVYIGST LSYFGLAAVF IDFLIDTYSS
361    NCCRSHIYPW CKCCQPCVVN EYYYRKKCES IVEPKPTLKY VSFVDESHIR MVNQQLLGRS
421    LQDVKGQEVP RPAMDFTDLS RLPLALHDTP PIPGQPEEIQ LLRKEATPRS RDSPVWCQCG
481    SCLPSQLPES HRCLEELCCR KKPGACITTS ELFRKLVLSR HVLQFLLLYQ EPLLALDVDS
541    TNSRLRHCAY RCYATWRFGS QDMADFAILP SCCRWRIRKE FPKSEGQYSG FKSPY
```

Figure 3

SEQ ID NO:3

```
1     MPACCSCSDV FQYETNKVTR IQSMNYGTIK WFFHVIIFSY VCFALVSDKL YQRKEPVISS
61    VHTKVKGIAE VKEEIVENGV KKLVHSVFDT ADYTFPLQGN SFFVMTNFLK TEGQEQRLCP
121   EYPTRRTLCS SDRGCKKGWM DPQSKGIQTG RCVVHEGNQK TCEVSAWCPI EAVEEAPRPA
181   LLNSAENFTV LIKNNIDFPG HNYTTRNILP GLNITCTFHK TQNPQCPIFR LGDIFRETGD
241   NFSDVAIQGG IMGIEIYWDC NLDRWFHHCR PKYSFRRLDD KTTNVSLYPG YNFRYAKYYK
301   ENNVEKRTLI KVFGIRFDIL VFGTGGKFDI IQLVVYIGST LSYFGLAAVF IDFLIDTYSS
361   NCCRSHIYPW CKCCQPCVVN EYYYRKKCES IVEPKPTLKY VSFVDESHIR MVNQQLLGRS
421   LQDVKGQEVP RPAMDFTDLS RLPLALHDTP PIPGQPEEIQ LLRKEATPRS RDSPVWCQCG
481   SCLPSQLPES HRCLEELCCR KKPGACITTS ELFRKLVLSR HVLQFLLLYQ EPLLALDVDS
      541        TNSRLRHCAY RCYATWRFGS QDMADFAILP SCCRWRIRKE FPKSEGQYSG FKSPY
```

SEQ ID NO: 4
MADIVMTQSQKFMSTSVGDRVSVTCKASQNVGTNVAWYQQKPGQSPKALIYSASFRY
SGVPDRFTGSGSGTDFTLTISNVQSEDLAEFFCQQYNSYPFTFGSGTRLEIKGGGGSG
GGGSGGGGSDVKLVESGGGLVKLGGSLKLSCAASGFTFSSYYMSWVRQTPEKRLEL
VAAINSNGGSTYYPDTVKGRFTISRDNAKNTLYLQMSSLKSEDTAFYYCTR**HYSSRFF
DV**WGAGTTVTVSSAAADYKDDDDKAAAHHHHHH (b)

2F6 IgG2a, #AIBN20090907

| | Name | Retention Time | Area | % Area | Height |
|---|---|---|---|---|---|
| 1 | Peak1 | 5.985 | | | |
| 2 | Peak2 | 8.473 | 823930 | 100.00 | 33247 |
| 3 | Peak3 | 8.933 | | | |

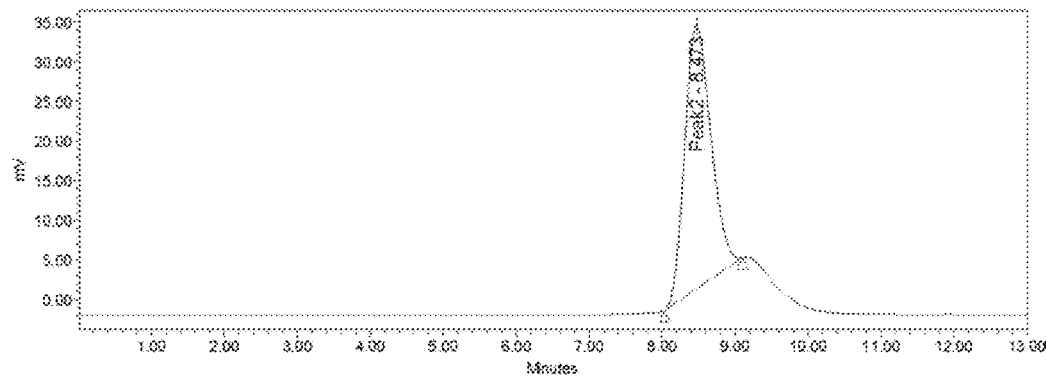

SDS-PAGE lanes:

1) Molecular weight marker
   (Invitrogen SeeBlue2 prestained marker)

2) Final Product batch # 20090907

3) Final Product batch # 20090907 4-fold diluted

MCF-7 control cells (Day 1)    MCF-7, 20 µg/mL 2F6 (Day 1)

Phase contrast photomicrograph 20x objective    Phase contrast photomicrograph 20x objective viable    dead

Figure 17

| | | |
|---|---|---|
| WT | HYSSRFFDV | (SEQ ID NO:34) |
| Mutant #9 | NFKLMYYNV | (SEQ ID NO:13) |
| Mutant #10 | NYRGDYYET | (SEQ ID NO:8) |
| Mutant #18 | HFSRGYYDV | (SEQ ID NO:14) |
| Mutant #20 | YHVIQYLGP | (SEQ ID NO:19) |
| Mutant #21 | NFLESYFEA | (SEQ ID NO:7) |
| Mutant #24 | NYLPMYYEV | (SEQ ID NO:12) |
| Mutant #36 | HYIKVYYEA | (SEQ ID NO:15) |
| Mutant #37 | HYSSRFFEV | (SEQ ID NO:16) |
| Mutant #39 | NFRVMFFKA | (SEQ ID NO:17) |
| Mutant #42 | HFQRGYYNI | (SEQ ID NO:10) |
| Mutant #43 | HYSSRFFEV | (SEQ ID NO:16) |
| Mutant #44 | YHVIQYLGP | (SEQ ID NO:19) |
| Mutant #52 | HYSKEYYNI | (SEQ ID NO:9) |
| Mutant #66 | YFPLVYYDV | (SEQ ID NO:11) |
| Mutant #75 | DFTVPFYNA | (SEQ ID NO:20) |
| Mutant #78 | NYDKKYFDV | (SEQ ID NO:21) |
| Mutant #83 | YFPLVYYDV | (SEQ ID NO:11) |

SEQUENCE LISTING

```
<160> NUMBER OF SEQ ID NOS: 57

<210> SEQ ID NO 1
<211> LENGTH: 595
<212> TYPE: PRT
<213> ORGANISM: Homo sapiens

<400> SEQUENCE: 1

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
            35                  40                  45

Lys Leu Tyr Gln Arg Lys Glu Pro Val Ile Ser Ser Val His Thr Lys
        50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190
```

```
Lys Asn Asn Ile Asp Phe Pro Gly His Asn Tyr Thr Thr Arg Asn Ile
            195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Cys Gln Pro Cys Val Val Asn Glu Tyr Tyr
    370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
        435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595
```

<210> SEQ ID NO 2
<211> LENGTH: 260
<212> TYPE: PRT
<213> ORGANISM: Artificial Sequence
<220> FEATURE:
<223> OTHER INFORMATION: Synthesized

<400> SEQUENCE: 2

```
Ser Asp Lys Leu Tyr Gln Arg Lys Glu Pro Val Ile Ser Ser Val His
1               5                   10                  15

Thr Lys Val Lys Gly Ile Ala Glu Val Lys Glu Glu Ile Val Glu Asn
            20                  25                  30

Gly Val Lys Lys Leu Val His Ser Val Phe Asp Thr Ala Asp Tyr Thr
        35                  40                  45

Phe Pro Leu Gln Gly Asn Ser Phe Phe Val Met Thr Asn Phe Leu Lys
    50                  55                  60

Thr Glu Gly Gln Glu Gln Arg Leu Cys Pro Glu Tyr Pro Thr Arg Arg
65                  70                  75                  80

Thr Leu Cys Ser Ser Asp Arg Gly Cys Lys Lys Gly Trp Met Asp Pro
                85                  90                  95

Gln Ser Lys Gly Ile Gln Thr Gly Arg Cys Val Val His Glu Gly Asn
            100                 105                 110

Gln Lys Thr Cys Glu Val Ser Ala Trp Cys Pro Ile Glu Ala Val Glu
        115                 120                 125

Glu Ala Pro Arg Pro Ala Leu Leu Asn Ser Ala Glu Asn Phe Thr Val
    130                 135                 140

Leu Ile Lys Asn Asn Ile Asp Phe Pro Gly His Asn Tyr Thr Thr Arg
145                 150                 155                 160

Asn Ile Leu Pro Gly Leu Asn Ile Thr Cys Thr Phe His Lys Thr Gln
                165                 170                 175

Asn Pro Gln Cys Pro Ile Phe Arg Leu Gly Asp Ile Phe Arg Glu Thr
            180                 185                 190

Gly Asp Asn Phe Ser Asp Val Ala Ile Gln Gly Gly Ile Met Gly Ile
        195                 200                 205

Glu Ile Tyr Trp Asp Cys Asn Leu Asp Arg Trp Phe His His Cys Arg
    210                 215                 220

Pro Lys Tyr Ser Phe Arg Arg Leu Asp Asp Lys Thr Thr Asn Val Ser
225                 230                 235                 240

Leu Tyr Pro Gly Tyr Asn Phe Arg Tyr Ala Lys Tyr Tyr Lys Glu Asn
                245                 250                 255

Asn Val Glu Lys
            260
```

<210> SEQ ID NO 3
<211> LENGTH: 287
<212> TYPE: PRT
<213> ORGANISM: Artificial Sequence
<220> FEATURE:
<223> OTHER INFORMATION: Synthesized

<400> SEQUENCE: 3

```
Val Ser Asp Lys Leu Tyr Gln Arg Lys Glu Pro Val Ile Ser Ser Val
1               5                   10                  15

His Thr Lys Val Lys Gly Ile Ala Glu Val Lys Glu Glu Ile Val Glu
            20                  25                  30

Asn Gly Val Lys Lys Leu Val His Ser Val Phe Asp Thr Ala Asp Tyr
        35                  40                  45
```

-continued

Thr Phe Pro Leu Gln Gly Asn Ser Phe Val Met Thr Asn Phe Leu
 50                  55                  60
Lys Thr Glu Gly Gln Glu Gln Arg Leu Cys Pro Glu Tyr Pro Thr Arg
 65                  70                  75                  80
Arg Thr Leu Cys Ser Ser Asp Arg Gly Cys Lys Lys Gly Trp Met Asp
                 85                  90                  95
Pro Gln Ser Lys Gly Ile Gln Thr Gly Arg Cys Val Val His Glu Gly
            100                 105                 110
Asn Gln Lys Thr Cys Glu Val Ser Ala Trp Cys Pro Ile Glu Ala Val
        115                 120                 125
Glu Glu Ala Pro Arg Pro Ala Leu Leu Asn Ser Ala Glu Asn Phe Thr
130                 135                 140
Val Leu Ile Lys Asn Asn Ile Asp Phe Pro Gly His Asn Tyr Thr Thr
145                 150                 155                 160
Arg Asn Ile Leu Pro Gly Leu Asn Ile Thr Cys Thr Phe His Lys Thr
                165                 170                 175
Gln Asn Pro Gln Cys Pro Ile Phe Arg Leu Gly Asp Ile Phe Arg Glu
            180                 185                 190
Thr Gly Asp Asn Phe Ser Asp Val Ala Ile Gln Gly Gly Ile Met Gly
        195                 200                 205
Ile Glu Ile Tyr Trp Asp Cys Asn Leu Asp Arg Trp Phe His His Cys
210                 215                 220
Arg Pro Lys Tyr Ser Phe Arg Arg Leu Asp Asp Lys Thr Thr Asn Val
225                 230                 235                 240
Ser Leu Tyr Pro Gly Tyr Asn Phe Arg Tyr Ala Lys Tyr Tyr Lys Glu
                245                 250                 255
Asn Asn Val Glu Lys Arg Thr Leu Ile Lys Val Phe Gly Ile Arg Phe
            260                 265                 270
Asp Ile Leu Val Phe Gly Thr Gly Lys Phe Asp Ile Ile Gln
        275                 280                 285

<210> SEQ ID NO 4
<211> LENGTH: 262
<212> TYPE: PRT
<213> ORGANISM: Artificial Sequence
<220> FEATURE:
<223> OTHER INFORMATION: Synthesized

<400> SEQUENCE: 4

Met Ala Asp Ile Val Met Thr Gln Ser Gln Lys Phe Met Ser Thr Ser
  1               5                  10                  15
Val Gly Asp Arg Val Ser Val Thr Cys Lys Ala Ser Gln Asn Val Gly
                 20                  25                  30
Thr Asn Val Ala Trp Tyr Gln Gln Lys Pro Gly Gln Ser Pro Lys Ala
             35                  40                  45
Leu Ile Tyr Ser Ala Ser Phe Arg Tyr Ser Gly Val Pro Asp Arg Phe
 50                  55                  60
Thr Gly Ser Gly Ser Gly Thr Asp Phe Thr Leu Thr Ile Ser Asn Val
 65                  70                  75                  80
Gln Ser Glu Asp Leu Ala Glu Phe Phe Cys Gln Gln Tyr Asn Ser Tyr
                 85                  90                  95
Pro Phe Thr Phe Gly Ser Gly Thr Arg Leu Glu Ile Lys Gly Gly Gly
            100                 105                 110
Gly Ser Gly Gly Gly Gly Ser Gly Gly Gly Ser Asp Val Lys Leu
        115                 120                 125

Val Glu Ser Gly Gly Gly Leu Val Lys Leu Gly Gly Ser Leu Lys Leu
130                 135                 140

Ser Cys Ala Ala Ser Gly Phe Thr Phe Ser Ser Tyr Tyr Met Ser Trp
145                 150                 155                 160

Val Arg Gln Thr Pro Glu Lys Arg Leu Glu Leu Val Ala Ala Ile Asn
            165                 170                 175

Ser Asn Gly Gly Ser Thr Tyr Tyr Pro Asp Thr Val Lys Gly Arg Phe
            180                 185                 190

Thr Ile Ser Arg Asp Asn Ala Lys Asn Thr Leu Tyr Leu Gln Met Ser
        195                 200                 205

Ser Leu Lys Ser Glu Asp Thr Ala Phe Tyr Tyr Cys Thr Arg His Tyr
210                 215                 220

Ser Ser Arg Phe Phe Asp Val Trp Gly Ala Gly Thr Thr Val Thr Val
225                 230                 235                 240

Ser Ser Ala Ala Ala Asp Tyr Lys Asp Asp Asp Lys Ala Ala Ala
                245                 250                 255

His His His His His His
            260

<210> SEQ ID NO 5
<211> LENGTH: 11
<212> TYPE: PRT
<213> ORGANISM: Artificial Sequence
<220> FEATURE:
<223> OTHER INFORMATION: Synthesized

<400> SEQUENCE: 5

Lys Ala Ser Gln Asn Val Gly Thr Asn Val Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthesized

<400> SEQUENCE: 6

Ser Ala Ser Phe Arg Tyr Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthesized

<400> SEQUENCE: 7

Asn Phe Leu Glu Ser Tyr Phe Glu Ala
1               5

<210> SEQ ID NO 8
<211> LENGTH: 9
<212> TYPE: PRT
<213> ORGANISM: Artificial Sequence
<220> FEATURE:
<223> OTHER INFORMATION: Synthesized

<400> SEQUENCE: 8

Asn Tyr Arg Gly Asp Tyr Tyr Glu Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthesized

<400> SEQUENCE: 9

His Tyr Ser Lys Glu Tyr Tyr Asn Ile
1               5

<210> SEQ ID NO 10
<211> LENGTH: 9
<212> TYPE: PRT
<213> ORGANISM: Artificial Sequence
<220> FEATURE:
<223> OTHER INFORMATION: Synthesized

<400> SEQUENCE: 10

His Phe Gln Arg Gly Tyr Tyr Asn Ile
1               5

<210> SEQ ID NO 11
<211> LENGTH: 9
<212> TYPE: PRT
<213> ORGANISM: Artificial Sequence
<220> FEATURE:
<223> OTHER INFORMATION: Synthesized

<400> SEQUENCE: 11

Tyr Phe Pro Leu Val Tyr Tyr Asp Val
1               5

<210> SEQ ID NO 12
<211> LENGTH: 9
<212> TYPE: PRT
<213> ORGANISM: Artificial Sequence
<220> FEATURE:
<223> OTHER INFORMATION: Synthesized

<400> SEQUENCE: 12

Asn Tyr Leu Pro Met Tyr Tyr Glu Val
1               5

<210> SEQ ID NO 13
<211> LENGTH: 9
<212> TYPE: PRT
<213> ORGANISM: Artificial Sequence
<220> FEATURE:
<223> OTHER INFORMATION: Synthesized

<400> SEQUENCE: 13

Asn Phe Lys Leu Met Tyr Tyr Asn Val
1               5

<210> SEQ ID NO 14
<211> LENGTH: 9
<212> TYPE: PRT
<213> ORGANISM: Artificial Sequence
<220> FEATURE:
<223> OTHER INFORMATION: Synthesized

<400> SEQUENCE: 14

His Phe Ser Arg Gly Tyr Tyr Asp Val
1               5

-continued

```
<210> SEQ ID NO 15
<211> LENGTH: 9
<212> TYPE: PRT
<213> ORGANISM: Artificial Sequence
<220> FEATURE:
<223> OTHER INFORMATION: Synthesized

<400> SEQUENCE: 15

His Tyr Ile Lys Val Tyr Tyr Glu Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Synthesized

<400> SEQUENCE: 16

His Tyr Ser Ser Arg Phe Phe Glu Val
1               5

<210> SEQ ID NO 17
<211> LENGTH: 9
<212> TYPE: PRT
<213> ORGANISM: Artificial Sequence
<220> FEATURE:
<223> OTHER INFORMATION: Synthesized

<400> SEQUENCE: 17

Asn Phe Arg Val Met Phe Phe Lys Ala
1               5

<210> SEQ ID NO 18
<211> LENGTH: 9
<212> TYPE: PRT
<213> ORGANISM: Artificial Sequence
<220> FEATURE:
<223> OTHER INFORMATION: Synthesized

<400> SEQUENCE: 18

His Tyr Ser Ser Arg Phe Phe Glu Val
1               5

<210> SEQ ID NO 19
<211> LENGTH: 9
<212> TYPE: PRT
<213> ORGANISM: Artificial Sequence
<220> FEATURE:
<223> OTHER INFORMATION: Synthesized

<400> SEQUENCE: 19

Tyr His Val Ile Gln Tyr Leu Gly Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Synthesized

<400> SEQUENCE: 20

Asp Phe Thr Val Pro Phe Tyr Asn Ala
1               5

<210> SEQ ID NO 21
```

```
<211> LENGTH: 9
<212> TYPE: PRT
<213> ORGANISM: Artificial Sequence
<220> FEATURE:
<223> OTHER INFORMATION: Synthesized

<400> SEQUENCE: 21

Asn Tyr Asp Lys Lys Tyr Phe Asp Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthesized

<400> SEQUENCE: 22

Tyr Phe Pro Leu Val Tyr Tyr Asp Val
1               5

<210> SEQ ID NO 23
<211> LENGTH: 5
<212> TYPE: PRT
<213> ORGANISM: Artificial Sequence
<220> FEATURE:
<223> OTHER INFORMATION: Synthesized

<400> SEQUENCE: 23

Ser Tyr Tyr Met Ser
1               5

<210> SEQ ID NO 24
<211> LENGTH: 17
<212> TYPE: PRT
<213> ORGANISM: Artificial Sequence
<220> FEATURE:
<223> OTHER INFORMATION: Synthesized

<400> SEQUENCE: 24

Ala Ile Asn Ser Asn Gly Gly Ser Thr Tyr Tyr Pro Asp Thr Val Lys Gly
1               5                   10                  15

<210> SEQ ID NO 25
<211> LENGTH: 25
<212> TYPE: PRT
<213> ORGANISM: Artificial Sequence
<220> FEATURE:
<223> OTHER INFORMATION: Synthesized

<400> SEQUENCE: 25

Met Ala Asp Ile Val Met Thr Gln Ser Gln Lys Phe Met Ser Thr Ser
1               5                   10                  15

Val Gly Asp Arg Val Ser Val Thr Cys
            20                  25

<210> SEQ ID NO 26
<211> LENGTH: 15
<212> TYPE: PRT
<213> ORGANISM: Artificial Sequence
<220> FEATURE:
<223> OTHER INFORMATION: Synthesized

<400> SEQUENCE: 26

Trp Tyr Gln Gln Lys Pro Gly Gln Ser Pro Lys Ala Leu Ile Tyr
1               5                   10                  15
```

<210> SEQ ID NO 27
<211> LENGTH: 32
<212> TYPE: PRT
<213> ORGANISM: Artificial Sequence
<220> FEATURE:
<223> OTHER INFORMATION: Synthesized

<400> SEQUENCE: 27

Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Glu Phe Phe Cys
            20                  25                  30

<210> SEQ ID NO 28
<211> LENGTH: 10
<212> TYPE: PRT
<213> ORGANISM: Artificial Sequence
<220> FEATURE:
<223> OTHER INFORMATION: Synthesized

<400> SEQUENCE: 28

Phe Gly Ser Gly Thr Arg Leu Glu Ile Lys
1               5                   10

<210> SEQ ID NO 29
<211> LENGTH: 30
<212> TYPE: PRT
<213> ORGANISM: Artificial Sequence
<220> FEATURE:
<223> OTHER INFORMATION: Synthesized

<400> SEQUENCE: 29

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthesized

<400> SEQUENCE: 30

Trp Val Arg Gln Thr Pro Glu Lys Arg Leu Glu Leu Val Ala
1               5                   10

<210> SEQ ID NO 31
<211> LENGTH: 32
<212> TYPE: PRT
<213> ORGANISM: Artificial Sequence
<220> FEATURE:
<223> OTHER INFORMATION: Synthesized

<400> SEQUENCE: 31

Arg Phe Thr Ile Ser Arg Asp Asn Ala Lys Asn Thr Leu Tyr Leu Gln
1               5                   10                  15

Met Ser Ser Leu Lys Ser Glu Asp Thr Ala Phe Tyr Tyr Cys Thr Arg
            20                  25                  30

<210> SEQ ID NO 32
<211> LENGTH: 11
<212> TYPE: PRT
<213> ORGANISM: Artificial Sequence
<220> FEATURE:
<223> OTHER INFORMATION: Synthesized

<400> SEQUENCE: 32

Trp Gly Ala Gly Thr Thr Val Thr Val Ser Ser
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Synthesized

<400> SEQUENCE: 33

Gln Gln Tyr Asn Ser Tyr Pro Phe Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Synthesized

<400> SEQUENCE: 34

His Tyr Ser Ser Arg Phe Phe Asp Val
1               5

<210> SEQ ID NO 35
<211> LENGTH: 118
<212> TYPE: PRT
<213> ORGANISM: Artificial Sequence
<220> FEATURE:
<223> OTHER INFORMATION: Synthesized

<400> SEQUENCE: 35

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Phe Tyr Tyr Cys
                85                  90                  95

Thr Arg His Tyr Ser Ser Arg Phe Phe Asp Val Trp Gly Ala Gly Thr
            100                 105                 110

Thr Val Thr Val Ser Ser
        115

<210> SEQ ID NO 36
<211> LENGTH: 109
<212> TYPE: PRT
<213> ORGANISM: Artificial Sequence
<220> FEATURE:
<223> OTHER INFORMATION: Synthesized

<400> SEQUENCE: 36

Met Ala Asp Ile Val Met Thr Gln Ser Gln Lys Phe Met Ser Thr Ser

```
              1               5                  10                 15
Val Gly Asp Arg Val Ser Val Thr Cys Lys Ala Ser Gln Asn Val Gly
                20                  25                 30

Thr Asn Val Ala Trp Tyr Gln Gln Lys Pro Gly Gln Ser Pro Lys Ala
                35                  40                 45

Leu Ile Tyr Ser Ala Ser Phe Arg Tyr Ser Gly Val Pro Asp Arg Phe
            50                  55                 60

Thr Gly Ser Gly Ser Gly Thr Asp Phe Thr Leu Thr Ile Ser Asn Val
65                  70                  75                 80

Gln Ser Glu Asp Leu Ala Glu Phe Phe Cys Gln Gln Tyr Asn Ser Tyr
                85                  90                 95

Pro Phe Thr Phe Gly Ser Gly Thr Arg Leu Glu Ile Lys
                100                 105

<210> SEQ ID NO 37
<211> LENGTH: 242
<212> TYPE: PRT
<213> ORGANISM: Artificial Sequence
<220> FEATURE:
<223> OTHER INFORMATION: Synthesized

<400> SEQUENCE: 37

Met Ala Asp Ile Val Met Thr Gln Ser Gln Lys Phe Met Ser Thr Ser
1               5                  10                 15

Val Gly Asp Arg Val Ser Val Thr Cys Lys Ala Ser Gln Asn Val Gly
                20                  25                 30

Thr Asn Val Ala Trp Tyr Gln Gln Lys Pro Gly Gln Ser Pro Lys Ala
                35                  40                 45

Leu Ile Tyr Ser Ala Ser Phe Arg Tyr Ser Gly Val Pro Asp Arg Phe
            50                  55                 60

Thr Gly Ser Gly Ser Gly Thr Asp Phe Thr Leu Thr Ile Ser Asn Val
65                  70                  75                 80

Gln Ser Glu Asp Leu Ala Glu Phe Phe Cys Gln Gln Tyr Asn Ser Tyr
                85                  90                 95

Pro Phe Thr Phe Gly Ser Gly Thr Arg Leu Glu Ile Lys Gly Gly Gly
                100                 105                110

Gly Ser Gly Gly Gly Gly Ser Gly Gly Gly Gly Ser Asp Val Lys Leu
            115                 120                 125

Val Glu Ser Gly Gly Gly Leu Val Lys Leu Gly Gly Ser Leu Lys Leu
            130                 135                 140

Ser Cys Ala Ala Ser Gly Phe Thr Phe Ser Ser Tyr Tyr Met Ser Trp
145                 150                 155                 160

Val Arg Gln Thr Pro Glu Lys Arg Leu Glu Leu Val Ala Ala Ile Asn
                165                 170                 175

Ser Asn Gly Gly Ser Thr Tyr Tyr Pro Asp Thr Val Lys Gly Arg Phe
            180                 185                 190

Thr Ile Ser Arg Asp Asn Ala Lys Asn Thr Leu Tyr Leu Gln Met Ser
            195                 200                 205

Ser Leu Lys Ser Glu Asp Thr Ala Phe Tyr Tyr Cys Thr Arg His Tyr
            210                 215                 220

Ser Ser Arg Phe Phe Asp Val Trp Gly Ala Gly Thr Thr Val Thr Val
225                 230                 235                 240

Ser Ser

<210> SEQ ID NO 38
```

```
<211> LENGTH: 118
<212> TYPE: PRT
<213> ORGANISM: Artificial Sequence
<220> FEATURE:
<223> OTHER INFORMATION: Synthesized

<400> SEQUENCE: 38

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Phe Tyr Tyr Cys
                85                  90                  95

Thr Arg His Phe Ser Arg Gly Tyr Tyr Asp Val Trp Gly Ala Gly Thr
            100                 105                 110

Thr Val Thr Val Ser Ser
            115

<210> SEQ ID NO 39
<211> LENGTH: 242
<212> TYPE: PRT
<213> ORGANISM: Artificial Sequence
<220> FEATURE:
<223> OTHER INFORMATION: Synthesized

<400> SEQUENCE: 39

Met Ala Asp Ile Val Met Thr Gln Ser Gln Lys Phe Met Ser Thr Ser
1               5                   10                  15

Val Gly Asp Arg Val Ser Val Thr Cys Lys Ala Ser Gln Asn Val Gly
            20                  25                  30

Thr Asn Val Ala Trp Tyr Gln Gln Lys Pro Gly Gln Ser Pro Lys Ala
        35                  40                  45

Leu Ile Tyr Ser Ala Ser Phe Arg Tyr Ser Gly Val Pro Asp Arg Phe
    50                  55                  60

Thr Gly Ser Gly Ser Gly Thr Asp Phe Thr Leu Thr Ile Ser Asn Val
65                  70                  75                  80

Gln Ser Glu Asp Leu Ala Glu Phe Phe Cys Gln Gln Tyr Asn Ser Tyr
                85                  90                  95

Pro Phe Thr Phe Gly Ser Gly Thr Arg Leu Glu Ile Lys Gly Gly Gly
            100                 105                 110

Gly Ser Gly Gly Gly Gly Ser Gly Gly Gly Ser Asp Val Lys Leu
        115                 120                 125

Val Glu Ser Gly Gly Gly Leu Val Lys Leu Gly Gly Ser Leu Lys Leu
    130                 135                 140

Ser Cys Ala Ala Ser Gly Phe Thr Phe Ser Ser Tyr Tyr Met Ser Trp
145                 150                 155                 160

Val Arg Gln Thr Pro Glu Lys Arg Leu Glu Leu Val Ala Ala Ile Asn
                165                 170                 175

Ser Asn Gly Gly Ser Thr Tyr Tyr Pro Asp Thr Val Lys Gly Arg Phe
            180                 185                 190

Thr Ile Ser Arg Asp Asn Ala Lys Asn Thr Leu Tyr Leu Gln Met Ser
```

```
                195                 200                 205
Ser Leu Lys Ser Glu Asp Thr Ala Phe Tyr Tyr Cys Thr Arg His Phe
    210                 215                 220

Ser Arg Gly Tyr Tyr Asp Val Trp Gly Ala Gly Thr Thr Val Thr Val
225                 230                 235                 240

Ser Ser

<210> SEQ ID NO 40
<211> LENGTH: 118
<212> TYPE: PRT
<213> ORGANISM: Artificial Sequence
<220> FEATURE:
<223> OTHER INFORMATION: Synthesized

<400> SEQUENCE: 40

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Phe Tyr Tyr Cys
                85                  90                  95

Thr Arg Asn Tyr Asp Lys Lys Tyr Phe Asp Val Trp Gly Ala Gly Thr
            100                 105                 110

Thr Val Thr Val Ser Ser
        115

<210> SEQ ID NO 41
<211> LENGTH: 242
<212> TYPE: PRT
<213> ORGANISM: Artificial Sequence
<220> FEATURE:
<223> OTHER INFORMATION: Synthesized

<400> SEQUENCE: 41

Met Ala Asp Ile Val Met Thr Gln Ser Gln Lys Phe Met Ser Thr Ser
1               5                   10                  15

Val Gly Asp Arg Val Ser Val Thr Cys Lys Ala Ser Gln Asn Val Gly
            20                  25                  30

Thr Asn Val Ala Trp Tyr Gln Gln Lys Pro Gly Gln Ser Pro Lys Ala
        35                  40                  45

Leu Ile Tyr Ser Ala Ser Phe Arg Tyr Ser Gly Val Pro Asp Arg Phe
    50                  55                  60

Thr Gly Ser Gly Ser Gly Thr Asp Phe Thr Leu Thr Ile Ser Asn Val
65                  70                  75                  80

Gln Ser Glu Asp Leu Ala Glu Phe Phe Cys Gln Gln Tyr Asn Ser Tyr
                85                  90                  95

Pro Phe Thr Phe Gly Ser Gly Thr Arg Leu Glu Ile Lys Gly Gly Gly
            100                 105                 110

Gly Ser Gly Gly Gly Gly Ser Gly Gly Gly Gly Ser Asp Val Lys Leu
        115                 120                 125

Val Glu Ser Gly Gly Gly Leu Val Lys Leu Gly Gly Ser Leu Lys Leu
```

```
            130                 135                 140
Ser Cys Ala Ala Ser Gly Phe Thr Phe Ser Ser Tyr Tyr Met Ser Trp
145                 150                 155                 160

Val Arg Gln Thr Pro Glu Lys Arg Leu Glu Leu Val Ala Ala Ile Asn
                    165                 170                 175

Ser Asn Gly Gly Ser Thr Tyr Tyr Pro Asp Thr Val Lys Gly Arg Phe
                180                 185                 190

Thr Ile Ser Arg Asp Asn Ala Lys Asn Thr Leu Tyr Leu Gln Met Ser
            195                 200                 205

Ser Leu Lys Ser Glu Asp Thr Ala Phe Tyr Tyr Cys Thr Arg Asn Tyr
        210                 215                 220

Asp Lys Lys Tyr Phe Asp Val Trp Gly Ala Gly Thr Thr Val Thr Val
225                 230                 235                 240

Ser Ser

<210> SEQ ID NO 42
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa = H, F, W, or Y
<220> FEATURE:
<221> NAME/KEY: MISC_FEATURE
<222> LOCATION: (3)..(3)
<223> OTHER INFORMATION: Xaa = Any Amino Acid
<220> FEATURE:
<221> NAME/KEY: MISC_FEATURE
<222> LOCATION: (4)..(4)
<223> OTHER INFORMATION: Xaa = Any Amino Acid
<220> FEATURE:
<221> NAME/KEY: MISC_FEATURE
<222> LOCATION: (5)..(5)
<223> OTHER INFORMATION: Xaa = Any Amino Acid

<400> SEQUENCE: 42

His Xaa Xaa Xaa Xaa Tyr Tyr Asn Ile
1               5

<210> SEQ ID NO 43
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa = Y or F
<220> FEATURE:
<221> NAME/KEY: MISC_FEATURE
<222> LOCATION: (3)..(3)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (4)..(4)
<223> OTHER INFORMATION: Xaa = R, D, E, H, or K
<220> FEATURE:
<221> NAME/KEY: MISC_FEATURE
<222> LOCATION: (5)..(5)
<223> OTHER INFORMATION: Xaa = R, D, E, H, or K

<400> SEQUENCE: 43

His Xaa Xaa Xaa Xaa Tyr Tyr Asn Ile
```

```
<210> SEQ ID NO 44
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa = Y or F
<220> FEATURE:
<221> NAME/KEY: MISC_FEATURE
<222> LOCATION: (3)..(3)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (4)..(4)
<223> OTHER INFORMATION: Xaa = R, D, E, H, or K
<220> FEATURE:
<221> NAME/KEY: MISC_FEATURE
<222> LOCATION: (5)..(5)
<223> OTHER INFORMATION: Xaa = A, N, C, Q, G, I, L, M, F, P, S, T, W,
      or V

<400> SEQUENCE: 44

His Xaa Xaa Xaa Xaa Tyr Tyr Asn Ile
1               5

<210> SEQ ID NO 45
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa = Y or N
<220> FEATURE:
<221> NAME/KEY: MISC_FEATURE
<222> LOCATION: (2)..(2)
<223> OTHER INFORMATION: Xaa = H, F, W, or Y
<220> FEATURE:
<221> NAME/KEY: MISC_FEATURE
<222> LOCATION: (3)..(3)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (4)..(4)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (5)..(5)
<223> OTHER INFORMATION: Xaa = A, N, C, Q, G, I, L, M, F, P, S, T, W,
      or V

<400> SEQUENCE: 45

Xaa Xaa Xaa Xaa Xaa Tyr Tyr Asp Val
1               5

<210> SEQ ID NO 46
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
```

```
<223> OTHER INFORMATION: Xaa = Y or N
<220> FEATURE:
<221> NAME/KEY: MISC_FEATURE
<222> LOCATION: (2)..(2)
<223> OTHER INFORMATION: Xaa = H, F, W, or Y
<220> FEATURE:
<221> NAME/KEY: MISC_FEATURE
<222> LOCATION: (3)..(3)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (4)..(4)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (5)..(5)
<223> OTHER INFORMATION: Xaa = A, N, C, Q, G, I, L, M, F, P, S, T, W,
      or V

<400> SEQUENCE: 46

Xaa Xaa Xaa Xaa Xaa Tyr Tyr Glu Val
1               5

<210> SEQ ID NO 47
<211> LENGTH: 15
<212> TYPE: PRT
<213> ORGANISM: Artificial Sequence
<220> FEATURE:
<223> OTHER INFORMATION: Synthesized

<400> SEQUENCE: 47

Gly Gly Gly Gly Ser Gly Gly Gly Ser Gly Gly Gly Gly Ser
1               5                   10                  15

<210> SEQ ID NO 48
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa = R, D, E, H, K, N, C, Q, S, T, F, W, or Y
<220> FEATURE:
<221> NAME/KEY: MISC_FEATURE
<222> LOCATION: (2)..(2)
<223> OTHER INFORMATION: Xaa = R, D, E, H, K, F, W, or Y
<220> FEATURE:
<221> NAME/KEY: MISC_FEATURE
<222> LOCATION: (3)..(5)
<223> OTHER INFORMATION: Xaa = Any amino acid
<220> FEATURE:
<221> NAME/KEY: MISC_FEATURE
<222> LOCATION: (7)..(7)
<223> OTHER INFORMATION: Xaa = H, F, W, Y, A, G, I, L, V
<220> FEATURE:
<221> NAME/KEY: MISC_FEATURE
<222> LOCATION: (8)..(8)
<223> OTHER INFORMATION: Xaa = R, D, E, H, K, A, N, C, Q, G, I, L, M, F,
      P, S, T, W, or V
<220> FEATURE:
<221> NAME/KEY: MISC_FEATURE
<222> LOCATION: (9)..(9)
<223> OTHER INFORMATION: Xaa = A, N, C, Q, G, I, L, M, F, P, S, T, W,
      or V

<400> SEQUENCE: 48

Xaa Xaa Xaa Xaa Xaa Tyr Xaa Xaa Xaa
1               5
```

```
<210> SEQ ID NO 49
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa= Y or F
<220> FEATURE:
<221> NAME/KEY: MISC_FEATURE
<222> LOCATION: (3)..(5)
<223> OTHER INFORMATION: Xaa = Any Amino Acid
<220> FEATURE:
<221> NAME/KEY: MISC_FEATURE
<222> LOCATION: (7)..(7)
<223> OTHER INFORMATION: Xaa= Y or F
<220> FEATURE:
<221> NAME/KEY: MISC_FEATURE
<222> LOCATION: (9)..(9)
<223> OTHER INFORMATION: Xaa = Any Amino Acid

<400> SEQUENCE: 49

Asn Xaa Xaa Xaa Xaa Tyr Xaa Glu Xaa
1               5

<210> SEQ ID NO 50
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa = Y or F
<220> FEATURE:
<221> NAME/KEY: MISC_FEATURE
<222> LOCATION: (3)..(3)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (4)..(4)
<223> OTHER INFORMATION: Xaa = R, D, E, H, or K
<220> FEATURE:
<221> NAME/KEY: MISC_FEATURE
<222> LOCATION: (5)..(5)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (7)..(7)
<223> OTHER INFORMATION: Xaa = Y or F
<220> FEATURE:
<221> NAME/KEY: MISC_FEATURE
<222> LOCATION: (9)..(9)
<223> OTHER INFORMATION: Xaa = A, N, C, Q, G, I, L, M, F, P, S, T, W,
      or V

<400> SEQUENCE: 50

Asn Xaa Xaa Xaa Xaa Tyr Xaa Glu Xaa
1               5

<210> SEQ ID NO 51
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa = Y or F
```

```
<220> FEATURE:
<221> NAME/KEY: MISC_FEATURE
<222> LOCATION: (3)..(3)
<223> OTHER INFORMATION: Xaa = R, D, E, H, or K
<220> FEATURE:
<221> NAME/KEY: MISC_FEATURE
<222> LOCATION: (4)..(4)
<223> OTHER INFORMATION: Xaa = A, N, C, Q, G, I, L, M, F, P, S, T, W,
      or V
<220> FEATURE:
<221> NAME/KEY: MISC_FEATURE
<222> LOCATION: (5)..(5)
<223> OTHER INFORMATION: Xaa = R, D, E, H, or K
<220> FEATURE:
<221> NAME/KEY: MISC_FEATURE
<222> LOCATION: (7)..(7)
<223> OTHER INFORMATION: Xaa = Y or F
<220> FEATURE:
<221> NAME/KEY: MISC_FEATURE
<222> LOCATION: (9)..(9)
<223> OTHER INFORMATION: Xaa = A, N, C, Q, G, I, L, M, F, P, S, T, W,
      or V

<400> SEQUENCE: 51

Asn Xaa Xaa Xaa Xaa Tyr Xaa Glu Xaa
1               5

<210> SEQ ID NO 52
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa = Y or N
<220> FEATURE:
<221> NAME/KEY: MISC_FEATURE
<222> LOCATION: (2)..(2)
<223> OTHER INFORMATION: Xaa = H, F, W, or Y
<220> FEATURE:
<221> NAME/KEY: MISC_FEATURE
<222> LOCATION: (3)..(5)
<223> OTHER INFORMATION: Xaa = Any amino acid
<220> FEATURE:
<221> NAME/KEY: MISC_FEATURE
<222> LOCATION: (8)..(8)
<223> OTHER INFORMATION: Xaa = R, D, E, H, or K
<220> FEATURE:
<221> NAME/KEY: MISC_FEATURE
<222> LOCATION: (9)..(9)
<223> OTHER INFORMATION: Xaa = A, N, C, Q, G, I, L, M, F, P, S, T, W,
      or V

<400> SEQUENCE: 52

Xaa Xaa Xaa Xaa Xaa Tyr Tyr Xaa Xaa
1               5

<210> SEQ ID NO 53
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (2)..(2)
<223> OTHER INFORMATION: Xaa = R, D, E, H, or K
<220> FEATURE:
<221> NAME/KEY: MISC_FEATURE
<222> LOCATION: (3)..(5)
<223> OTHER INFORMATION: Xaa = Any amino acid
<220> FEATURE:
<221> NAME/KEY: MISC_FEATURE
```

```
<222> LOCATION: (7)..(9)
<223> OTHER INFORMATION: Xaa = A, N, C, Q, G, I, L, M, F, P, S, T, W,
      or V

<400> SEQUENCE: 53

Tyr Xaa Xaa Xaa Xaa Tyr Xaa Xaa Xaa
1               5

<210> SEQ ID NO 54
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa = R, D, E, H, K, N, C, Q, S, T, F, W, or Y
<220> FEATURE:
<221> NAME/KEY: MISC_FEATURE
<222> LOCATION: (2)..(2)
<223> OTHER INFORMATION: Xaa = H, F, W, or Y
<220> FEATURE:
<221> NAME/KEY: MISC_FEATURE
<222> LOCATION: (3)..(3)
<223> OTHER INFORMATION: Xaa = R, D, E, H, K, A, N, C, Q, G, I, L, M, F,
      P, S, T, W, or V
<220> FEATURE:
<221> NAME/KEY: MISC_FEATURE
<222> LOCATION: (4)..(4)
<223> OTHER INFORMATION: Xaa = R, D, E, H, or K
<220> FEATURE:
<221> NAME/KEY: MISC_FEATURE
<222> LOCATION: (5)..(5)
<223> OTHER INFORMATION: Xaa = R, D, E, H, K, A, N, C, Q, G, I, L, M, F,
      P, S, T, W, or V
<220> FEATURE:
<221> NAME/KEY: MISC_FEATURE
<222> LOCATION: (7)..(7)
<223> OTHER INFORMATION: Xaa = H, F, W, or Y
<220> FEATURE:
<221> NAME/KEY: MISC_FEATURE
<222> LOCATION: (8)..(8)
<223> OTHER INFORMATION: Xaa = R, D, E, H, or K
<220> FEATURE:
<221> NAME/KEY: MISC_FEATURE
<222> LOCATION: (9)..(9)
<223> OTHER INFORMATION: Xaa = A, N, C, Q, G, I, L, M, F, P, S, T, W,
      or V

<400> SEQUENCE: 54

Xaa Xaa Xaa Xaa Xaa Tyr Xaa Xaa Xaa
1               5

<210> SEQ ID NO 55
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa = R, D, E, H, K, N, C, Q, S, T, F, W, or Y
<220> FEATURE:
<221> NAME/KEY: MISC_FEATURE
<222> LOCATION: (2)..(2)
<223> OTHER INFORMATION: Xaa = F or Y
<220> FEATURE:
<221> NAME/KEY: MISC_FEATURE
<222> LOCATION: (3)..(3)
<223> OTHER INFORMATION: Xaa = R, D, E, H, K, A, N, C, Q, G, I, L, M, F,
      P, S, T, W, or V
<220> FEATURE:
<221> NAME/KEY: MISC_FEATURE
```

```
<222> LOCATION: (4)..(4)
<223> OTHER INFORMATION: Xaa = R or K
<220> FEATURE:
<221> NAME/KEY: MISC_FEATURE
<222> LOCATION: (5)..(5)
<223> OTHER INFORMATION: Xaa = R, D, E, H, K, A, N, C, Q, G, I, L, M, F,
      P, S, T, W, or V
<220> FEATURE:
<221> NAME/KEY: MISC_FEATURE
<222> LOCATION: (7)..(7)
<223> OTHER INFORMATION: Xaa = Y or F
<220> FEATURE:
<221> NAME/KEY: MISC_FEATURE
<222> LOCATION: (8)..(8)
<223> OTHER INFORMATION: Xaa = E or D

<400> SEQUENCE: 55

Xaa Xaa Xaa Xaa Xaa Tyr Xaa Xaa Val
1               5

<210> SEQ ID NO 56
<211> LENGTH: 9
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Xaa = H or N
<220> FEATURE:
<221> NAME/KEY: MISC_FEATURE
<222> LOCATION: (2)..(2)
<223> OTHER INFORMATION: Xaa = F or Y
<220> FEATURE:
<221> NAME/KEY: MISC_FEATURE
<222> LOCATION: (3)..(3)
<223> OTHER INFORMATION: Xaa = S or D
<220> FEATURE:
<221> NAME/KEY: MISC_FEATURE
<222> LOCATION: (4)..(4)
<223> OTHER INFORMATION: Xaa = R or K
<220> FEATURE:
<221> NAME/KEY: MISC_FEATURE
<222> LOCATION: (5)..(5)
<223> OTHER INFORMATION: Xaa = G or K
<220> FEATURE:
<221> NAME/KEY: MISC_FEATURE
<222> LOCATION: (7)..(7)
<223> OTHER INFORMATION: Xaa = Y or F

<400> SEQUENCE: 56

Xaa Xaa Xaa Xaa Xaa Tyr Xaa Asp Val
1               5

<210> SEQ ID NO 57
<211> LENGTH: 8
<212> TYPE: PRT
<213> ORGANISM: Artificial sequence
<220> FEATURE:
<223> OTHER INFORMATION: Synthesized

<400> SEQUENCE: 57

Asp Tyr Lys Asp Asp Asp Asp Lys
1               5
```

ANTIBODIES TO NON-FUNCTIONAL OLIGOMERIC P2X7 RECEPTORS AND METHODS OF USE THEREOF

CROSS-REFERENCE TO RELATED APPLICATION

The present application is a continuation of Ser. No. 13/518,382; filed Jun. 21, 2012, which is a national phase under 35 USC 371 of PCT/AU2010/001741, filed Dec. 23, 2010, which claims priority to AU 2009906286, filed Dec. 24, 2009.

REFERENCE TO SEQUENCE LISTING

This application includes an electronic sequence listing in a txt file named 450298_SEQLST.TXT created on Feb. 17, 2016 and containing 39,306 bytes, which is incorporated by reference.

FIELD OF THE INVENTION

The invention relates to purinergic receptors, to antibodies and related fragments thereof for binding to said receptors, to production of said antibodies and fragments and to use of said antibodies and fragments for cancer detection and therapy.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Purinergic (P2X) receptors are ATP-gated cation-selective channels. Each receptor is made up of three protein subunits or monomers. To date seven separate genes encoding P2X monomers have been identified: $P2X_1$, $P2X_2$, $P2X_3$, $P2X_4$, $P2X_5$, $P2X_6$, $P2X_7$.

$P2X_7$ receptors are of particular interest as the expression of these receptors is understood to be limited to cells having potential to undergo programmed cell death, such as thymocytes, dendritic cells, lymphocytes, macrophages and monocytes. There is some expression of $P2X_7$ receptors in normal homeostasis, such as on erythrocytes.

Interestingly, a $P2X_7$ receptor containing one or more monomers having a cis isomerisation at Pro210 (according to SEQ ID NO: 1) and which is devoid of ATP binding function has been found on cells that are understood to be unable to undergo programmed cell death, such as preneoplastic cells and neoplastic cells. This isoform of the receptor has been referred to as a "non functional" receptor.

Antibodies generated from immunisation with a peptide including Pro210 in cis bind to non functional $P2X_7$ receptors. However, they do not bind to $P2X_7$ receptors capable of binding ATP. Accordingly, these antibodies are useful for selectively detecting many forms of carcinoma and haemopoietic cancers and to treatment of some of these conditions.

WO02/057306A1 and WO03/020762A1 both discuss a probe for distinguishing between functional $P2X_7$ receptors and non functional $P2X_7$ receptors in the form of a monoclonal antibody.

To date it has been very difficult to obtain serological reagents that bind to non functional $P2X_7$ receptors on live cells with desirable affinity. Higher affinity reagents are generally desirable in applications for the detection and treatment of cancer.

There is a need for improved reagents for binding to $P2X_7$ receptors, particularly for new antibodies and fragments thereof that are capable of discriminating between ATP and non-ATP binding $P2X_7$ receptors on live cells. There is also a need for antibodies and fragments thereof that exhibit preferential binding to a $P2X_7$ receptor as it is expressed on live cells with reduced capacity to bind to a $P2X_7$ receptor once the target cell has died.

SUMMARY OF THE INVENTION

In one embodiment there is provided an antigen binding site for binding to a $P2X_7$ receptor, the antigen binding site being defined by general formula 1:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: (charged/polar/aromatic) (charged/aromatic)XXXY(aromatic/aliphatic)(charged/neutral)(neutral/aliphatic) (SEQ ID NO:48).
X throughout the specification represents any amino acid.

In one embodiment there is provided an antigen binding site for binding to a $P2X_7$ receptor, the antigen binding site being defined by general formula 2:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: N(Y/F)XXXY(Y/F)EX (SEQ ID NO:49).

In one embodiment there is provided an antigen binding site for binding to a $P2X_7$ receptor, the antigen binding site being defined by general formula 3:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: N(Y/F)(neutral)(charged)(neutral)Y(Y/F)E(neutral) (SEQ ID NO:50).

In one embodiment there is provided an antigen binding site for binding to a $P2X_7$ receptor, the antigen binding site being defined by general formula 4:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;

wherein:
CDR3 has an amino acid sequence of: NFLESYFEA (SEQ ID NO:7).

In one embodiment there is provided an antigen binding site for binding to a $P2X_7$ receptor, the antigen binding site being defined by general formula 5:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: N(Y/F)(charged)(neutral)(charged)Y(Y/F)E(neutral) (SEQ ID NO:51).

In one embodiment there is provided an antigen binding site for binding to a $P2X_7$ receptor, the antigen binding site being defined by general formula 6:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: NYRGDYYET (SEQ ID NO:8).

In one embodiment there is provided an antigen binding site for binding to a $P2X_7$ receptor, the antigen binding site being defined by general formula 7:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: H(aromatic)XXXYYNI (SEQ ID NO:42).

In one embodiment there is provided an antigen binding site for binding to a $P2X_7$ receptor, the antigen binding site being defined by general formula 8:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: H(Y/F)(neutral)(charged)(charged)YYNI (SEQ ID NO:43).

In one embodiment there is provided an antigen binding site for binding to a $P2X_7$ receptor, the antigen binding site being defined by general formula 9:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: H(Y/F)(neutral)(charged)(neutral)YYNI (SEQ ID NO:44).

In one embodiment there is provided an antigen binding site for binding to a $P2X_7$ receptor, the antigen binding site being defined by general formula 10:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: HYSKEYYNI (SEQ ID NO:9).

In one embodiment there is provided an antigen binding site for binding to a $P2X_7$ receptor, the antigen binding site being defined by general formula 11:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: HFQRGYYNI (SEQ ID NO:10).

In one embodiment there is provided an antigen binding site for binding to a $P2X_7$ receptor, the antigen binding site being defined by general formula 12:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: (Y/N)(aromatic)XXXYY(charged)(neutral) (SEQ ID NO:52).

In one embodiment there is provided an antigen binding site for binding to a $P2X_7$ receptor, the antigen binding site being defined by general formula 13:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: (Y/N)(aromatic)(neutral)(neutral)(neutral)YYDV (SEQ ID NO:45).

In one embodiment there is provided an antigen binding site for binding to a $P2X_7$ receptor, the antigen binding site being defined by general formula 14:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: (Y/N)(aromatic)(neutral)(neutral)(neutral)YYEV (SEQ ID NO:46).

In one embodiment there is provided an antigen binding site for binding to a $P2X_7$ receptor, the antigen binding site being defined by general formula 15:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;

wherein:
CDR3 has an amino acid sequence of: YFPLVYYDV (SEQ ID NO:11).

In one embodiment there is provided an antigen binding site for binding to a P2X$_7$ receptor, the antigen binding site being defined by general formula 16:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: NYLPMYYEV (SEQ ID NO:12).

In one embodiment there is provided an antigen binding site for binding to a P2X$_7$ receptor, the antigen binding site being defined by general formula 17:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: Y(charged)XXXY(neutral)(neutral)(neutral) (SEQ ID NO:53).

In one embodiment there is provided an antigen binding site for binding to a P2X$_7$ receptor, the antigen binding site being defined by general formula 18:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: YHVIQYLGP (SEQ ID NO:19).

In one embodiment there is provided an antigen binding site for binding to a P2X$_7$ receptor, the antigen binding site being defined by general formula 19:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence selected from the group consisting of: HYSSRFFDV (SEQ ID NO:34), NFKLMYYNV (SEQ ID NO:13), NYRGDYYET (SEQ ID NO:8), HFSRGYYDV (SEQ ID NO:14), NFLESYFEA (SEQ ID NO:7), NYLPMYYEV (SEQ ID NO:12), HYIKVYYEA (SEQ ID NO:15), HYSSRFFEV (SEQ ID NO:16), NFRVMFFKA (SEQ ID NO:17), HFQRGYYNI (SEQ ID NO:10), HYSSRFFEV (SEQ ID NO:16), YHVIQYLGP (SEQ ID NO:19), HYSKEYYNI (SEQ ID NO:9), YFPLVYYDV (SEQ ID NO:11), DFTVPFYNA (SEQ ID NO:20), NYDKKYFDV (SEQ ID NO:21), YFPLVYYDV (SEQ ID NO:11).

In one embodiment there is provided an antigen binding site for binding to a P2X$_7$ receptor, the antigen binding site being defined by general formula 20:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has an amino acid sequence of KASQNVGTNVA (SEQ ID NO:5).
CDR3 has an amino acid sequence of any previous embodiment describing a CDR3 sequence.

In one embodiment there is provided an antigen binding site for binding to a P2X$_7$ receptor, the antigen binding site being defined by general formula 21:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has an amino acid sequence of SYYMS (SEQ ID NO:23).
CDR3 has an amino acid sequence of any previous embodiment describing a CDR3 sequence.

In one embodiment there is provided an antigen binding site for binding to a P2X$_7$ receptor, the antigen binding site being defined by general formula 22:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR2 has an amino acid sequence of SASFRYS (SEQ ID NO:6).
CDR3 has an amino acid sequence of any previous embodiment describing a CDR3 sequence.

In one embodiment there is provided an antigen binding site for binding to a P2X$_7$ receptor, the antigen binding site being defined by general formula 23:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR2 has an amino acid sequence of AINSNGGSTYYPDTVKG (SEQ ID NO:24).
CDR3 has an amino acid sequence of any previous embodiment describing a CDR3 sequence.

In one embodiment there is provided an antigen binding site for binding to a P2X$_7$ receptor, the antigen binding site being defined by general formula 24:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has an amino acid sequence of KASQNVGTNVA (SEQ ID NO:5)
CDR2 has an amino acid sequence of SASFRYS (SEQ ID NO:6)
CDR3 has an amino acid sequence of any previous embodiment describing a CDR3 sequence.

In one embodiment there is provided an antigen binding site for binding to a P2X$_7$ receptor, the antigen binding site being defined by general formula 25:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has an amino acid sequence of SYYMS (SEQ ID NO:23)
CDR2 has an amino acid sequence of AINSNGGSTYYP-DTVKG (SEQ ID NO:24)
CDR3 has an amino acid sequence of any previous embodiment describing a CDR3 sequence.

In one embodiment there is provided an antigen binding site according to any embodiment described above wherein FR1 is either MADIVMTQSQKFMSTSVGDRVSVTC (SEQ ID NO:25) or DVKLVESGGGLVKLGGSLKLS-CAASGFTFS (SEQ ID NO:29).

In one embodiment there is provided an antigen binding site according to any embodiment described above wherein FR2 is either WYQQKPGQSPKALIY (SEQ ID NO:26) or WVRQTPEKRLELVA (SEQ ID NO:30).

In one embodiment there is provided an antigen binding site according to any embodiment described above wherein FR3 is either GVPDRFTGSGSGTDFTLTISNVQSEDLA-EFFC (SEQ ID NO:27) or RFTISRDNAKNTLYLQMSS-LKSEDTAFYYCTR (SEQ ID NO:31).

In one embodiment there is provided an antigen binding site according to any embodiment described above wherein FR4 is either FGSGTRLEIK (SEQ ID NO:28) or WGAGT-TVTVSS (SEQ ID NO:32).

In one embodiment there is provided an antigen binding site for binding to a P2X$_7$ receptor, the antigen binding site being defined by general formula 26:

FR1-CDR1-FR2-CDR2-FR3-CDR3-FR4-linker-
   FR1a-CDR1a-FR2a-CDR2a-FR3a-CDR3a-FR4a wherein:
FR1, FR2, FR3, FR4, FR1a, FR2a, FR3a and FR4a are each framework regions;
CDR1, CDR2, CDR3, CDR1a, CDR2a, CDR3a are each complementarity determining regions;
  wherein:
CDR1 has an amino acid sequence of KASQNVGTNVA (SEQ ID NO:5)
CDR2 has an amino acid sequence of SASFRYS (SEQ ID NO:6)
CDR3 has an amino acid sequence of any previous embodiment describing a CDR3 sequence or QQYNSYPFT (SEQ ID NO:33).
CDR1a has an amino acid sequence of SYYMS (SEQ ID NO:23)
CDR2a has an amino acid sequence of AINSNGGSTYYP-DTVKG (SEQ ID NO:24)
CDR3a has an amino acid sequence of any previous embodiment describing a CDR3 sequence or QQYNSYPFT (SEQ ID NO: 33) when CDR3 is an amino acid sequence of any previous embodiment describing a CDR3 sequence
FR1 has an amino acid sequence of MADIVMTQSQKF-MSTSVGDRVSVTC (SEQ ID NO: 25)
FR2 has an amino acid sequence of WYQQKPGQSPKA-LIY (SEQ ID NO: 26)
FR3 has an amino acid sequence of GVPDRFTGSGSGTD-FTLTISNVQSEDLAEFFC (SEQ ID NO: 27)

FR4 has an amino acid sequence of FGSGTRLEIK (SEQ ID NO: 28)
FR1a has an amino acid sequence of DVKLVES-GGGLVKLGGSLKLSCAASGFTFS (SEQ ID NO: 29)
FR2a has an amino acid sequence of WVRQTPEKRLELVA (SEQ ID NO: 30)
FR3a has an amino acid sequence of RFTISRDNAKNT-LYLQMSSLKSEDTAFYYCTR (SEQ ID NO: 31)
FR4a has an amino acid sequence of WGAGTTVTVSS (SEQ ID NO: 32).

In one embodiment there is provided an antigen binding site for binding to a P2X$_7$ receptor, the antigen binding site being defined by general formula 27:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: (charged/polar/aromatic)(aromatic)(charged/neutral)(charged)(charged/neutral)Y(aromatic)(charged)(neutral) (SEQ ID NO:54).

In one embodiment there is provided an antigen binding site for binding to a P2X$_7$ receptor, the antigen binding site being defined by general formula 28:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: (charged/polar/aromatic)(F/Y)(charged/neutral)(R/K)(charged/neutral)(Y)(Y/F)(E/D)V (SEQ ID NO:55).

In one embodiment there is provided an antigen binding site for binding to a P2X$_7$ receptor, the antigen binding site being defined by general formula 30:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR3 has an amino acid sequence of: (H/N)(F/Y)(S/D)(R/K)(G/K)Y(Y/F)DV (SEQ ID NO:56).

In one embodiment the linker of general formula 26 has an amino acid sequence of 15 amino acid residues. Typically, the linker comprises predominately glycine and serine residues. Preferably, the linker is GGGGSGGGGSGGGGS (SEQ ID NO:47).

In one embodiment, the antigen binding site of the invention has a CDR3 amino acid sequence that comprises HFSRGYYDV (SEQ ID NO:14) or NYDKKYFDV (SEQ ID NO:21).

In one embodiment, the antigen binding site of the invention has a CDR3 amino acid sequence that consists of HFSRGYYDV SEQ ID NO:14) or NYDKKYFDV (SEQ ID NO:21).

In other embodiments there is provided an antigen binding site having a sequence as described herein, or including a CDR and/or FR sequence as described herein and including one or more mutations for increasing the affinity of said site for binding to a P2X$_7$ receptor.

In another embodiment there is provided an antigen binding site as described herein wherein an amino acid sequence forming one or more of FR1, CDR1, FR2, CDR2, FR3, CDR3 and FR4 is a human sequence.

In another embodiment there is provided an antigen binding site as described herein wherein an amino acid sequence forming one or more of FR1, CDR1, FR2, CDR2, FR3, CDR3 and FR4 is a canine or feline sequence.

The antigen binding site may be engineered to have sequences from a particular animal, for example it may be chimeric (i.e. containing some but not all sequences found in the individual that receives the antibody). Alternatively, it may consist of allogeneic or syngeneic sequences. An example of the latter is a dog antibody for use in treatment of a dog.

The animal from which the antibody is derived may include a domestic, companion or farm animal, including dogs, cats, cows, pigs, horses and sheep.

In another embodiment there is provided an anti $P2X_7$ receptor immunoglobulin variable domain, antibody, Fab, dab, scFv including an antigen binding site having a sequence as described herein, or including a CDR and/or FR sequence as described herein.

In another embodiment there is provided a diabody or triabody including an antigen binding site having a sequence as described herein, or including a CDR and/or FR sequence as described herein.

In another embodiment there is provided a fusion protein including an antigen binding site, immunoglobulin variable domain, antibody, Fab, dab, scFv, diabody or triabody as described herein.

In another embodiment there is provided a conjugate in the form of an antigen binding site, immunoglobulin variable domain, antibody, Fab, dab, scFv, diabody, triabody or fusion protein as described herein conjugated to a label or a cytotoxic agent.

In another embodiment there is provided an antibody for binding to an antigen binding site of an immunoglobulin variable domain, antibody, Fab, dab, scFv, diabody, triabody, fusion protein, or conjugate as described herein.

In another embodiment there is provided a nucleic acid encoding an antigen binding site, or a CDR and/or FR sequence as described herein, or an immunoglobulin variable domain, antibody, Fab, dab, scFv, diabody, triabody, fusion protein or conjugate as described herein.

In another embodiment there is provided a vector including a nucleic acid described herein.

In another embodiment there is provided a cell including a vector or nucleic acid described herein.

In another embodiment there is provided an animal or tissue derived therefrom including a cell described herein.

In another embodiment there is provided a pharmaceutical composition including an antigen binding site, or including a CDR and/or FR sequence as described herein, or an immunoglobulin variable domain, antibody, Fab, dab, scFv, diabody, triabody, fusion protein, or conjugate as described herein and a pharmaceutically acceptable carrier, diluent or excipient.

In another embodiment there is provided a diagnostic composition including an antigen binding site, or including a CDR and/or FR sequence as described herein, or an immunoglobulin variable domain, antibody, Fab, dab, scFv, diabody, triabody, fusion protein or conjugate as described herein, a diluent and optionally a label.

In another embodiment there is provided a kit or article of manufacture including an antigen binding site, or including a CDR and/or FR sequence as described herein or an immunoglobulin variable domain, antibody, Fab, dab, scFv, diabody, triabody, fusion protein or conjugate as described herein.

In another embodiment there is provided a use of a sequence according to one or more of CDR1, CDR2, FR1, FR2, FR3 and FR4 as described herein to produce an antigen binding site for binding to a $P2X_7$ receptor.

In another embodiment there is provided a use of an antigen binding site or a CDR and/or FR sequence as described herein to produce an anti $P2X_7$ receptor antigen binding site having increased affinity for $P2X_7$ receptor.

In another embodiment there is provided a library of nucleic acid molecules produced from the mutation of an antigen binding site or a CDR and/or FR sequence as described herein, wherein at least one nucleic acid molecule in said library encodes an antigen binding site for binding to an a $P2X_7$ receptor.

In another embodiment there is provided a method for producing an anti $P2X_7$ antigen binding site as described herein including expressing a nucleic acid as described herein in a cell or animal as described herein.

In another embodiment there is provided a method for the treatment of cancer or a condition or disease associated with expression of non functional $P2X_7$ receptor in an individual including the step of providing an antigen binding site, immunoglobulin variable domain, antibody, Fab, dab, scFv, diabody, triabody, fusion protein, conjugate or pharmaceutical composition as described herein to an individual requiring treatment for cancer or said condition or disease.

In another embodiment there is provided a use of an antigen binding site, immunoglobulin variable domain, antibody, Fab, dab, scFv, diabody, triabody, fusion protein, conjugate or pharmaceutical composition as described herein in the manufacture of a medicament for the treatment of cancer or a condition or disease associated with expression of non functional $P2X_7$ receptor.

In another embodiment there is provided an antigen binding site, immunoglobulin variable domain, antibody, Fab, dab, scFv, diabody, triabody, fusion protein, conjugate or pharmaceutical composition as described herein for the treatment of cancer or a condition or disease associated with expression of non functional $P2X_7$ receptor.

In another embodiment there is provided a method for the diagnosis of cancer or disease or condition associated with expression of non functional $P2X_7$ receptor, including the step of contacting tissues or cells for which the presence or absence of cancer is to be determined with a reagent in the form of an antigen binding site, immunoglobulin variable domain, antibody, Fab, dab, scFv, diabody, triabody, fusion protein, conjugate or diagnostic composition as described herein and detecting for the binding of the reagent with the tissues or cells. The method may be operated in vivo or in vitro.

Typically the antigen binding sites according to the invention bind to non functional $P2X_7$ receptors, especially receptors wherein Pro210 of $P2X_7$ is in cis conformation. In certain embodiments the antigen binding sites according to the invention do not bind to functional $P2X_7$ receptors, especially receptors wherein Pro210 of $P2X_7$ is in trans conformation.

Typically the antigen binding sites according to the invention bind to non functional $P2X_7$ receptors on live cells. In some embodiments, the antigen binding sites do not bind, or bind with very low or undetectable affinity to non functional receptors on dead or dying cells. Whether an antigen binding site of the invention does or does not bind to a $P2X_7$ receptor can be determined using standard methods known in the art.

In one embodiment, the antigen binding sites according to the invention bind to P2X$_7$ receptors on live cells with affinities ($K_D$) in the range of about 1 pM to about 1 uM. Typically, when the antigen binding site is part of an IgM the affinity for P2X$_7$ receptors on live cells is between about 1 pM to about 1 nM, preferably about 1 pM to about 50 pM. Typically, when the antigen binding site is part of an IgG the affinity for P2X$_7$ receptors on live cells is between about 1 pM to about 1 nM, preferably between about 1 pM to about 100 pM. Typically, when the antigen binding site is part of an Fab the affinity for P2X$_7$ receptors on live cells is between about 100 pM to about 100 nM, preferably about 1 nM to about 100 nM. Typically, when the antigen binding site is part of an scFV the affinity for P2X$_7$ receptors on live cells is between about 10 nM to about 1 uM, preferably about 10 nM to about 100 nM. Typically, when the antigen binding site is part of an dab the affinity for P2X$_7$ receptors on live cells is between about 10 nM to about 10 uM, preferably about 100 nM to about 1 uM.

In certain embodiments, the antigen binding sites of the invention and molecules comprising same are capable of inducing apoptosis.

In certain embodiments, the antigen binding sites of the invention and molecules comprising same are capable of inducing caspase activation.

BRIEF DESCRIPTION OF THE DRAWINGS

FIG. 1. Full length human P2X$_7$ receptor (SEQ ID NO: 1).

FIG. 2. An extracellular domain sequence of P2X$_7$ receptor. P2X$_7$ receptor (47-306) (SEQ ID NO: 2) (ECD2) is amino acids 47 to 306 of SEQ ID NO: 1. The amino acids struck-through designate amino acids that are deleted from the full length P2X$_7$ receptor sequence.

FIG. 3. An extracellular domain sequence of P2X$_7$ receptor. P2X$_7$ receptor (47-332) (SEQ ID NO:3) (ECD1) is amino acids 47 to 332 of SEQ ID NO: 1. The amino acids struck-through designate amino acids that are deleted from the full length P2X$_7$ receptor sequence.

FIGS. 6A-B. (A) 2F6 scFv sequence with His tag added for detection (SEQ ID NO: 4). The 2F6 scFV sequence shown has the following organisational structure (in order from N-terminus to C-terminus) FR1-CDR1-FR2-CDR2-FR3-CDR3-FR4-linker-FR1a-CDR1a-FR2a-CDR2a-FR3a-CDR3a-FR4a-AAA-Flag® epitope tag (DYKDDDDK) (SEQ ID NO:57)-AAA-His tag. (B) Purification of recombinant 2F6 IgG$_{2a}$ by size exclusion HPLC. The recombinant IgG2a was separated by HPLC and an example HPLC chromatogram is shown.

FIG. 17. Affinity Maturation of CDR3 Sequences from 2F6. The amino acid sequences of affinity matured scFv/Fab derivatives listed as mutant clones with the wildtype (WT) 2F6 CDR3 sequence at the top of the list.

DETAILED DESCRIPTION OF THE EMBODIMENTS

Figure 4:
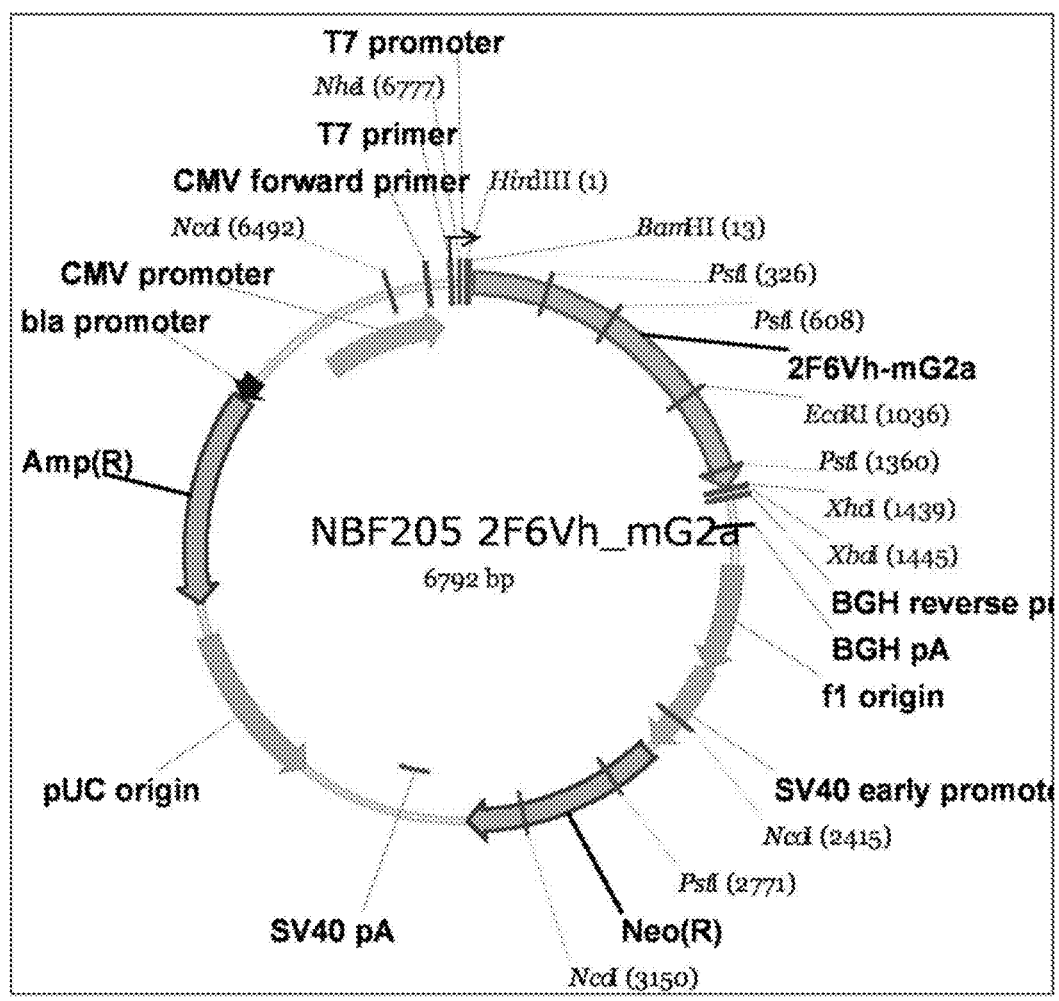
FIG. 4. Expression vector structure for 2F6 V$_H$.
Figure 5:
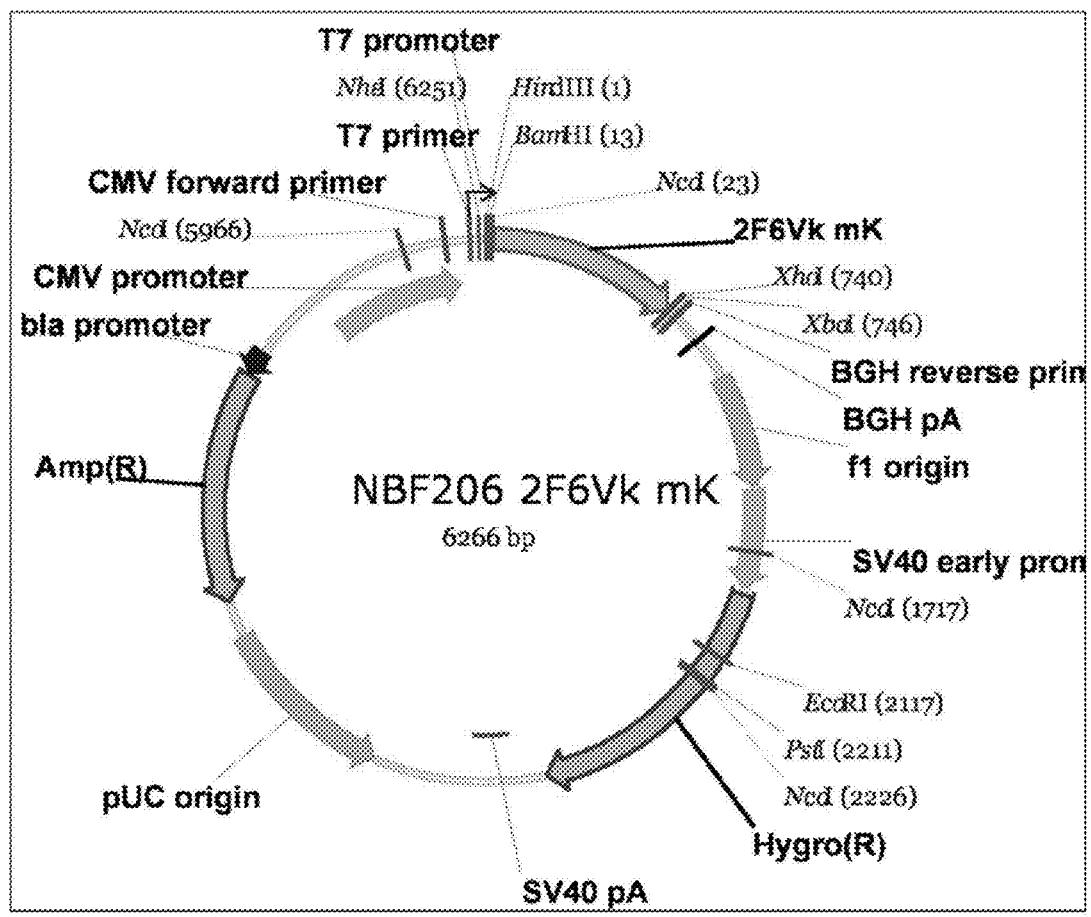
FIG. 5. Expression vector structure for 2F6 V$_L$.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

The invention provides antigen binding sites that are capable of binding to non-functional $P2X_7$ receptors expressed by live cells. These receptors are in a higher order oligomeric form. This oligomeric form is two or more $P2X_7$ receptor monomers that have associated. Typically, the oligomeric form is a trimer of three $P2X_7$ receptor monomers. One advantage of the antigen binding sites of the invention which bind higher order oligomeric $P2X_7$ forms is that sequestration by monomeric forms of the $P2X_7$ receptor liberated from lysed or apoptotic cells will be reduced compared to antibodies that only bind monomeric $P2X_7$ receptors.

For purposes of interpreting this specification, the following definitions will apply and whenever appropriate, terms used in the singular will also include the plural and vice versa. In the event that any definition set forth conflicts with any document incorporated herein by reference, the definition set forth below shall prevail.

"Purinergic receptor" generally refers to a receptor that uses a purine (such as ATP) as a ligand.

"$P2X_7$ receptor" generally refers to a purinergic receptor formed from three protein subunits or monomers, with at least one of the monomers having an amino acid sequence substantially as shown in SEQ ID NO:1 (see FIG. 1). "$P2X_7$ receptor" may be a functional or non functional receptor as described below. "$P2X_7$ receptor" encompasses naturally occurring variants of $P2X_7$ receptor, e.g., wherein the $P2X_7$ monomers are splice variants, allelic variants and isoforms including naturally-occurring truncated or secreted forms of the monomers forming the $P2X_7$ receptor (e.g., a form consisting of the extracellular domain sequence or truncated form of it), naturally-occurring variant forms (e.g., alternatively spliced forms) and naturally-occurring allelic variants. In certain embodiments of the invention, the native sequence $P2X_7$ monomeric polypeptides disclosed herein are mature or full-length native sequence polypeptides comprising the full-length amino acids sequence shown in SEQ ID NO:1. In certain embodiments the $P2X_7$ receptor may have an amino acid sequence that is modified, for example various of the amino acids in the sequence shown in SEQ ID NO:1 may be substituted, deleted, or a residue may be inserted.

"Functional $P2X_7$ receptor" generally refers to a form of the $P2X_7$ receptor having a binding site or cleft for binding to ATP. When bound to ATP, the receptor forms a pore-like structure that enables the ingress of calcium ions into the cytosol, one consequence of which may be programmed cell death. In normal homeostasis, expression of functional $P2X_7$ receptors is generally limited to cells that undergo programmed cell death such as thymocytes, dendritic cells, lymphocytes, macrophages and monocytes. There may also be some expression of functional $P2X_7$ receptors on erythrocytes.

"Non functional $P2X_7$ receptor" generally refers to a form of a $P2X_7$ receptor in which one or more of the monomers has a cis isomerisation at Pro210 (according to SEQ ID NO:1). The isomerisation may arise from any molecular event that leads to misfolding of the monomer, including for example, mutation of monomer primary sequence or abnormal post translational processing. One consequence of the isomerisation is that the receptor is unable to bind to ATP. In the circumstances, the receptor cannot form a pore and this limits the extent to which calcium ions may enter the cytosol. Non functional P2X$_7$ receptors are expressed on a wide range of epithelial and haematopoietic cancers.

"Extracellular domain" (ECD) used herein are P2X$_7$ receptor (47-306) (SEQ ID NO: 2, see FIG. 2) (ECD2) and P2X$_7$ receptor (47-332) (SEQ ID NO:3) (ECD1). P2X$_7$ receptor (47-306) (SEQ ID NO: 2) is amino acids 47 to 306 of SEQ ID NO: 1. P2X$_7$ receptor (47-332) (SEQ ID NO:3, see FIG. 3) is amino acids 47 to 332 of SEQ ID NO: 1.

"Antibodies" or "immunoglobulins" or "Igs" are gamma globulin proteins that are found in blood, or other bodily fluids of vertebrates that function in the immune system to bind antigen, hence identifying and neutralizing foreign objects.

Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intrachain disulfide bridges.

H and L chains define specific Ig domains. More particularly, each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H$1).

Antibodies can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2. The L chain from any vertebrate species can be assigned to one of two clearly distinct types, called kappa and lambda, based on the amino acid sequences of their constant domains.

The constant domain includes the Fc portion which comprises the carboxy-terminal portions of both H chains held together by disulfides. The effector functions of antibodies such as ADCC are determined by sequences in the Fc region, which region is also the part recognized by Fc receptors (FcR) found on certain types of cells.

The pairing of a $V_H$ and $V_L$ together forms a "variable region" or "variable domain" including the amino-terminal domains of the heavy or light chain of the antibody. The variable domain of the heavy chain may be referred to as "VH." The variable domain of the light chain may be referred to as "VL." The V domain contains an antigen binding site which affects antigen binding and defines specificity of a particular antibody for its particular antigen. V regions span about 110 amino acid residues and consist of relatively invariant stretches called framework regions (FRs) (generally about 4) of 15-30 amino acids separated by shorter regions of extreme variability called "hypervariable regions" (generally about 3) that are each 9-12 amino acids long. The FRs largely adopt a β-sheet configuration and the hypervariable regions form loops connecting, and in some cases forming part of, the β-sheet structure.

"Hypervariable region", "HVR", or "HV" refers to the regions of an antibody variable domain which are hypervariable in sequence and/or form structurally defined loops. Generally, antibodies comprise six hypervariable regions; three in the VH (HI, H2, H3), and three in the VL (LI, L2, L3). A number of hypervariable region delineations are in use and are encompassed herein. The Kabat Complementarity Determining Regions (CDRs) are based on sequence variability and are the most commonly used (Kabat et al, Sequences of Proteins of Immunological Interest, 5th Ed. Public Health Service, National Institutes of Health, Bethesda, Md. (1991)).

"Framework" or "FR" residues are those variable domain residues other than the hypervariable region residues herein defined.

"A peptide for forming an antigen binding site" generally refers to a peptide that may form a conformation that confers the specificity of an antigen for antigen. Examples include whole antibody or whole antibody related structures, whole antibody fragments including a variable domain, variable domains and fragments thereof, including light and heavy chains, or fragments of light and heavy chains that include some but not all of hypervariable regions or constant regions.

An "intact" or "whole" antibody is one which comprises an antigen-binding site as well as a $C_L$ and at least heavy chain constant domains, $C_H$1, $C_H$2 and $C_H$3. The constant domains may be native sequence constant domains (e.g. human native sequence constant domains) or amino acid sequence variant thereof.

"Whole antibody related structures" include multimerized forms of whole antibody.

"Whole antibody fragments including a variable domain" include Fab, Fab', F(ab')$_2$, and Fv fragments; diabodies; linear antibodies, single-chain antibody molecules; and multispecific antibodies formed from antibody fragments.

The Fab fragment consists of an entire L chain along with the variable region domain of the H chain ($V_H$), and the first constant domain of one heavy chain ($C_H$1). Each Fab fragment is monovalent with respect to antigen binding, i.e., it has a single antigen-binding site.

A Fab' fragment differs from Fab fragments by having additional few residues at the carboxy terminus of the $C_H$1 domain including one or more cysteines from the antibody hinge region. Fab'-SH is the designation herein for Fab' in which the cysteine residue(s) of the constant domains bear a free thiol group.

A F(ab')$_2$ fragment roughly corresponds to two disulfide linked Fab fragments having divalent antigen-binding activity and is still capable of cross-linking antigen.

An "FV" is the minimum antibody fragment which contains a complete antigen-recognition and -binding site. This fragment consists of a dimer of one heavy- and one light-chain variable region domain in tight, non-covalent association.

In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFV" or "scFv" are antibody fragments that comprise the $V_H$ and $V_L$ antibody domains connected to form a single polypeptide chain. Preferably, the scFv polypeptide further comprises a polypeptide linker between the $V_H$ and $V_L$ domains which enables the scFv to form the desired structure for antigen binding.

A "single variable domain" is half of an Fv (comprising only three CDRs specific for an antigen) that has the ability to recognize and bind antigen, although at a lower affinity than the entire binding site "Diabodies" refers to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments (see preceding paragraph) with short linkers (about 5-10 residues) between the $V_H$ and $V_L$ domains such that interchain but not intra-chain pairing of the V domains is achieved, resulting in a bivalent fragment, i.e., fragment having two antigen-binding sites.

Diabodies may be bivalent or bispecific. Bispecific diabodies are heterodimers of two "crossover" sFv fragments in which the $V_H$ and $V_L$ domains of the two antibodies are present on different polypeptide chains. Triabodies and tetrabodies are also generally know in the art.

An "isolated antibody" is one which has been identified and separated and/or recovered from a component of its pre-existing environment. Contaminant components are materials that would interfere with therapeutic uses for the antibody, and may include enzymes, hormones, and other proteinaceous or nonproteinaceous solutes.

A "human antibody" refers to an antibody which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Human antibodies can be prepared by administering the antigen to a transgenic animal that has been modified to produce such antibodies in response to antigenic challenge, but whose endogenous loci have been disabled.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit, dog, cat or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

"Monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology, or may be made using recombinant DNA methods in bacterial, eukaryotic animal or plant cells. The "monoclonal antibodies" may also be isolated from phage antibody libraries.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Chimeric antibodies of interest herein include "primatized" antibodies comprising variable domain antigen-binding sequences derived from a non-human primate (e.g. Old World Monkey, Ape etc), and human constant region sequences.

The term "anti-P2X$_7$ receptor antibody" or "an antibody that binds to P2X$_7$ receptor" refers to an antibody that is capable of binding P2X$_7$ receptor with sufficient affinity such that the antibody is useful as a diagnostic and/or therapeutic agent in targeting P2X$_7$ receptor, typically non functional P2X$_7$ receptor. Preferably, the extent of binding of an P2X$_7$ receptor antibody to an unrelated receptor protein is less than about 10% of the binding of the antibody to P2X$_7$ receptor as measured, e.g., by a radioimmunoassay (RIA). In certain embodiments, an antibody that binds to P2X$_7$ receptor has a dissociation constant (Kd) of <1 µM, <100 nM, <10 nM, <1 nM, or <0.1 nM. An anti non functional P2X$_7$ receptor antibody is generally one having some or all of these serological characteristics and that binds to non functional P2X$_7$ receptors but not to functional P2X$_7$ receptors.

An "affinity matured" antibody is one with one or more alterations in one or more HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art.

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

"Binding affinity" generally refers to the strength of the sum total of noncovalent interactions between a single binding site of a molecule (e.g., an antibody) and its binding partner (e.g., an antigen). Generally, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

As used herein, the properties of amino acids are defined in the following table:

| Amino Acid | 3-letter code | 1-letter code | Properties |
|---|---|---|---|
| Alanine | Ala | A | aliphatic hydrophobic neutral |
| Arginine | Arg | R | polar hydrophilic charged (+) |
| Asparagine | Asn | N | polar hydrophilic neutral |
| Aspartate | Asp | D | polar hydrophilic charged (−) |
| Cysteine | Cys | C | polar hydrophobic neutral |
| Glutamine | Gln | Q | polar hydrophilic neutral |
| Glutamate | Glu | E | polar hydrophilic charged (−) |
| Glycine | Gly | G | aliphatic neutral |
| Histidine | His | H | aromatic polar hydrophilic charged (+) |
| Isoleucine | Ile | I | aliphatic hydrophobic neutral |
| Leucine | Leu | L | aliphatic hydrophobic neutral |
| Lysine | Lys | K | polar hydrophilic charged (+) |
| Methionine | Met | M | hydrophobic neutral |
| Phenylalanine | Phe | F | aromatic hydrophobic neutral |
| Proline | Pro | P | hydrophobic neutral |
| Serine | Ser | S | polar hydrophilic neutral |
| Threonine | Thr | T | polar hydrophilic neutral |
| Tryptophan | Trp | W | aromatic hydrophobic neutral |
| Tyrosine | Tyr | Y | aromatic polar hydrophobic |
| Valine | Val | V | aliphatic hydrophobic neutral |

The inventors have determined the CDR sequences of a number of variable domain clones that they have found to bind to non-functional P2X$_7$ receptor. These CDR sequences are shown in Table 1a below.

In one embodiment there is provided a peptide having a sequence as shown in Table 1a or b. These peptides are particularly useful for constructing antigen binding sites, variable domains, antibodies and related fragments.

TABLE 1a

| CDR sequences | | |
|---|---|---|
| CDR1 | CDR2 | CDR3 |
| KASQNVGTNVA<br>(SEQ ID NO: 5) | SASFRYS<br>(SEQ ID NO: 6) | (charged/polar/aromatic) (charged/aromatic)<br>XXXY (aromatic/aliphatic)(charged/neutral)<br>(neutral/aliphatic)<br>N(Y/F)XXXY(Y/F)EX<br>N(Y/F)(neutral)(charged)(neutral)Y(Y/F)E(neutral)<br>NFLESYFEA<br>(SEQ ID NO: 7)<br>N(Y/F)(charged)(neutral)(charged)Y(Y/F)E(neutral)<br>NYRGDYYET<br>(SEQ ID NO: 8)<br>H(aromatic)XXXYYNI<br>H(Y/F)(neutral)(charged)(neutral)YYNI<br>H(Y/F)(neutral)(charged)(charged)YYNI<br>HYSKEYYNI<br>(SEQ ID NO: 9)<br>HFQRGYYNI<br>(SEQ ID NO: 10)<br>(Y/N)(aromatic)XXXYY(charged)(neutral)<br>(Y/N)(aromatic)(neutral)(neutral)(neutral)YYDV<br>(Y/N)(aromatic)(neutral)(neutral)(neutral)YYEV<br>YFPLVYYDV<br>(SEQ ID NO: 11)<br>NYLPMYYEV<br>(SEQ ID NO: 12)<br>Y(charged)XXXY(neutral)(neutral)(neutral)<br>NFKLMYYNV<br>(SEQ ID NO: 13)<br>(charged/polar/aromatic)(aromatic)(charged/neutral)<br>(charged)(charged/neutral)Y(aromatic)(charged)<br>(neutral)<br>(charged/polar/aromatic)(F/Y)(charged/neutral)(R/K)<br>(charged/neutral)(Y)(Y/F)(E/D)V<br>(H/N)(F/Y)(S/D)(R/K)(G/K)Y(Y/F)DV<br>HFSRGYYDV<br>(SEQ ID NO: 14)<br>HYIKVYYEA<br>(SEQ ID NO: 15)<br>HYSSRFFEV<br>(SEQ ID NO: 16)<br>NFRVMFFKA |

TABLE 1a-continued

CDR sequences

| CDR1 | CDR2 | CDR3 |
|---|---|---|
| | | (SEQ ID NO: 17)<br>HYSSRFFEV<br>(SEQ ID NO: 18)<br>YHVIQYLGP<br>(SEQ ID NO: 19)<br>DFTVPFYNA<br>(SEQ ID NO: 20)<br>NYDKKYFDV<br>(SEQ ID NO: 21)<br>YFPLVYYDV<br>(SEQ ID NO: 22)<br>HYSSRFFDV<br>(SEQ ID NO: 34) |
| SYYMS<br>(SEQ ID NO: 23) | AINSNGGS<br>YYPTVKG<br>(SEQ ID NO: 24) | (charged/polar/aromatic) (charged/aromatic)<br>XXXY (aromatic/aliphatic) (charged/neutral)<br>(neutral/aliphatic)<br>N(Y/F)XXXXY(Y/F)EX<br>N(Y/F) (neutral) (charged) (neutral)Y(Y/F)E(neutral)<br>NFLESYFEA<br>N(Y/F) (charged) (neutral) (charged)Y(Y/F)E(neutral)<br>NYRGDYYET<br>H(aromatic)XXXYYNI<br>H(Y/F) (neutral) (charged) (neutral)YYNI<br>H(Y/F) (neutral) (charged) (charged)YYNI<br>HYSKEYYNI<br>HFQRGYYNI<br>(Y/N) (aromatic)XXXXYY(charged) (neutral)<br>(Y/N) (aromatic) (neutral) (neutral) (neutral)YYDV<br>(Y/N) (aromatic) (neutral) (neutral) (neutral)YYEV<br>YFPLVYYDV<br>NYLPMYYEV<br>Y(charged)XXXY(neutral) (neutral) (neutral)<br>YHVIQYLGP<br>NFKLMYYNV<br>(charged/polar/aromatic) (aromatic) (charged/neutral)<br>(charged) (charged/neutral)Y(aromatic) (charged)<br>(neutral)<br>(charged/polar/aromatic) (F/Y) (charged/neutral) (R/K)<br>(charged/neutral) (Y) (Y/F) (E/D)V<br>(H/N) (F/Y) (S/D) (R/K) (G/K)Y(Y/F)DV<br>HFSRGYYDV<br>HYIKVYYEA<br>HYSSRFFEV<br>NFRVMFFKA<br>HYSSRFFEV<br>DFTVPFYNA<br>NYDKKYFDV<br>YFPLVYYDV<br>HYSSRFFDV |

TABLE 1b

| Antigen binding site | V_H | V_L | scFV |
|---|---|---|---|
| 2F6 (WT) | DVKLVESGGGLVKLGGSLK<br>LSCAASGFTFSSYYMSWVR<br>QTPEKRLELVAAINSNGGS<br>TYYPDTVKGRFTISRDNAK<br>NTLYLQMSSLKSEDTAFYY<br>CTRHYSSRFFDVWGAGTTV<br>TVSS<br>(SEQ ID NO: 35) | MADIVMTQSQKFMSTSVGDR<br>VSVTCKASQNVGTNVAWYQQ<br>KPGQSPKALIYSASFRYSGV<br>PDRFTGSGSGTDFTLTISNV<br>QSEDLAEFFCQQYNSYPFTF<br>GSGTRLEIK<br>(SEQ ID NO: 36) | MADIVMTQSQKFMSTSVGDRV<br>SVTCKASQNVGTNVAWYQQKP<br>GQSPKALIYSASFRYSGVPDR<br>FTGSGSGTDFTLTISNVQSED<br>LAEFFCQQYNSYPFTFGSGTR<br>LEIKGGGGSGGGGSGGGGSDV<br>KLVESGGGLVKLGGSLKLSCA<br>ASGFTFSSYYMSWVRQTPEKR<br>LELVAAINSNGGSTYYPDTVK<br>GRFTISRDNAKNTLYLQMSSL<br>KSEDTAFYYCTRHYSSRFFDV<br>WGAGTTVTVSS<br>(SEQ ID NO: 37) |
| Mutant #18 | GSLKLSCAASGFTFSSYYM<br>SWVRQTPEKRLELVAAINS | GDRVSVTCKASQNVGTNVAW<br>YQQKPGQSPKALIYSASFRY | STSVGDRVSVTCKASQNVGTN<br>VAWYQQKPGQSPKALIYSASF |

TABLE 1b-continued

| Antigen binding site | V_H | V_L | scFV |
|---|---|---|---|
| | NGGSTYYPDTVKGRFTISR DNAKNTLYLQMSSLKSEDT AFYYCTRHFSRGYYDVWGA GTTVTVSS (SEQ ID NO: 38) | SGVPDRFTGSGSGTDFTLTI SVVQSEDLAEFFCQQYNSYP FTFGSGTRLEIK | RYSGVPDRFTGSGSGTDFTLT ISNVQSEDLAEFFCQQYNSYP FTFGSGTRLEIKGGGGSGGGG SGGGGSDVKLVESGGGLVKLG GSLKLSCAASGFTFSSYYMSW VRQTPEKRLELVAAINSNGGS TYYPDTVKGRFTISRDNAKNT LYLQMSSLKSEDTAFYYCTRH FSRGYYDVWGAGTTVTVSS (SEQ ID NO: 39) |
| Mutant #78 | DVKLVESGGGLVKLGGSLK LSCAASGFTFSSYYMSWVR QTPEKRLELVAAINSNGGS TYYPDTVKGRFTISRDNAK NTLYLQMSSLKSEDTAFYY CTRNYDKKYFDVWGAGTTV TVSS (SEQ ID NO: 40) | MADIVMTQSQKFMSTSVGDR VTCKASQNVGTNVAWYQQKP QSPKALIYSASFRYSGVPDR FTGSGSGTDFTLTISNVQSE DLAEFFCQQYNSYPFTFGSG TRLEIK | MADIVMTQSQKFMSTSVGDRV SVTCKASQNVGTNVAWYASQN VGTNVAWYQQKPGQSPKALIY SASFRYSGVPDRFTGSGSGTD FTLTISNVQSEDLAEFFCQQY NSYPFTFGSGTRLEIKGGGGS GGGGSFFFFSDVKLVESGGGL VKLGGSLKLSCAASGFTFSSY YMSWVRQTPEKRLELVAAINS NGGSTYYPDTVKGRFTISRDN AKNTLYLQMSSLKSEDTAFYY CTRNYDKKYFDVWGAGTTVTV SS(SEQ ID NO: 41) |

In certain embodiments the antigen binding site is one having at least 75%, preferably 80%, more preferably 85%, more preferably 90%, more preferably 95%, more preferably 96%, 97%, 98% or 99% identity to an antigen binding site described above.

In certain embodiments the CDR is one having at least 75%, preferably 80%, more preferably 85%, more preferably 90%, more preferably 95%, more preferably 96%, 97%, 98% or 99% identity to a CDR shown in Table 1a.

In certain embodiments the antigen binding site comprises or consists of a $V_H$, $V_L$ or scFv sequence shown in Table 1 b or has a sequence that has 75%, preferably 80%, more preferably 85%, more preferably 90%, more preferably 95%, more preferably 96%, 97%, 98% or 99% identity to a $V_H$, $V_L$ or scFV sequence described in Table 1 b. In other embodiments there is provided an antigen binding site or CDR and/or FR having a sequence as described above and including one or more mutations for increasing the affinity of said site for binding to an anti –$P2X_7$ receptor. The mutation may result in a substitution, insertion or deletion of a residue in one or more of CDR1, CDR2 or CDR3, or one or more or FR1, FR2, FR3 or FR4.

In certain embodiments antigen binding sites of the invention and molecules comprising same bind to an epitope that is exclusively expressed on non ATP-binding $P2X_7$ receptors (otherwise known as "non-functional receptors"). The epitope and peptides forming it have been found to be useful for generating monoclonal antibodies that bind to non-functional $P2X_7$ receptors expressed on live cells.

Live cell binding is important because the expression of the non functional $P2X_7$ receptor in or on cells, examples being epithelial cells, is believed to be a biomarker of many cancers such as epithelial cancers and other conditions. Accordingly, with monoclonal antibodies that bind live cells it becomes possible to provide systemic therapeutics either in the form of the antibody itself, or an antibody-cytotoxic agent conjugate—to a wide range of diseases characterised by expression of non functional $P2X_7$ receptors. It also becomes possible to provide for in vivo imaging and diagnosis or monitoring of diseases characterised by expression of non functional $P2X_7$ receptors.

The epitope is found only on the $P2X_7$ receptor i.e. the trimer formed from $P2X_7$ monomers. More particularly, the epitope spans adjacent $P2X_7$ monomers in the trimeric $P2X_7$ receptor. Individual $P2X_7$ monomers that are not aligned as in a non functional trimeric receptor therefore do not contain the epitope. This advantageously permits one to stage tumours. This is more difficult to do with antibodies that bind to both monomeric $P2X_7$ and the trimeric receptor.

Thus in certain embodiments the antigen binding sites of the invention bind to an epitope of a $P2X_7$ receptor the epitope being formed of:
a first region in the form of a region of a first monomer of a $P2X_7$ receptor; and
a second region in the form of a region of a second monomer of the receptor;
wherein the first and second regions are formed in the receptor by cis isomerisation of a residue at position 210 of SEQ ID No: 1 of a monomer of the receptor;
and wherein the first and second regions are arranged adjacent each other in the receptor thereby permitting binding of an antigen binding site of an anti-$P2X_7$ antibody to the first and second regions forming the epitope.

Typically the epitope is a conformational epitope. In these embodiments, the first and second regions each define a molecular space that each include one or more residues of SEQ ID NO: 1. Typically the first region is one that defines a molecular space including one or more of the residues of SEQ ID No: 1: that are exposed for binding to an antigen binding site of an antibody as a consequence of cis isomerisation of Pro210 of a monomer having a sequence shown in SEQ ID No: 1. These residues include Gly 200, His 201, Asn 202, Tyr 203, Thr 204, Thr 205, Arg 206, Asn 207, Ile 208, Leu 209 and Pro210. In one embodiment the first region includes at least one of these residues. Typically the first region includes at least 4 of these residues, although it may be less, for example, 2 or 3, depending on how many residues are presented in the second region. In one embodiment, the first region includes at least 1 pair of residues shown in the Table 2 below:

TABLE 2

| | | | | | | | | |
|---|---|---|---|---|---|---|---|---|
| His 201 | Asn 202 | Tyr 203 | Thr 204 | Thr 205 | Arg 206 | Asn 207 | Ile 208 | Leu 209 |
| Gly 200 | Gly 200 | Gly 200 | Gly 200 | Gly 200 | Gly 200 | Gly 200 | Gly 200 | Gly 200 |
| | Asn 202 | Tyr 203 | Thr 204 | Thr 205 | Arg 206 | Asn 207 | Ile 208 | Leu 209 |
| | His 201 | His 201 | His 201 | His 201 | His 201 | His 201 | His 201 | His 201 |
| | | Tyr 203 | Thr 204 | Thr 205 | Arg 206 | Asn 207 | Ile 208 | Leu 209 |
| | | Asn 202 | Asn 202 | Asn 202 | Asn 202 | Asn 202 | Asn 202 | Asn 202 |
| | | | Thr 204 | Thr 205 | Arg 206 | Asn 207 | Ile 208 | Leu 209 |
| | | | Tyr 203 | Tyr 203 | Tyr 203 | Tyr 203 | Tyr 203 | Tyr 203 |
| | | | | Thr 205 | Arg 206 | Asn 207 | Ile 208 | Leu 209 |
| | | | | Thr 204 | Thr 204 | Thr 204 | Thr 204 | Thr 204 |
| | | | | | Arg 206 | Asn 207 | Ile 208 | Leu 209 |
| | | | | | Thr 205 | Thr 205 | Thr 205 | Thr 205 |
| | | | | | | Asn 207 | Ile 208 | Leu 209 |
| | | | | | | Arg 206 | Arg 206 | Arg 206 |
| | | | | | | | Ile 208 | Leu 209 |
| | | | | | | | Asn 207 | Asn 207 |
| | | | | | | | | Leu 209 |
| | | | | | | | | Ile 208 |

In certain embodiments the first region includes 2 or more pairs of residues shown in Table 2.

The first region may additionally contain one or more peripheral residues that are intimately involved in formation of the ATP binding site on the larger of the two extracellular domain folds. These are Lys 193, Phe 275 and Arg 294. Arg 125 is located in the smaller of the two extracellular domain folds. Thus in certain embodiments, the first region further includes one or more of the following residues of SEQ ID No: 1: Arg 125, Lys 193, Phe 275 and Arg 294. It will be understood that the first region does not consist of these residues alone. That is the first region, as discussed above, defines a molecular space including one or more of the residues of SEQ ID No: 1: that are exposed for binding to an antigen binding site of an antibody as a consequence of cis isomerisation of Pro210 of a monomer having a sequence shown in SEQ ID No: 1. In this context, the Arg 125, Lys 193, Phe 275 and Arg 294 are only provided in addition, but not alternate to for example one or more of the residues Gly 200, His 201, Asn 202, Tyr 203, Thr 204, Thr 205, Arg 206, Asn 207, Ile 208, Leu 209.

Typically the second region is one that defines a molecular space including one or more of the residues of SEQ ID No: 1: that are exposed for binding to an antigen binding site of an antibody as a consequence of cis isomerisation of Pro210 of a monomer having a sequence shown in SEQ ID No: 1. These residues include Lys 297, Tyr 298, Tyr 299, Lys 300, Glu 301, Asn 302, Asn 303, Val 304, Glu 305 and Lys 306.

In one embodiment the second region includes at least one of these residues. Typically the second region includes at least 4 of these residues, although it may be less, for example, 2 or 3, depending on how many residues are presented in the first region. In one embodiment, the second region includes at least 1 pair of residues shown in the Table 3 below:

TABLE 3

| | | | | | | | | |
|---|---|---|---|---|---|---|---|---|
| Tyr 298 | Tyr 299 | Lys 300 | Glu 301 | Asn 302 | Asn 303 | Val 304 | Glu 305 | Lys 306 |
| Lys 297 | Lys 297 | Lys 297 | Lys 297 | Lys 297 | Lys 297 | Lys 297 | Lys 297 | Lys 297 |
| | Tyr 298 | Tyr 298 | Tyr 298 | Tyr 298 | Tyr 298 | Tyr 298 | Tyr 298 | Tyr 298 |
| | Tyr 299 | Lys 300 | Glu 301 | Asn 302 | Asn 303 | Val 304 | Glu 305 | Lys 306 |
| | | Tyr 299 | Tyr 299 | Tyr 299 | Tyr 299 | Tyr 299 | Tyr 299 | Tyr 299 |
| | | Glu 301 | Glu 301 | Asn 302 | Asn 303 | Val 304 | Glu 305 | Lys 306 |
| | | | Lys 300 | Lys 300 | Lys 300 | Lys 300 | Lys 300 | Lys 300 |
| | | | Glu 301 | Asn 302 | Asn 303 | Val 304 | Glu 305 | Lys 306 |
| | | | | Glu 301 | Glu 301 | Glu 301 | Glu 301 | Glu 301 |
| | | | | Asn 302 | Asn 303 | Val 304 | Glu 305 | Lys 306 |
| | | | | | Asn 302 | Asn 302 | Asn 302 | Asn 302 |
| | | | | | Asn 303 | Val 304 | Glu 305 | Lys 306 |
| | | | | | | Asn 303 | Asn 303 | Asn 303 |
| | | | | | | Val 304 | Glu 305 | Lys 306 |
| | | | | | | | Val 304 | Val 304 |
| | | | | | | | Glu 305 | Lys 306 |
| | | | | | | | | Glu 305 |
| | | | | | | | | Lys 306 |

In certain embodiments the second region includes 2 or more pairs of residues shown in Table 3.

The second region may additionally contain one or more peripheral residues that are intimately involved in formation of the ATP binding site. These are Arg 307 and Lys 311. Thus in certain embodiments, the second region further includes Arg 307 and/or Lys 311. It will be understood that the second region does not consist of these residues alone. That is, the second region, as discussed above, defines a molecular space including one or more of the residues of SEQ ID No: 1: that are exposed for binding to an antigen binding site of an antibody as a consequence of cis isomerisation of Pro210 of a monomer having a sequence shown in SEQ ID No: 1. In this context, the Arg 307 and Lys 311 are only provided in addition, but not alternate to for example one or more of the residues Lys 297, Tyr 298, Tyr 299, Lys 300, Glu 301, Asn 302, Asn 303, Val 304, Glu 305 and Lys 306.

In certain embodiments, the epitope is, or includes a linear epitope. Examples include where the first region includes one of the following sequences of SEQ ID No: 1 in Table 4:

TABLE 4

Gly 200 to Tyr 203
His 201 to Thr 204
Asn 202 to Thr 205
Tyr 203 to Arg 206
Thr 204 to Asn 207
Thr 205 to Ile 208
Arg 206 to Leu 209

In these embodiments, the second region of the epitope may include one of the following sequences of SEQ ID No: 1 in Table 5:

TABLE 5

Lys 297 to Lys 300
Tyr 298 to Glu 301
Tyr 299 to Asn 301
Lys 300 to Asn 303
Glu 301 to Val 304
Asn 301 to Glu 305
Asn 303 to Lys 306

In certain embodiments, the first region contains more residues than the second region. In other embodiments, the second region contains more residues than the first region.

The first region and second region may each contain from about 4 to about 10 residues, for example 5, 6, 7, 8 or 9 residues. Where there are more residues in the second region, there may be fewer residues in the first region, ie less than 4, for example 2 or 3. The same applies vice versa.

As described herein, the first and second regions are arranged adjacent each other in the receptor thereby permitting binding of an antigen binding site of an anti-$P2X_7$ antibody to the first and second regions forming the epitope. In more detail, the inventors have found that although located on separate monomers, the first and second regions in combination form an epitope that can be bound by a single antigen binding site of an antibody. Generally, the first and second regions of the epitope are spaced apart no more than about 40 Angstroms. If the distance is greater than this, the antibody binding affinity tends to decrease as the antigen binding site is required to traverse a larger distance across the monomers within the receptor in which case fewer residues are bound. Generally the first and second regions are spaced apart about 10 Angstroms, although greater distances less than 40 Angstroms are possible such as 15, 20, 25, 30, 35 Angstroms.

The epitope described herein may be provided in a substantially purified or isolated form, for example as a fragment of a naturally occurring $P2X_7$ receptor or as a synthetic or recombinant $P2X_7$ receptor.

Marks et al. (1992) BioTechnology 10:779, which describes affinity maturation by VH and VL domain shuffling; Barbas et al. (1994) Proc Nat. Acad. Sci. USA 9 1:3809; Schier et al. (1995) Gene 169:147-155; Yelton et al. (1995) J. Immunol. 155:1994; Jackson et al (1995), J. Immunol. 154(7):3310; and Hawkins et al, (1992) J. Mol. Biol. 226:889, which describe random mutagenesis of hypervariable region and/or framework residues, are examples of procedures known in the art for affinity maturation of antigen binding sites. In certain embodiments, a nucleic acid encoding one or more of the sequences shown in Table 1a or b is mutagenized to create a diverse library of sequences. The library is then screened against a target including an epitope of a non functional $P2X_7$ receptor. An exemplary method is shown in the Examples herein.

In another embodiment there is provided an antigen binding site as described above wherein an amino acid sequence forming one or more of FR1, CDR1, FR2, CDR2, FR3, CDR3 and FR4 is derived from a human sequence or in the form of a human sequence.

The antigen binding site may be presented in a humanized form including non-human (e.g., murine) and human immunoglobulin sequences. Typically all but the CDR sequences of the antigen binding site are from a non-human species such as mouse, rat or rabbit. In some instances, framework residues of the antigen binding site may also be non human. Where the antigen binding site is provided in the form of a whole antibody, typically at least a portion of an immunoglobulin constant region (Fc) is human, thereby allowing various human effector functions.

Methods for humanizing non-human antigen binding sites are well known in the art, examples of suitable processes including those in Jones et al., (1986) Nature, 321:522; Riechmann et al., (1988) Nature, 332:323; Verhoeyen et al., (1988) Science, 239:1534.

Phage display methods described herein using antibody libraries derived from human immunoglobulin sequences are useful for generating human antigen binding sites and human antibodies.

Also, transgenic mammals that are incapable of expressing functional endogenous immunoglobulins, but which can express human immunoglobulin genes can be used. These mice may be generated by random or targeted insertion of the human heavy and light chain immunoglobulin genes into embryonic stem cells. The host heavy and light chain immunoglobulin genes may be rendered non-functional by the insertion or by some other recombination event, for example by homozygous deletion of the host JH region. The transfected embryonic stem cells are expanded and microinjected into blastocysts to produce chimeric mice that are then bred to produce homozygous offspring that express human antigen binding sites. After immunization with a $P2X_7$ epitope, human monoclonal antibodies can be obtained. One benefit of transgenic animal systems is that it is possible to produce therapeutically useful isotypes because the human immunoglobulin transgenes rearrange during B-cell differentiation and subsequently undergo class switching and somatic mutation in the transgenic mice.

Variable domains including CDRs and FRs of the invention may have been made less immunogenic by replacing surface-exposed residues so as to make the antibody appear as self to the immune system. Padlan, E. A., 1991, Mol. Immunol. 28, 489 provides an exemplary method. Generally, affinity is preserved because the internal packing of amino acid residues in the vicinity of the antigen binding site remains unchanged and generally CDR residues or adjacent residues which influence binding characteristics are not to be substituted in these processes.

In another embodiment there is provided an anti $P2X_7$ receptor immunoglobulin variable domain, antibody, Fab, dab or scFv including an antigen binding site as described above.

Lower molecular weight antibody fragments, as compared with whole antibodies may have improved access to solid tumors and more rapid clearance which may be particularly useful in therapeutic and in vivo diagnostic applications.

Various techniques have been developed for the production of antibody fragments including proteolytic digestion of intact antibodies and recombinant expression in host cells. With regard to the latter, as described below, Fab, Fv and scFv antibody fragments can all be expressed in and secreted from *E. coli*, antibody fragments can be isolated from the antibody phage libraries and Fab'-SH fragments can be directly recovered from *E. coli* and chemically coupled to form F(ab')2 fragments. In another approach, F(ab')2 fragments are isolated directly from recombinant host cell culture.

In certain embodiments, the antigen binding site is provided in the form of a single chain Fv fragment (scFv). Fv and scFv are suitable for reduced nonspecific binding during in vivo use as they have intact combining sites that are devoid of constant regions. Fusion proteins including scFv may be constructed to yield fusion of an effector protein at either the amino or the carboxy terminus of an scFv. Preferably the scFV is in the form of a $V_H$ domain fused by a linker to a $V_L$ domain. In one embodiment the linker is at least 15 amino acids in length. Typically, the linker is at least 10 amino acids in length. In one embodiment the linker is comprised of generally glycine or serine residues. Typically, the linker is GGGGSGGGGSGGGGS (SEQ ID NO:47).

In one embodiment the scFV has the sequence:

MADIVMTQSQKFMSTSVGDRVSVTCKASQNVGTNVAWYQQKPGQSPKAL

IYSASFRYSGVPDRFTGSGSGTDFTLTISNVQSEDLAEFFCQQYNSYPF

TFGSGTRLEIKGGGGSGGGGSGGGGSDVKLVESGGGLVKLGGSLKLSCA

ASGFTFSSYYMSWVRQTPEKRLELVAAINSNGGSTYYPDTVKGRFTISR

DNAKNTLYLQMSSLKSEDTAFYYCTRHYSSRFFDVWGAGTTVTVSS

In another embodiment there is provided a diabody or triabody or other multispecific antibody including an antigen binding site as described above. Multispecific antibodies may be assembled using polypeptide domains that allow for multimerization. Examples include the CH2 and CH3 regions of the Fc and the CH1 and Ckappa/lambda regions. Other naturally occurring protein multimerization domains may be used including leucine zipper domain (bZIP), helix-loop-helix motif, Src homology domain (SH2, SH3), an EF hand, a phosphotyrosine binding (PTB) domain, or other domains known in the art.

In another embodiment there is provided a fusion domain or heterologous protein including an antigen binding site, immunoglobulin variable domain, antibody, Fab, dab, scFv, diabody or triabody as described above.

A heterologous polypeptide may be recombinantly fused or chemically conjugated to an N- or C-terminus of an antigen binding site or molecule containing same of the invention.

The heterologous polypeptide to which the antibody or antigen binding site is fused may be useful to target to the $P2X_7$ receptor expressing cells, or useful to some other function such as purification, or increasing the in vivo half life of the polypeptides, or for use in immunoassays using methods known in the art.

In preferred embodiments, a marker amino acid sequence such as a hexa-histidine peptide is useful for convenient purification of the fusion protein. Others include, but are not limited to, the "HA" tag, which corresponds to an epitope derived from the influenza hemagglutinin protein and the "flag" tag. For example, an scFv of the invention may be both flag tagged and His tagged with following sequence:

MADIVMTQSQKFMSTSVGDRVSVTCKASQNVGTNVAWYQQKPGQSPKA

LIYSASFRYSGVPDRFTGSGSGTDFTLTISNVQSEDLAEFFCQQYNSY

PFTFGSGTRLEIKGGGGSGGGGSGGGGSDVKLVESGGGLVKLGGSLKL

SCAASGFTFSSYYMSWVRQTPEKRLELVAAINSNGGSTYYPDTVKGRF

TISRDNAKNTLYLQMSSLKSEDTAFYYCTRHYSSRFFDVWGAGTTVTV

SSAAADYKDDDDKAAAHHHHHH

Further, the antigen binding site, immunoglobulin variable domain, antibody, Fab, dab, scFv, diabody or triabody of the invention may be modified by glycosylation, acetylation, pegylation, phosphorylation, amidation, derivatization by known protecting/blocking groups, proteolytic cleavage, linkage to a cellular ligand or other protein, etc.

Antigen binding sites of the invention can be composed of amino acids joined to each other by peptide bonds or modified peptide bonds, i.e., peptide isosteres, and may contain amino acids other than the 20 gene-encoded amino acids. Antigen binding sites of the invention may be modified by natural processes, such as posttranslational processing, or by chemical modification techniques which are well known in the art. Such modifications are well described in basic texts, as well as in research literature. Modifications can occur anywhere in the antigen binding site, including the peptide backbone, the amino acid side-chains and the amino or carboxyl termini, or on moieties such as carbohydrates. It will be appreciated that the same type of modification may be present in the same or varying degrees at several sites in a given antigen binding site. Also, a given antigen binding site may contain many types of modifications. An antigen binding site may be branched, for example, as a result of ubiquitination, and they may be cyclic, with or without branching. Cyclic, branched, and branched cyclic antigen binding sites may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

In another embodiment there is provided a conjugate in the form of an antigen binding site, immunoglobulin variable domain, antibody, Fab, dab, scFsv, diabody, triabody or fusion protein as described above conjugated to a cytotoxic agent such as a chemo therapeutic agent, a drug, a growth inhibitory agent, a toxin (e.g., an enzymatically active toxin of bacterial, fungal, plant, or animal origin, or fragments thereof), or a label such as a radioactive isotope (i.e., a radio conjugate). In another aspect, the invention further provides methods of using the immunoconjugates. In one aspect, an immunoconjugate comprises any of the above variable domains covalently attached to a cytotoxic agent or a detectable agent.

In another embodiment there is provided an antibody for binding to an antigen binding site of an immunoglobulin variable domain, antibody, Fab, dab, scFv, diabody, triabody, fusion protein or conjugate as described above.

In another embodiment there is provided a nucleic acid encoding an antigen binding site, immunoglobulin variable domain, antibody, Fab, dab, scFv, diabody, triabody, fusion protein or conjugate as described above.

A polynucleotide encoding an CDR or FR according to any one of the general formulae described above, or an antigen binding site comprised of same, may be generated from a nucleic acid from any source, for example by chemical synthesis or isolation from a cDNA or genomic library. For example a cDNA library may be generated from an antibody producing cell such as a B cell, plasma cell or hybridoma cell and the relevant nucleic acid isolated by PCR amplification using oligonucleotides directed to the particular clone of interest. Isolated nucleic acids may then be cloned into vectors using any method known in the art. The relevant nucleotide sequence may then be mutagenized using methods known in the art e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY), to generate antigen binding sites having a different amino acid sequence, for example to create amino acid substitutions, deletions, and/or insertions.

In another embodiment there is provided a vector including a nucleic acid described above. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The antigen binding site may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the antigen binding site-encoding DNA that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader, or acid phosphatase leader or the *C. albicans* glucoamylase leader. In mammalian cell expression, mammalian signal sequences may be used to direct secretion of the protein, such as signal sequences from secreted polypeptides of the same or related species, as well as viral secretory leaders.

Polynucleotide sequences encoding polypeptide components of the antigen binding site of the invention can be obtained using standard recombinant techniques as described above. Polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides.

In general, plasmid vectors containing replicon and control sequences which are derived from species compatible with the host cell are used in connection with these hosts. Both expression and cloning vectors contain a nucleic acid sequence that enables the vector to replicate in one or more selected host cells, as well as marking sequences which are capable of providing phenotypic selection in transformed cells. Such sequences are well known for a variety of bacteria, yeast, and viruses. The origin of replication from the plasmid pBR322, which contains genes encoding ampicillin (Amp) and tetracycline (Tet) resistance and thus provides easy means for identifying transformed cells, is suitable for most Gram-negative bacteria, the 2 μm plasmid origin is suitable for yeast, and various viral origins (SV40, polyoma, adenovirus, VSV or BPV) are useful for cloning vectors in mammalian cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron (a cistron being segment of DNA that contains all the information for production of single polypeptide) pairs. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters recognized by a variety of potential host cells are well known. Promoters suitable for use with prokaryotic hosts include the PhoA promoter, the β-galactamase and lactose promoter systems, alkaline phosphatase, a tryptophan (trp) promoter system and hybrid promoters such as the tac or the trc promoter. Promoters for use in bacterial systems also will contain a Shine-Dalgarno (S.D.) sequence operably linked to the DNA encoding an antigen binding site of the invention. However, other promoters that are functional in bacteria (such as other known bacterial or phage promoters) are suitable as well. Their nucleotide sequences have been published, thereby enabling a skilled person operably to ligate them to cistrons encoding the target light and heavy chains using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB⁻ strains) provide cytoplasm conditions that are favorable for disulfide bond formation, thereby permitting proper folding and assembly of expressed protein subunits.

The present invention provides an expression system in which the quantitative ratio of expressed polypeptide components can be modulated in order to maximize the yield of secreted and properly assembled antigen binding sites of the invention. Such modulation is accomplished at least in part by simultaneously modulating translational strengths for the polypeptide components.

In terms of expression in eukaryotic host cells, the vector components generally include, but are not limited to, one or more of the following: a signal sequence, an origin of replication, one or more marker genes, an enhancer element, a promoter, and a transcription termination sequence.

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed {i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

Generally, an origin of replication component is not needed for mammalian expression vectors. For example, the SV40 origin may typically be used only because it contains the early promoter.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

An example of suitable selectable markers for mammalian cells are those that enable the identification of cells competent to take up the antigen binding site-encoding nucleic acid, such as DHFR or thymidine kinase, metallothionein-I and -II, preferably primate metallothionein genes, adenosine deaminase, ornithine decarboxylase, etc. An appropriate host cell when wild-type DHFR is employed is the CHO cell line deficient in DHFR activity (e.g., ATCC CRL-9096), prepared and propagated. For example, cells transformed with the DHFR selection gene are first identified by culturing all of the transformants in a culture medium that contains methotrexate (Mtx), a competitive antagonist of DHFR. Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418.

Expression and cloning vectors usually contain a promoter operably linked to the antigen binding site encoding nucleic acid sequence to direct mRNA synthesis. Promoters recognized by a variety of potential host cells are well known.

Eukaryotic genes generally have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes including enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Antigen binding site transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the antigen binding site by higher eukaryotes may be increased by inserting an enhancer sequence into the vector. Enhancer sequences include those known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antigen binding site.

In another embodiment there is provided a cell including a vector or nucleic acid described above. The nucleic acid molecule or vector may be present in the genetically modified host cell or host either as an independent molecule outside the genome, preferably as a molecule which is capable of replication, or it may be stably integrated into the genome of the host cell or host.

The host cell of the present invention may be any prokaryotic or eukaryotic cell.

Examples of prokaryotic cells are those generally used for cloning like *E. coli* or *Bacillus subtilis*. Furthermore, eukaryotic cells comprise, for example, fungal or animal cells.

Examples for suitable fungal cells are yeast cells, preferably those of the genus *Saccharomyces* and most preferably those of the species *Saccharomyces cerevisiae*.

Examples of animal cells are, for instance, insect cells, vertebrate cells, preferably mammalian cells, such as e.g. HEK293, NSO, CHO, MDCK, U2-OS, Hela, NIH3T3, MOLT-4, Jurkat, PC-12, PC-3, IMR, NT2N, Sk-n-sh, CaSki, C33A. These host cells, e.g. CHO-cells, may provide post-translational modifications to the antibody molecules of the invention, including leader peptide removal, folding and assembly of H (heavy) and L (light) chains, glycosylation of the molecule at correct sides and secretion of the functional molecule.

Further suitable cell lines known in the art are obtainable from cell line depositories, like the American Type Culture Collection (ATCC).

In another embodiment there is provided an animal including a cell described above. In certain embodiments, animals and tissues thereof containing a transgene are useful in producing the antigen binding sites of the invention. The introduction of the nucleic acid molecules as transgenes into non-human hosts and their subsequent expression may be employed for the production of the antigen binding sites, for example, the expression of such a transgene in the milk of the transgenic animal provide for means of obtaining the antigen binding sites in quantitative amounts. Useful transgenes in this respect comprise the nucleic acid molecules of the invention, for example, coding sequences for the antigen binding sites described herein, operatively linked to promoter and/or enhancer structures from a mammary gland specific gene, like casein or beta-lactoglobulin. The animal may be non-human mammals, most preferably mice, rats, sheep, calves, dogs, monkeys or apes.

In another embodiment there is provided a pharmaceutical composition including an antigen binding site, immunoglobulin variable domain, antibody, Fab, dab, scFv, diabody, triabody, fusion protein or conjugate as described above and a pharmaceutically acceptable carrier, diluent or excipient.

Methods of preparing and administering antigen binding sites thereof to a subject in need thereof are well known to or are readily determined by those skilled in the art. The route of administration of the antigen binding site may be oral, parenteral, by inhalation or topical.

The term parenteral as used herein includes, e.g., intravenous, intraarterial, intraperitoneal, intramuscular, subcutaneous, rectal or vaginal administration.

While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringers, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions, in such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating an active compound (e.g., antigen binding site) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed disorders.

Effective doses of the compositions of the present invention, for treatment of disorders as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For treatment of certain disorders with an antigen binding site, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more antigen binding sites with different binding specificities are administered simultaneously, in which case the dosage of each antigen binding sites administered falls within the ranges indicated.

An antigen binding site disclosed herein can be administered on multiple occasions. Intervals between single dosages can be weekly, monthly or yearly. Intervals can also be irregular as indicated by measuring blood levels of target polypeptide or target molecule in the patient. In some methods, dosage is adjusted to achieve a plasma polypeptide concentration of 1-1000 ug/mL and in some methods 25-300 ug/mL. Alternatively, antigen binding sites can be administered as a sustained release formulation, in which case less frequent administration is required. Dosage and frequency vary depending on the half-life of the antigen binding site in the patient. The half-life of an antigen binding site can also be prolonged via fusion to a stable polypeptide or moiety, e.g., albumin or PEG. In general, humanized antibodies show the longest half-life, followed by chimeric antibodies and nonhuman antibodies. In one embodiment, the antigen binding site of the invention can be administered in unconjugated form. In another embodiment the antigen binding sites for use in the methods disclosed herein can be administered multiple times in conjugated form. In still another embodiment, the antigen binding sites of the invention can be administered in unconjugated form, then in conjugated form, or vice versa.

The dosage and frequency of administration can vary depending on whether the treatment is prophylactic or therapeutic. In prophylactic applications, compositions comprising antibodies or a cocktail thereof are administered to a patient not already in the disease state or in a pre-disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule, e.g., antigen binding site per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding an antigen binding site (e.g., in a vector). Doses for nucleic acids encoding polypeptides range from about 10 ng to 1 g, 100 ng to 100 mg, 1 ug to 10 mg, or 30-300 ug DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment, in some methods, agents are injected directly into a particular tissue where non-functional $P2X_7$ receptor cells have accumulated, for example intracranial injection. Intramuscular injection or intravenous infusion are preferred for administration of antibody, in some methods, particular therapeutic antibodies are injected directly into the cranium, in some methods, antibodies are administered as a sustained release composition or device.

An antigen binding site of the invention can optionally be administered in combination with other agents that are effective in treating the disorder or condition in need of treatment (e.g., prophylactic or therapeutic).

In another embodiment there is provided a pharmaceutical composition including an antigen binding site, immunoglobulin variable domain, antibody, Fab, dab, scFv, diabody, triabody, fusion protein or conjugate as described above, a diluent and optionally a label.

In certain embodiments, the antigen binding sites or molecule including same are detectably labelled. Many different labels can be used including enzymes, radioisotopes, colloidal metals, fluorescent compounds, chemiluminescent compounds, and bioluminescent compounds. Fluorochromes (fluorescein, rhodamine, Texas Red, etc.), enzymes (horse radish peroxidase, β-galactosidase, alkaline phosphatase etc.), radioactive isotopes ($^{32}P$ or $^{125}I$), biotin, digoxygenin, colloidal metals, chemi- or bioluminescent compounds (dioxetanes, luminol or acridiniums) are commonly used.

Detection methods depend on the type of label used and include autoradiography, fluorescence microscopy, direct and indirect enzymatic reactions. Examples include Westernblotting, overlay-assays, RIA (Radioimmuno Assay) and IRMA (Immune Radioimmunometric Assay), EIA (Enzyme Immuno Assay), ELISA (Enzyme Linked Immuno Sorbent Assay), FIA (Fluorescent Immuno Assay), and CLIA (Chemioluminescent Immune Assay).

In another embodiment there is provided a kit or article of manufacture including an antigen binding site, immunoglobulin variable domain, antibody, Fab, dab, scFv, diabody, triabody, fusion protein, conjugate or pharmaceutical composition as described above.

In other embodiments there is provided a kit for use in a therapeutic application mentioned above, the kit including:
a container holding a therapeutic composition in the form of one or more of an antigen binding site, immunoglobulin variable domain, antibody, Fab, dab, scFv, diabody, triabody, fusion protein, conjugate or pharmaceutical composition;
a label or package insert with instructions for use.

In certain embodiments the kit may contain one or more further active principles or ingredients for treatment of a cancer or for preventing a cancer-related complication described above, or a condition or disease associated with non functional $P2X_7$ receptor expression.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic composition can be used to treat a cancer or to prevent a complication stemming from cancer.

The kit may comprise (a) a therapeutic composition; and (b) a second container with a second active principle or ingredient contained therein. The kit in this embodiment of the invention may further comprise a package insert indicating that the therapeutic composition and other active principle can be used to treat a disorder or prevent a complication stemming from cancer. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic composition. In one embodiment, the device is a syringe. The device may hold 1-2 mL of the therapeutic composition. The therapeutic composition may be provided in the device in a state that is ready for use or in a state requiring mixing or addition of further components.

In another embodiment there is provided a kit or article of manufacture including an antigen binding site, immunoglobulin variable domain, antibody, Fab, dab, scFv, diabody, triabody, fusion protein, conjugate or a diagnostic composition as described above.

In other embodiments there is provided a kit for use in a diagnostic application mentioned above, the kit including:
a container holding a diagnostic composition in the form of one or more of an antigen binding site, immunoglobulin variable domain, antibody, Fab, dab, scFv, diabody, triabody, fusion protein or conjugate;
a label or package insert with instructions for use.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a diagnostic composition which is effective for detection of cancer and may have a sterile access port (for example the container may be an intravenous solution bag or a vial having a stopper pierceable by a hypodermic injection needle). The label or package insert indicates that the diagnostic composition is used for detecting the condition of choice. In one embodiment, the label or package insert includes instructions for use and indicates that the diagnostic composition can be used to detect a cancer or a disease or condition characterised by non functional $P2X_7$ receptor expression.

The kit may comprise (a) a diagnostic composition; and (b) a second container with a second diagnostic agent or second label contained therein. It may further include other materials desirable from a commercial and user standpoint, including other buffers, diluents, filters etc.

In another embodiment there is provided a method for producing an anti $P2X_7$ antigen binding site as described above including expressing a nucleic acid as described above in a cell or non human animal as described above.

The production of an antigen binding site of the invention generally requires an expression vector containing a polynucleotide that encodes the antigen binding site of the invention. A polynucleotide encoding an antigen binding site of the invention may be obtained and sub cloned into a vector for the production of an antigen binding site by recombinant DNA technology using techniques well-known in the art, including techniques described herein. Many different expression systems are contemplated including the use of mammalian cells including human cells for production and secretion of antigen binding sites. Examples of cells include 293F, CHO and the NSO cell line.

Expression vectors containing protein coding sequences and appropriate transcriptional and translational control signals can be constructed using methods known in the art. These include in vitro recombinant DNA techniques, synthetic techniques and in vivo genetic recombination. In certain embodiments there is provided a replicable vector having a nucleic acid encoding an antigen binding site operably linked to a promoter.

Cells transfected with an expression vector may be cultured by conventional techniques to produce an antigen binding site. Thus, in certain embodiments, there is provided host cells or cell transfectants containing a polynucleotide encoding an antigen binding site of the invention operably linked to a promoter. The promoter may be heterologous. A variety of host-expression vector systems may be utilized and in certain systems the transcription machinery of the vector system is particularly matched to the host cell. For example, mammalian cells such as Chinese hamster ovary cells (CHO) may be transfected with a vector including the major intermediate early gene promoter element from human cytomegalovirus. Additionally or alternatively, a host cell may be used that modulates the expression of inserted sequences, or modifies and processes the gene product as required, including various forms of post translational modification. Examples of mammalian host cells having particular post translation modification processes include CHO, VERY, BHK, Hela, COS, MDCK, 293, 3T3, W138, BT483, Hs578T, HTB2, BT2O and T47D, NSO, CRL7O3O and HsS78Bst cells.

Depending upon the use intended for the protein molecule, a number of bacterial expression vectors may be advantageously selected. In one example, vectors that cause the expression of high levels of fusion protein products that are readily purified, such as the *E. coli* expression vector pUR278 may be used where a large quantity of an antigen binding site is to be produced. The expression product may be produced in the form of a fusion protein with lacZ. Other bacterial vectors include pIN vectors and the like. pGEX vectors may also be used to express foreign polypeptides as fusion proteins with glutathione-S-transferase (GST). These fusion proteins are generally soluble and can easily be purified from lysed cells by adsorption and binding to glutathione-agarose affinity matrix followed by elution in the presence of free glutathione. A thrombin and/or factor Xa protease cleavage site may be provided in the expressed polypeptide so that the cloned target gene product can be released from the GST moiety.

*Autographa californica* nuclear polyhedrosis virus (AcNPV) may be used as a vector to express foreign genes in an insect system including *Spodoptera frugiperda* cells. The particular promoter used may depend on where the protein coding is inserted into the sequence. For example, the sequence may be cloned individually into the polyhedrin gene and placed under control of the polyhedrin promoter.

Virus based expression systems may be utilized with mammalian cells such as an adenovirus whereby the coding sequence of interest may be ligated to the adenoviral late promoter and tripartite leader sequence. In vitro or in vivo recombination may then be used to insert this chimeric gene into the adenoviral genome. Insertions into region E1 or E3 will result in a viable recombinant virus that is capable of expressing the antigen binding site in infected host cells. Specific initiation signals including the ATG initiation codon and adjacent sequences may be required for efficient translation of inserted antigen binding site coding sequences. Initiation and translational control signals and codons can be obtained from a variety of origins, both natural and synthetic. Transcription enhancer elements and transcription terminators may be used to enhance the efficiency of expression of a viral based system.

Where long-term, high-yield production of recombinant proteins is required, stable expression is preferred. Generally a selectable marker gene is used whereby following transfection, cells are grown for 1-2 days in an enriched media and then transferred to a medium containing a selective medium in which cells containing the corresponding selectable marker, for example, antibiotic resistance can be screened. The result is that cells that have stably integrated the plasmid into their chromosomes grow and form foci that in turn can be cloned and expanded into cell lines. The herpes simplex virus thymidine kinase, hypoxanthineguanine phosphoribosyltransferase and adenine phosphoribosyltransferase genes are examples of genes that can be employed in tk$^-$, hgprt$^-$ or aprT$^-$ cells, respectively thereby providing appropriate selection systems. The following genes: dhfr, which confers resistance to methotrexate; gpt, which confers resistance to mycophenolic acid; neo, which confers resistance to the aminoglycoside G-418; and hygro, which confers resistance to hygromycin are examples of genes that can be used in anti metabolite selection systems.

An antigen binding site of the invention may be purified by a recombinant expression system by known methods including ion exchange chromatography, affinity chromatography (especially affinity for the specific antigens Protein A or Protein G) and gel filtration column chromatography), centrifugation, differential solubility, or by any other standard technique for the purification of proteins. Purification may be facilitated by providing the antigen binding site in the form of a fusion protein.

Large quantities of the antigen binding sites of the invention may be produced by a scalable process starting with a pilot expression system in a research laboratory that is scaled up to an analytical scale bioreactor (typically from 5 L to about 50 L bioreactors) or production scale bioreactors (for example, but not limited to 75 L, 100 L, 150 L, 300 L, or 500 L). Desirable scalable processes include those wherein there are low to undetectable levels of aggregation as measured by HPSEC or rCGE, typically no more than 5% aggregation by weight of protein down to no more than 0.5% by weight aggregation of protein. Additionally or alternatively, undetectable levels of fragmentation measured in terms of the total peak area representing the intact antigen binding site may be desired in a scalable process so that at least 80% and as much as 99.5% or higher of the total peak area represents intact antigen binding site. In other embodiments, the scalable process of the invention produces antigen binding sites at production efficiency of about from 10 mg/L to about 300 mg/L or higher.

In another embodiment there is provided a method for the treatment of a disease or condition characterised by non functional P2X$_7$ receptor expression in an individual including the step of providing an antigen binding site, immunoglobulin variable domain, antibody, Fab, dab, scFv, diabody, triabody, fusion protein, conjugate or pharmaceutical composition as described above to an individual requiring treatment for said condition. Typically the condition is cancer, especially an epithelial cancer as described herein. In certain embodiments, the individual has metastatic cancer or has the potential for a cancer to metastasize.

Pre-neoplastic and neoplastic diseases are particular examples to which the methods of the invention may be applied. Broad examples include breast tumors, colorectal tumors, adenocarcinomas, mesothelioma, bladder tumors, prostate tumors, germ cell tumor, hepatoma/cholongio, carcinoma, neuroendocrine tumors, pituitary neoplasm, small round cell tumor, squamous cell cancer, melanoma, atypical fibroxanthoma, seminomas, nonseminomas, stromal leydig cell tumors, Sertoli cell tumors, skin tumors, kidney tumors, testicular tumors, brain tumors, ovarian tumors, stomach tumors, oral tumors, bladder tumors, bone tumors, cervical tumors, esophageal tumors, laryngeal tumors, liver tumors, lung tumors, vaginal tumors and Wilm's tumor.

Examples of particular cancers include but are not limited to adenocarcinoma, adenoma, adenofibroma, adenolymphoma, adontoma, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, ameloblastoma, angiokeratoma, angiolymphoid hyperplasia with eosinophilia, angioma sclerosing, angiomatosis, apudoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, branchioma, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, carcinoma (e.g. Walker, basal cell, basosquamous, Brown-Pearce, ductal, Ehrlich tumor, Krebs 2, Merkel cell, mucinous, non-small cell lung, oat cell, papillary, scirrhous, bronchiolar, bron chogenic, squamous cell, and transitional cell), carcinosarcoma, cervical dysplasia, cystosarcoma phyllodies, cementoma, chordoma, choristoma, chondrosarcoma, chondroblastoma, craniopharyngioma, cholangioma, cholesteatoma, cylindroma, cystadenocarcinoma, cystadenoma, dermatofibrosarcoma-protuberans, desmoplastic-small-round-cell-tumor, ductal carcinoma, dysgerminoam, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anaemia, fibroma, fibrosarcoma, gall bladder cancer, gastric cancer, gastrointestinal cancers, gastrointestinal-carcinoid-tumor, genitourinary cancers, germ cell tumors, gestationaltrophoblastic-disease, glioma, gynaecological cancers, giant cell tumors, ganglioneuroma, glioma, glomangioma, granulosa cell tumor, gynandroblastoma, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, hamartoma, hemangioendothelioma, hemangioma, hemangiopericytoma, hemangiosarcoma, hemangiosarcoma, histiocytic disorders, histiocytosis malignant, histiocytoma, hepatoma, hidradenoma, hondrosarcoma, immunoproliferative small, opoma, ontraocular melanoma, islet cell cancer, Kaposi's sarcoma, kidney cancer, langerhan's cell-histiocytosis, laryngeal cancer, leiomyosarcoma, leukemia, li-fraumeni syndrome, lip cancer, liposarcoma, liver cancer, lung cancer, lymphedema, lymphoma, Hodgkin's lymphoma, non-Hodgkin's lymphoma, leigomyosarcoma, leukemia (e.g. b-cell, mixed cell, null-cell, t-cell, t-cell chronic, htiv-ii-associated, lymphangiosarcoma, lymphocytic acute, lymphocytic chronic, mast-cell and myeloid), leukosarcoma, leydig cell tumor, liposarcoma, leiomyoma, leiomyosarcoma, lymphangioma, lymphangiocytoma, lymphagioma, lymphagiomyoma, lymphangiosarcoma, male breast cancer, malignant-rhabdoid-tumor-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, malignant carcinoid syndrome carcinoid heart disease, medulloblastoma, meningioma, melanoma, mesenchymoma, mesonephroma, mesothelioma, myoblastoma, myoma, myosarcoma, myxoma, myxosarcoma, nasal cancer, nasopharyngeal cancer, nephroblastoma, neuroblastoma, neurofibromatosis, Nijmegen breakage syndrome, non-melanoma skin cancer, non-small-cell-lung-cancer—(nsclc), neurilemmoma, neuroblastoma, neuroepithelioma, neurofibromatosis, neurofibroma, neuroma, neoplasms (e.g. bone, breast, digestive system, colorectal, liver), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, osteoma, osteosarcoma, ovarian carcinoma, papilloma, paraganglioma, paraganglioma nonchromaffin, pinealoma, plasmacytoma, protooncogene, rare-cancers-and-associated-disorders, renal cell carcinoma, retinoblastoma, rhabdomyosarcoma, Rothmund-Thomson syndrome, reticuloendotheliosis, rhabdomyoma, salivary gland cancer, sarcoma, schwannoma, Sezary syndrome, skin cancer, small cell lung cancer (scic), small intestine cancer, soft tissue sarcoma, spinal cord tumors, squamous-cell-carcinoma-(skin), stomach cancer, synovial sarcoma, sarcoma (e.g. Ewing's experimental, Kaposi's and mast-cell sarcomas), Sertoli cell tumor, synovioma, testicular cancer, thymus cancer, thyroid cancer, transitional-cell-cancer-(bladder), transitional-cell-cancer-(renal-pelvis-/-ureter), trophoblastic cancer, teratoma, theca cell tumor, thymoma, trophoblastic tumor, urethral cancer, urinary system cancer, uroplakins, uterine sarcoma, uterus cancer, vaginal cancer, vulva cancer, Waldenstrom's-macroglobulinemia and Wilms' tumor.

Other diseases and conditions include various inflammatory conditions. Examples may include a proliferative component. Particular examples include acne, angina, arthritis, aspiration pneumonia, disease, empyema, gastroenteritis, inflammation, intestinal flu, nee, necrotizing enterocolitis, pelvic inflammatory disease, pharyngitis, pid, pleurisy, raw throat, redness, rubor, sore throat, stomach flu and urinary tract infections, chronic inflammatory demyelinating polyneuropathy, chronic inflammatory demyelinating polyradiculoneuropathy, chronic inflammatory demyelinating polyneuropathy or chronic inflammatory demyelinating polyradiculoneuropathy.

In another embodiment there is provided a use of an antigen binding site, immunoglobulin variable domain, antibody, Fab, dab, scFsv, diabody, triabody, fusion protein, conjugate or pharmaceutical composition as described above in the manufacture of a medicament for the treatment of cancer.

Dosage amount, dosage frequency, routes of administration etc are described in detail above.

In another embodiment there is provided a method for the diagnosis of cancer including the step of contacting tissues or cells for which the presence or absence of cancer is to be determined with a reagent in the form of an antigen binding site, immunoglobulin variable domain, antibody, Fab, dab, scFv, diabody, triabody, fusion protein, conjugate or diagnostic composition as described above and detecting for the binding of the reagent with the tissues or cells. The method may be operated in vivo or in vitro.

For in situ diagnosis, the antigen binding site may be administered to the organism to be diagnosed by intravenous, intranasal, intraperitoneal, intracerebral, intraarterial injection or other routes such that a specific binding between an antigen binding site according to the invention with an eptitopic region on the non-functional P2X$_7$ receptor may occur. The antibody/antigen complex may conveniently be detected through a label attached to the antigen binding site or a functional fragment thereof or any other art—known method of detection.

The immunoassays used in diagnostic applications according to the invention and as described herein typically rely on labelled antigens, antibodies, or secondary reagents for detection. These proteins or reagents can be labelled with compounds generally known to those of ordinary skill in the art including enzymes, radioisotopes, and fluorescent, luminescent and chromogenic substances including, but not limited to coloured particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the antigen binding site may be labelled indirectly by reaction with labelled substances that have an affinity for immunoglobulin, such as protein A or G or second antibodies. The antigen binding site may be conjugated with a second substance and detected with a labelled third substance having an affinity for the second substance conjugated to the antigen binding site. For example, the antigen binding site may be conjugated to biotin and the antigen binding site-biotin conjugate detected using labelled avidin or streptavidin. Similarly, the antigen binding site may be conjugated to a hapten and the antigen binding site-hapten conjugate detected using labelled anti-hapten antibody.

In certain embodiments, immunoassays utilize a double antibody method for detecting the presence of an analyte, wherein, the antigen binding site is labelled indirectly by reactivity with a second antibody that has been labelled with a detectable label. The second antibody is preferably one that binds to antibodies of the animal from which the antigen binding site is derived. In other words, if the antigen binding site is a mouse antibody, then the labelled, second antibody is an anti-mouse antibody. For the antigen binding site to be used in the assay described herein, this label is preferably an antibody-coated bead, particularly a magnetic bead. For the antigen binding site to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antigen binding site and the analyte. According to one embodiment of the present invention, the presence of the non-functional P2X$_7$ receptor is determined using a pair of antigen binding sites, each specific for P2X$_7$ receptor protein. One of said pairs of antigen binding sites is referred to herein as a "detector antigen binding site" and the other of said pair of antigen binding sites is referred to herein as a "capture antigen binding site". The antigen binding site of the present invention can be used as either a capture antigen binding site or a detector antigen binding site. The antigen binding site of the present invention can also be used as both capture and detector antigen binding site, together in a single assay. One embodiment of the present invention thus uses the double antigen binding site sandwich method for detecting non-functional P2X$_7$ receptor in a sample of biological fluid. In this method, the analyte (non-functional P2X$_7$ receptor protein) is sandwiched between the detector antigen binding site and the capture antigen binding site, the capture antigen binding site being irreversibly immobilized onto a solid support. The detector antigen binding site would contain a detectable label, in order to identify the presence of the antigen binding site-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antigen binding sites to solid phases are also well known to those of ordinary skill in the art. More recently, a number of porous material such as nylon, nitrocellulose, cellulose acetate, glass fibers and other porous polymers have been employed as solid supports.

The examples that follow are intended to illustrate but in no way limit the present invention.

EXAMPLES

Example 1

Generation and Purification of 2F6 Antibody

Objective:
The experiments described here detail the generation and purification of an antibody that binds to the P2X$_7$ receptor expressed on live cells. In particular, the experiments describe the generation and purification of an antibody with the sequence as shown in SEQ ID NO: 4 (2F6).
Background:
Antigen binding sites that bind a P2X$_7$ receptor monomer are known, however, to date no antibodies are known that bind specifically to conformational epitopes on P2X$_7$ receptors expressed on live cells in a trimer form, specifically spanning the interface between adjacent monomers. The ATP binding sites form at the correctly packed interface between monomers with residues 200-210 on one monomer and residues 296-306 on the adjacent monomer exposed when the receptors are unable to bind ATP as occurs in cancer cells.
Materials and Methods:
Generation of E200 and E300 peptide. The complex peptide epitope E200-300 formed partly from a peptide E200 (residues 200-211 in the human P2X$_7$ receptor sequence) and a peptide E300 (residues 295-306 in the human P2X$_7$ receptor sequence) spaced with the addition of the dipeptide GA was made by solid phase synthesis at Chiron Mimotopes. A range of conjugates were synthesized to identify those most likely to be useful for screening purposes. These included protein conjugates BSA, DT, ovalbumin and KLH linked to the C-terminal Cys reside on the E200-300 peptide via maleimidocaproyl-N-hydroxsuccinimide (MCS). A fourth variant involved biotinylating the E200-300 peptide at the C-terminus.

BALB-C mice were immunized with E200-300 conjugated to diphtheria toxoid (E200-300DT) using 25 ug/dose on days 0, 16, 37, 56, 88 and 162. Day 0 injection was given subcutaneously (sc) in CpG adjuvant (ImmunoEasy, Lot #11547836, 11235150 & 11549008, Qiagen). Day 16, 37, and 88 injections were given half sc and half intramuscularly (im). Day 56 and 162 injections were given intravenously (iv). Four days after final iv boost, the immunized mice were bled and their sera screened for anti-P2X$_7$ E200-300 activity by ELISA. The three animals exhibiting the highest anti-P2X$_7$ E200-300 titre were sacrificed and their spleens removed. Spleen cells were isolated and fused to cells of the mouse myeloma cell line Sp2/0 at a ratio of 5:1. Fused cells were plated in RPMI 1640 medium. Hybridomas were selected successively in HAT followed by HT, supplemented with mouse IL-6. Suitable lead clones were initially identified as ELISA positives in both solid phase and solution phase screens. Low affinity binders were extracted and the DNA then sequenced from the lead clones prior to silencing induced by the effects of the clonal antibody product on the survival of the host cell.

Results:

After plating the fused cells into 8×96 well plates and two cloning steps, by dilution to 0.3 cells per well, one clone reactive with $P2X_7$ E200-300 bovine serum albumin (BSA) conjugate by ELISA, survived and designated 2F6. The clone was sub-cloned and the 24 products designated 2F61-2F24 were each sequenced. The antibodies in each case were IgM class with Kappa light chains.

Each sub-clone was confirmed as having an identical sequence. The VH and VL chains were extracted and spliced into a mouse IgG2a sequence (FIGS. 2 and 3) for the purpose of further molecular development while IgM was grown in mouse ascites for further characterisation.

FIGS. 6A and B show the sequence of the 2F6 scFv labelled with C-terminal FLAG and HIS tags for biochemical characterisations.

The mouse IgG2a-2F6 was grown in parental HEK293 cells transfected with pcDNA3.1-mIgG2a-2F6 carrying G418 resistance. The cells were selected in G418 for 21 days to create the resistant pool.

Stable expression was performed over a seven day batch culture at 37° C. in a Wave bioreactor with a Sartorius 20 L CultiBag. The expression was performed in Invitrogen Freestyle 293 expression medium with pH maintained between 7.3 and 6.8 with CO2 control. The culture was centrifuged to remove the cells and the harvested supernatant processed immediately.

TABLE 6

Cell Culture Summary

| | Process | Result/Comment |
|---|---|---|
| Cell line | HEK293 cells | Stable cell line expressing mouse IgG2a-2F6 |
| Medium | Invitrogen Freestyle 293 | Invitrogen Freestyle 293 |
| Target culture volume | 10 L | 10 L |
| Inoculation density | $0.2 \times 10^6$ cells/mL | $0.2 \times 10^6$ cells/mL |
| Harvest | After 7 day culture duration | $2.9 \times 10^6$ cells/mL 71% viable |

Cell counts performed by trypan blue exclusion on Cedex HiRes, Innovatis

The harvested supernatant was pH-adjusted to 7.1 and 0.2 μm filtered prior to loading overnight onto a 61 mL Protein A column (GE Healthcare, rProtein A Sepharose FF). The column was cleaned with 2CV of 0.1% Triton X-100 followed by sanitisation with 0.1M acetic acid in 20% ethanol prior to use. The antibody was eluted from the column in the reverse direction with a step gradient to 0.1M acetic acid. The eluted peak was neutralised with 1M sodium acetate to pH 5.

TABLE 7

Protein A Chromatography Summary

| | Process | Result/Comment |
|---|---|---|
| Harvested supernatant | pH adjust to 7.1 with 1M Tris, pH 8.3 | Added 10 mL Starting pH = 7.03 Ending pH = 7.08 |

TABLE 7-continued

Protein A Chromatography Summary

| | Process | Result/Comment |
|---|---|---|
| Equilibration | ≥5 CV 1x DPBS, pH ~7.4 | 6.8 CV |
| Load | ≥1 min residence time | 10 mL/min (6.1 min residence time) |
| Wash | ≥3 CV 1x DPBS | 5.3 CV |
| Elution | ≥3 CV 0.1M acetic acid | 3.4 CV |
| Peak | Manually collected | 35 mL |
| Neutralisation | 1.0M sodium acetate | 3.5 mL |

The neutralised peak was 0.2 μm filtered to remove any particulates before anion exchange. The filtered neutralised peak was loaded onto a 54 mL anion exchange column (GE Healthcare, Q Sepharose FF). The column was cleaned and sanitised with 0.5M sodium hydroxide prior to a high salt wash and equilibration in 0.1M acetic acid, pH 5.0. The running buffer was 0.1M acetic acid, pH 5.0. The flowthrough from the anion exchange step was collected.

TABLE 8

Anion Exchange Chromatography Summary

| | Process | Result/Comment |
|---|---|---|
| High salt wash | ≥1 CV 0.1M acetic acid, 2M NaCl, pH 5.0 | 1 CV |
| Equilibration | ≥5 CV of 0.1M acetic acid, pH 5.0 | 5.3 CV |
| Load | Not specified | 10 mL/min (5.4 min residence time) |
| Flowthrough | Manually collected | 64.8 mL |
| Concentrated product | Ultrafiltration retentate | 23 mL |

The concentrated anion exchange flowthrough was loaded directly onto a 140 mL desalting column (GE Healthcare, Sephadex G-25 fine). The column was cleaned and sanitised with 0.2M sodium hydroxide prior to equilibration in 1xDPBS. The running buffer was 1xDPBS.

In a biosafety cabinet, the desalted product was filtered through a 0.2 μm filter into a sterile container. Final product samples were aseptically removed from the filtered bulk. The filtered bulk and final product samples were stored at 4° C.

TABLE 9

Buffer Exchange Summary

| | Process | Result/Comment |
|---|---|---|
| Equilibration | 1x DPBS, pH ~7.4 (until conductivity plateaus and pH is neutral) | As standard |
| Load | Maximum 28 mL | 23 mL loaded |
| Peak | Manually collected | 39.9 mL |
| Filtration | 0.2 μm filter in biosafety cabinet | Millex GV, 0.22 μm PVDF syringe filter, 33 mm |
| Final product | Mass or volume | 37.6 mL |

The final product was assayed for protein concentration, endotoxin, DNA content, purity and aggregation. The product was stored at 4° C. before analysis.

TABLE 10

Summary of assay results for final product

Figure 7:
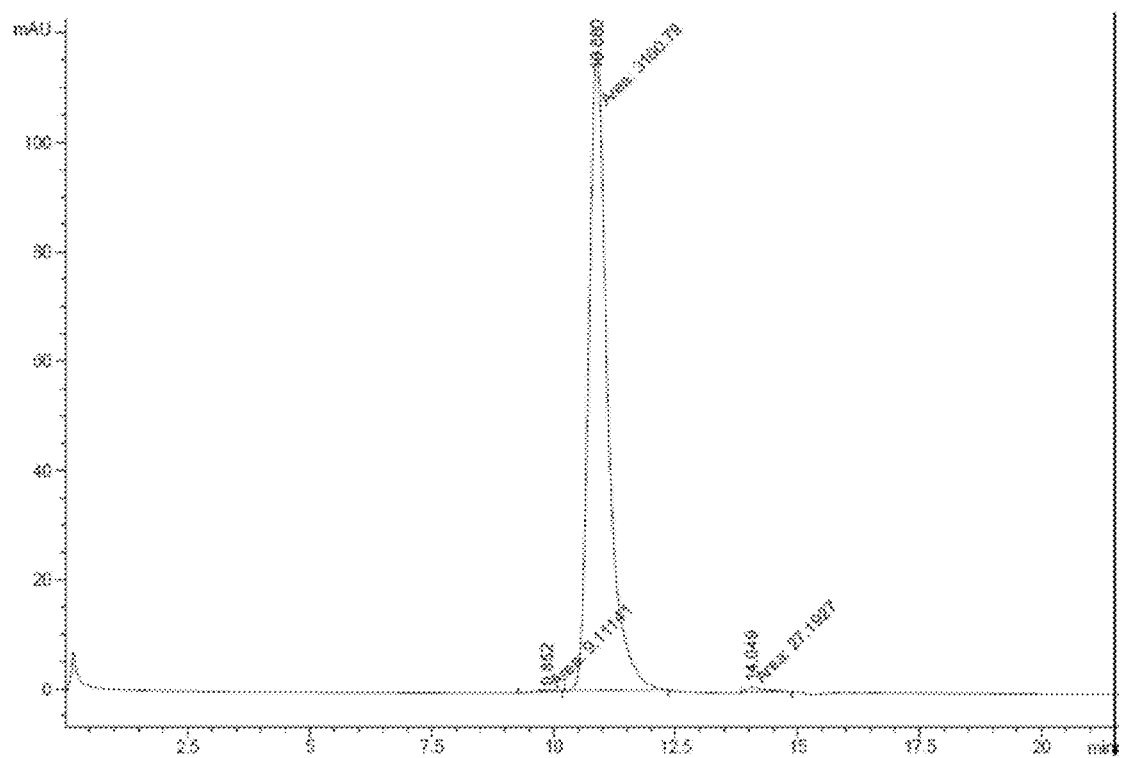
FIG. 7. HP-SEC of 2F6 mIgG2a purification.
Figure 8:
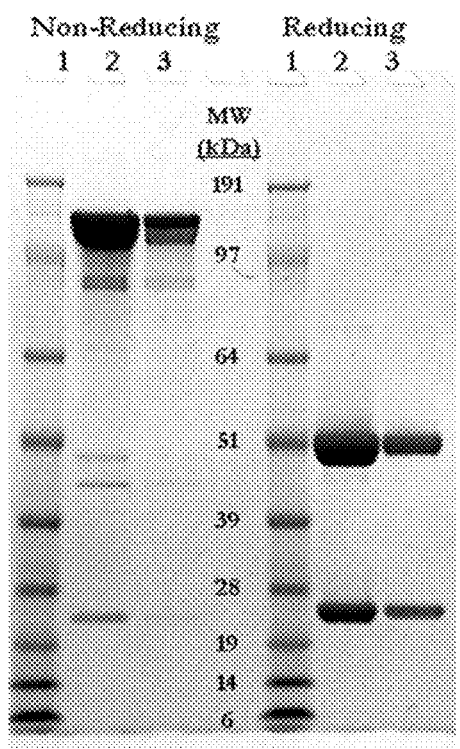
FIG. 8. SDS PAGE showing purity of the final antibody product.
Figure 9A:
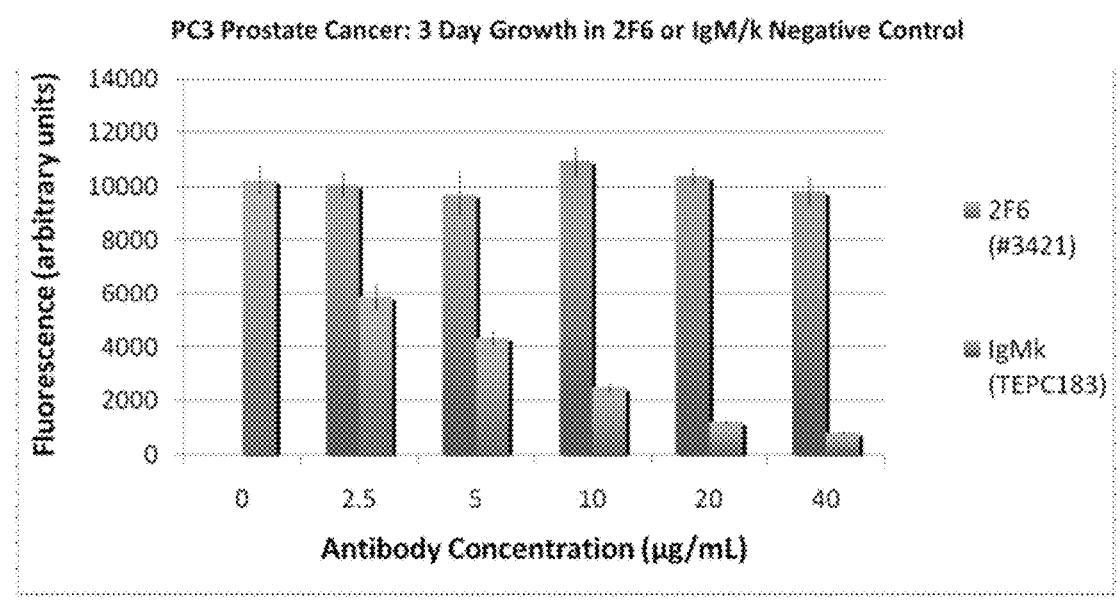
FIGS. 9A-E. (A) In Vitro Cell Inhibition Assays. The IgM form of the original antibody to the trimer form of the non-functional P2X$_7$ receptor expressed on cancer cells was found to inhibit cell growth using the Cell Titer Blue Assay. An example is shown in which the control IgM antibody is seen to have no effect on cell growth (left columns) for increasing concentrations from 2.5 to 40 ug/mL while the 2F6 inhibited cell growth (right columns) over the same dose range in a 3 day growth assay. (B), (C), (D) Other cell types were similarly inhibited by incubation with the IgM form of the antibody. Growth over 5 days is inhibited to a greater extent than over 3 days. The growth data is plotted relative to the control growth curves obtained using the control IgM antibody. COLO205 growth was significantly inhibited over 3 days and the cells were eliminated over 5 days even at low dose of 2.5 ug/mL. This indicates that different cell lines expressing slightly different levels of receptor are more or less susceptible to the antibody binding. (E) In contrast, the recombinant IgG2a form of the antibody showed weaker cell inhibition as shown in the following figures obtained over 3 days. The cell growth inhibition assay (Cell Titer Blue) showed the IgG$_{2a}$ form of the antibody had reduced tumour cell growth inhibition compared with the inhibition elicited using the IgM form of the antibody, in line with the reduced binding affinity of the IgG containing as it does, two binding domains rather than ten.
Figure 9B:
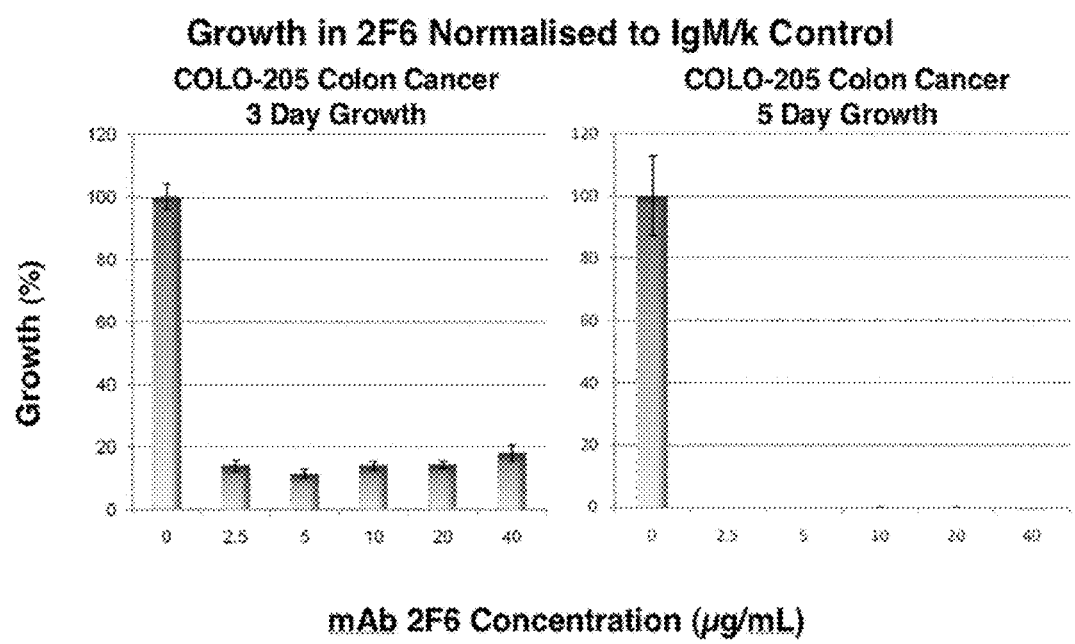
Figure 9C:
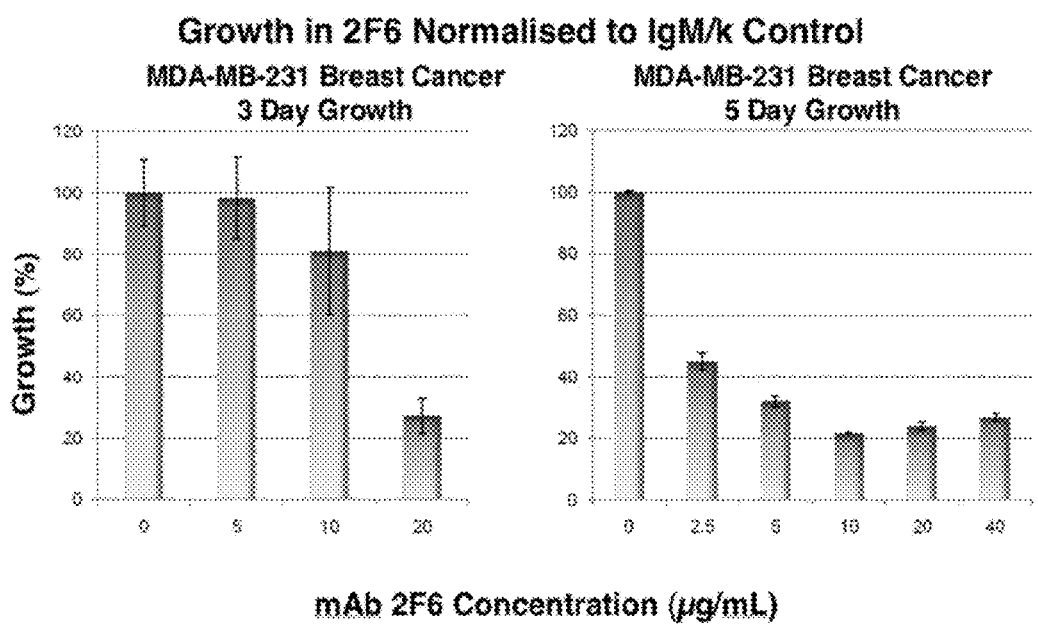
Figure 9D:
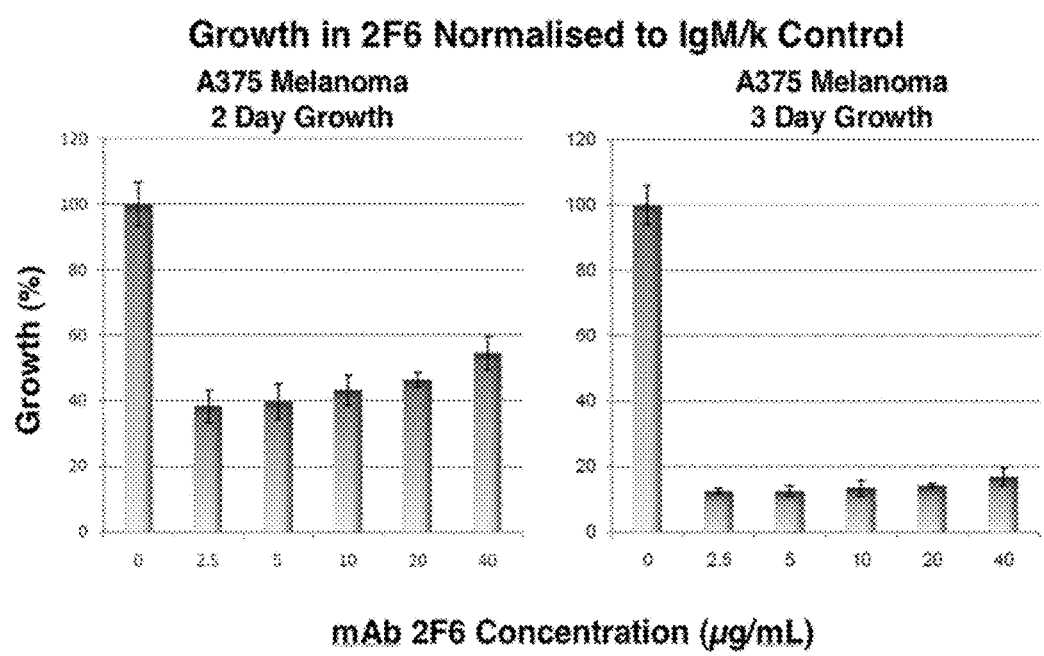
Figure 9E:
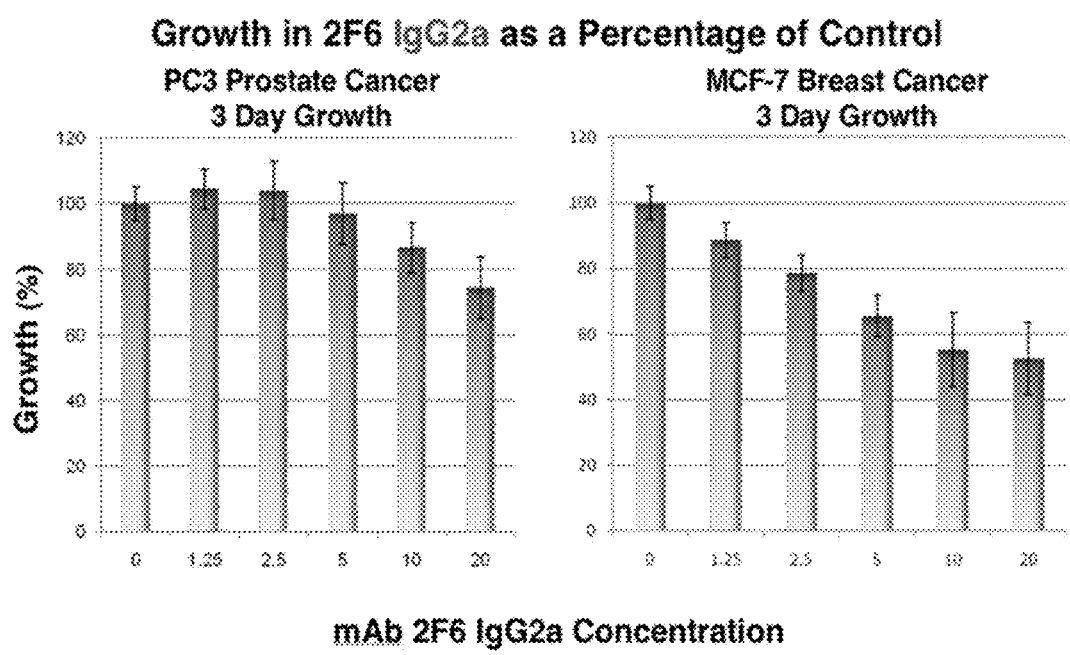
Figure 10:
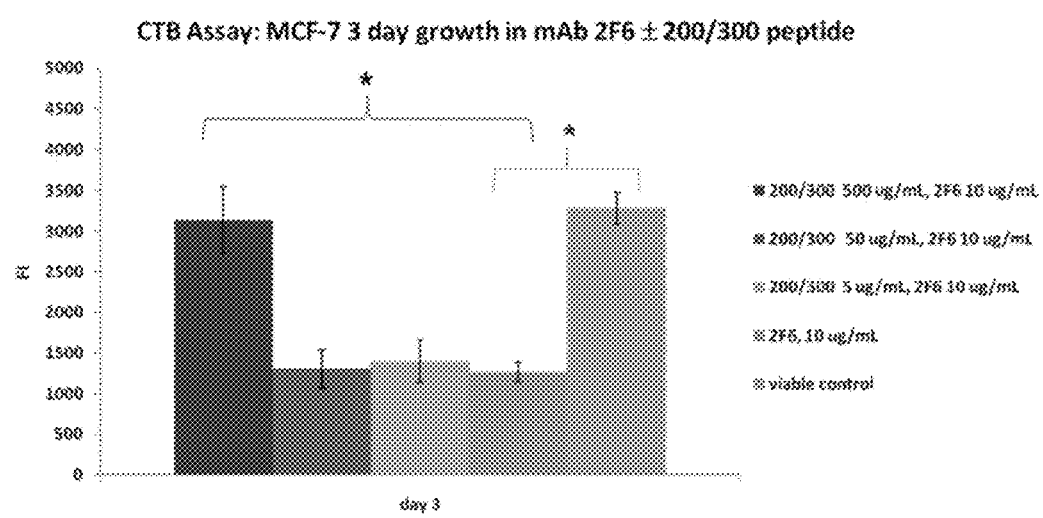
FIG. 10. Blocking Reaction in Cell Killing Assay. The Cell Titer Blue cell growth inhibition assay is used over three day cell growth with MCF-7 breast cancer cell line. Note the viable control cells in the right column have no antibody or peptide. The left hand column is the signal derived from the cells incubated with 10 ug/mL 2F6 IgM antibody containing 500 ug/mL peptide epitope (E200-300 epitope described as 200/300 in Figure), sufficient to block the cell growth inhibition evidenced by the data in the three central columns that show growth inhibition is not affected by the presence of 50 ug/mL, 5 ug/mL or 0 ug/mL peptide respectively. Total inhibition of cell growth occurs after 5 days of 2F6 exposure.
Figure 11:
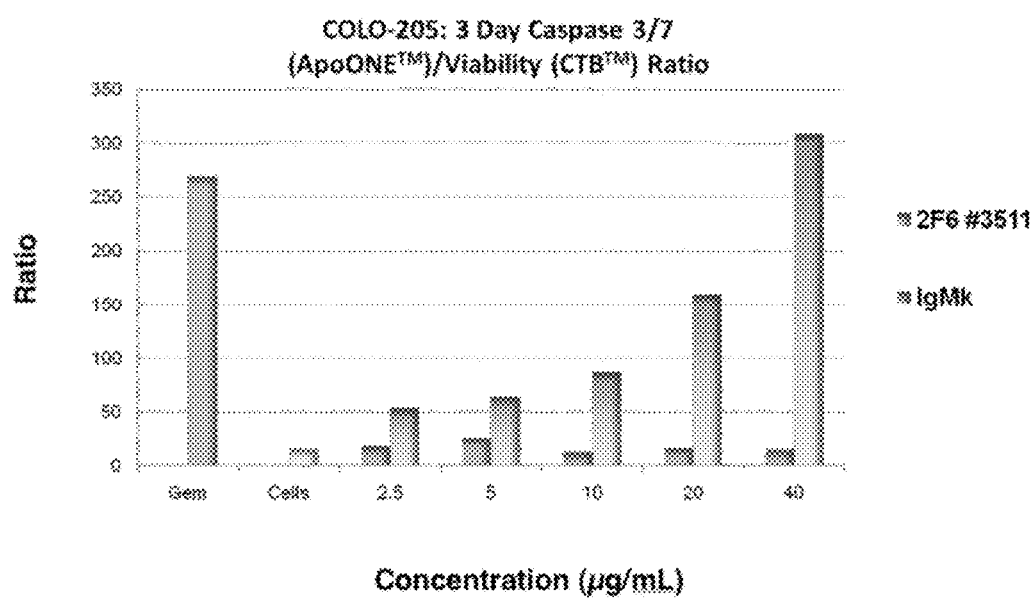
FIG. 11. Mechanism of Cell Death Induced by 2F6 with Caspase 3/7 Activation Associated with Reactivation of Apoptosis. In this experiment the effect of the Gemcitibine control drug is shown at the left, known to activate caspases through induction of apoptosis in COLO205 cancer cells. In contrast, the absence of drug or antibody has no effect (cells only column). The presence of control IgM at doses up to 40 ug/mL similarly has no effect on caspase activation while increasing amounts of 2F6 antibody shows a steady increase in Caspase 3/7 activation associated with apoptosis induction by the antibody over the 3 day time course of the experiment.
Figure 12:
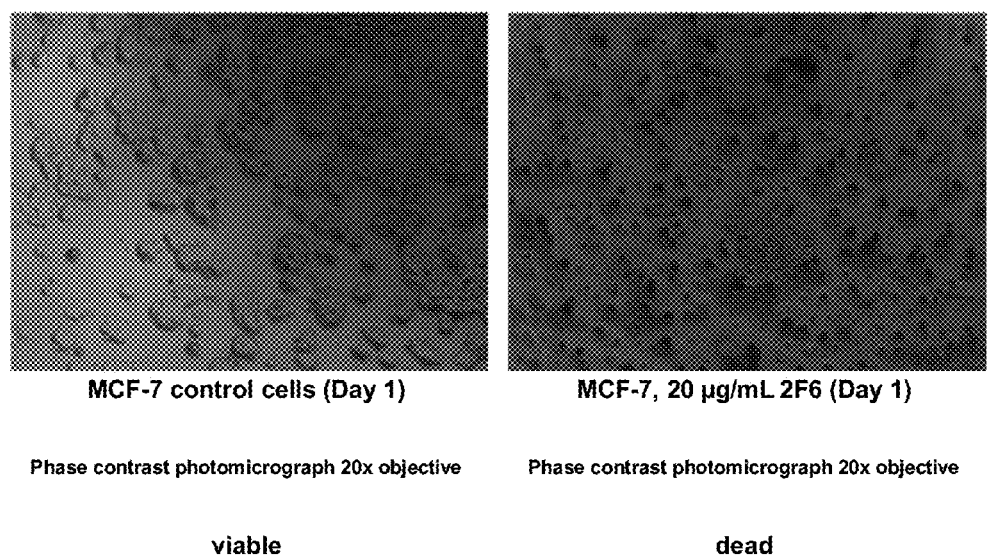
FIG. 12A-B. Direct Cell Killing by 2F6 IgM. Confocal microscope images of MCF-7 cells in presence of control IgM antibody (A) and 2F6 IgM (B) for 24 h.

| Test | Test Method | Specification | Result | Pass/Fail |
|---|---|---|---|---|
| Protein Concentration | Absorbance at 280 nm, EC = 1.4 | ≥1.0 mg/mL | 1.6 mg/mL | Pass |
| DNA | Invitrogen Quant-iT PicoGreen kit | ≤380 ng/mL | 15 ± 1 ng/mL | Pass |
| Endotoxin | Charles River Endosafe PTS 0.05-5 EU/mL cartridge | <3 EU/mL | 0.121 EU/mL (0.076 EU/mg) | Pass |
| Aggregation and purity | SE-HPLC TOSOH Biosciences TSKgel G3000 SWXL | ≤5% aggregation ≥95% pure | <1% aggregate >98% pure (FIG. 7) | Pass |
| SDS-PAGE | NuPAGE 4-12% Bis-Tris gel, MOPS buffer, SimplyBlue Safe Stain | For information | (FIG. 8) | N/A |

The same mouse scFv from 2F6 was grafted into a human format of type IgG1 and similarly expressed in HEK293 cells.

Conclusion:

Antigen binding sites in the form of leads for high affinity binding to $P2X_7$ receptors on live cells were identified. The antigen binding sites were selected to span the interface between adjacent monomers forming the trimeric receptor when exposing the underlying ATP binding site in non-functional receptor conformation. The target compound epitope was to remain inaccessible on the single conformation of the function-capable assembled receptor in order to avoid all cross-reactivity with normal cells expressing $P2X_7$ receptor.

Example 2

Biochemical Characterisation of 2F6 Antibody Forms

Objective:

To determine whether the 2F6 antibody forms, including the IgM and mouse IgG2a, bind to non-functional receptors on the surface of live cells. Also, to determine whether the 2F6 antibody forms inhibit a property of a cell, for example a cancer cell, that expresses non-functional $P2X_7$ receptors.

Background:

It is known that cancer cells express non-functional receptors that consist of a trimer of $P2X_7$ receptor monomers. When able to function, the assembled $P2X_7$ receptors on the cell surface bind ATP with the effect that the channel formed between the monomers assembled into a trimer undergoes a transition to a wider pore able to greatly increase the ingress of calcium ions into the cell to initiate caspase activity leading to apoptosis and cell death. Apoptosis is withheld or inhibited in cancer cells that are unable to die even though the $P2X_7$ receptor is deployed on the cell surface. These receptors are termed non-functional $P2X_7$ and have been found on a wide variety of cancers.

Results:

The 2F6 antibody forms, both IgM (FIGS. 9A-D) and IgG2a (FIG. 9E), inhibited cell growth in a range of cancer cell lines including prostate PC3, colon COLO205, breast MDAMB231, melanoma A375 and breast MCF7 as determined in a Cell Titer Blue assay of cell growth. Cells were seeded at appropriate density and grown over a 3-day or 5-day period to reach a level close to confluence at the end of the test period in the presence of control antibodies and in the presence of test antibodies, either IgM or IgG2a types of 2F6 over the concentration range 0-40 ug/mL. Testing of cell line growth was conducted with seed densities ranging from 100-2000 cells/well. Compared with the control antibodies that had no effect on the growth of the various tumour cell types, an increasing concentration of either IgM or IgG2a types of 2F6 inhibited cell growth.

FIG. 10 shows data from MCF7 cell growth in the presence or absence of 10 ug/mL of 2F6 IgM antibody. The presence of the antibody greatly inhibits cell growth over 3 days while pre-incubation of the antibody with soluble peptide epitope at 5-50 ug/mL has no effect on the inhibition. However, at 500 ug/mL peptide, the antibody is no longer able to affect cell growth as the peptide effectively sequesters the available antibody, precluding it from binding to the receptors on the cell surface.

A mode of action by which the 2F6 is able to inhibit cell growth was determined by an ApoOne apoptosis assay in which caspase 3/7 activity was measured in combination with cell growth through the Cell Titer Blue assay. Colo205 cells were grown in a 3-day growth assay with increasing 2F6 from 0-40 ug/mL. The gemcitabine positive control was added to establish the degree of apoptosis that may be elicited by the presence of bound antibody. FIG. 11 clearly reveals apoptosis is initiated in the presence of increasing antibody, with 20-40 ug/mL sufficient to initiate full activity.

The appearance of MCF7 cells grown in 20 ug/mL of the 2F6 IgM compared with control antibody that does not bind to the cells is shown in the confocal images in FIG. 12 in which many cells are already dead after just 24 hours exposure.

Conclusion:

The interaction of 2F6 antibody forms, both IgM and IgG2a, with non-functional $P2X_7$ receptors on cancer cells causes inhibition of cell growth and induction of apoptosis and cell death.

Example 3

Binding of Antibody to Live Tumour Tissue

Objective:

To establish whether antibodies directed at a unique accessible composite epitope spanning adjacent monomers within the $P2X_7$ trimer expressed on cancer cell surfaces are more capable of differentially binding to the target on the surface of live cancer cells compared with residual target on dead cancer cells.

Background:

The 2F6 antibody binds across adjacent monomers in expressed $P2X_7$ receptors on cancer cells but not on receptors that are expressed on normal cells expressing functional or function-capable $P2X_7$ receptors such as those on white and red blood cells. An antibody able to specifically bind non-functional $P2X_7$ receptors by targeting an epitope confined to a monomer of the receptor is also able to bind to such monomeric targets that may be released from the cytoplasmic compartment of dead cells, thereby reducing therapeutic potential as it becomes partially bound by $P2X_7$ receptors from dead cells in addition to $P2X_7$ receptors from live cells necessitating an increase in effective dosage.

Materials and Methods:

Female BALB/c mice inoculated with the orthotopic syngeneic 4T1 murine mammary tumours in their third mammary fat pads or NOD/SCID female mice inoculated with the orthotopic human Hep3b xenograft tumour in their livers were treated intravenously with either a human domain antibody (2-2-1 hFc) directed at a monomeric target (epitope E200 on $P2X_7$) or 2F6-hIgG1 directed at the compound epitope E200-300. All procedures approved by the Animal Ethics Committee at The University of Adelaide (M46-2008). Antibody penetration into the tumours was measured using Jackson Immunosearch goat anti-human antibody on tumour sections that were removed from the mice two days post antibody treatment. The tumours were fixed in 10% neutral buffered formalin for 48 hours, embedded in paraffin, sectioned to 5 um, deparaffinized, and stained for human antibody. The Biocare Mach 4 secondary detection system was used, comprising a specific goat antibody probe followed by a polymer with HRP then stained with DAB.

Figure 13A:
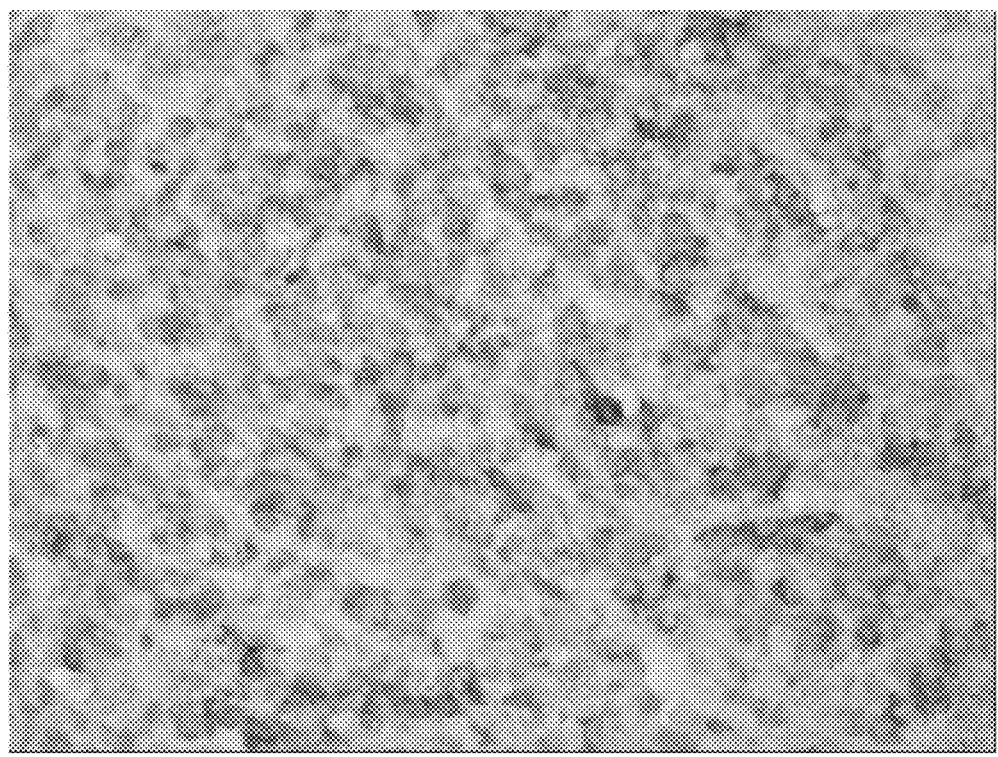
FIGS. 13A-D. (A) 2-2-1hFc bound to live 4T1 tumour cells showing some membranous binding (×40 obj). (B) 2-2-1hFc bound to dying cells along with membranous debris from cells already killed. (C) 2-2-1 hFc bound to live LL tumour cells showing clear membranous binding. (D) 2-2-1hFc bound to membranous debris from cells already killed.
Figure 13B:
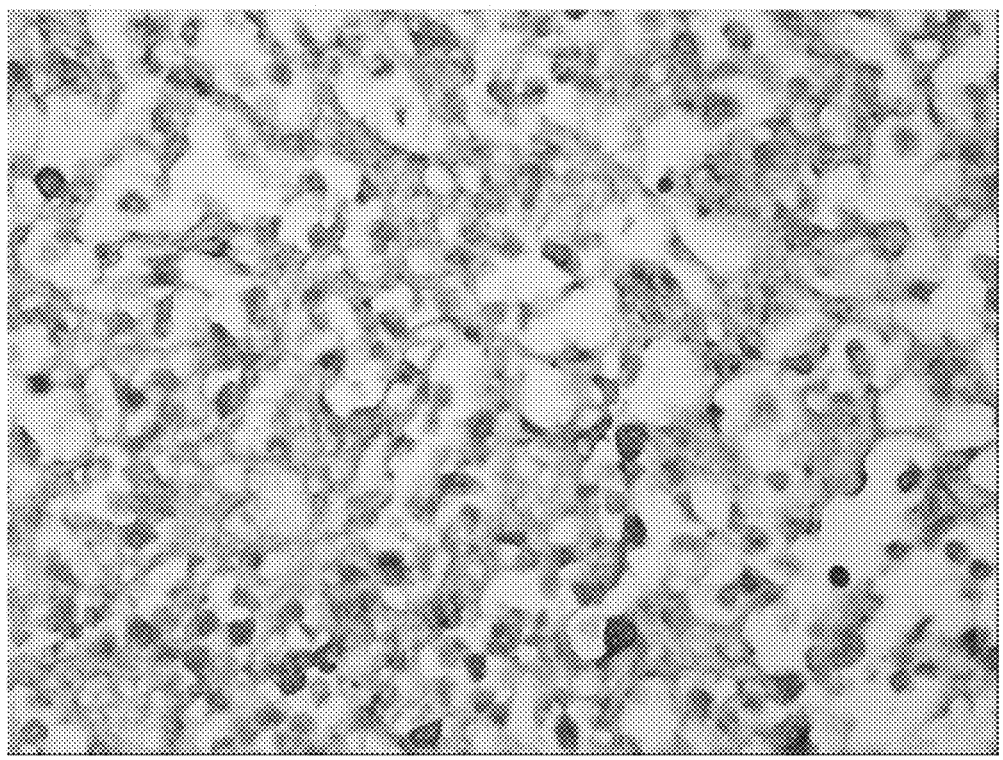
Figure 13C:
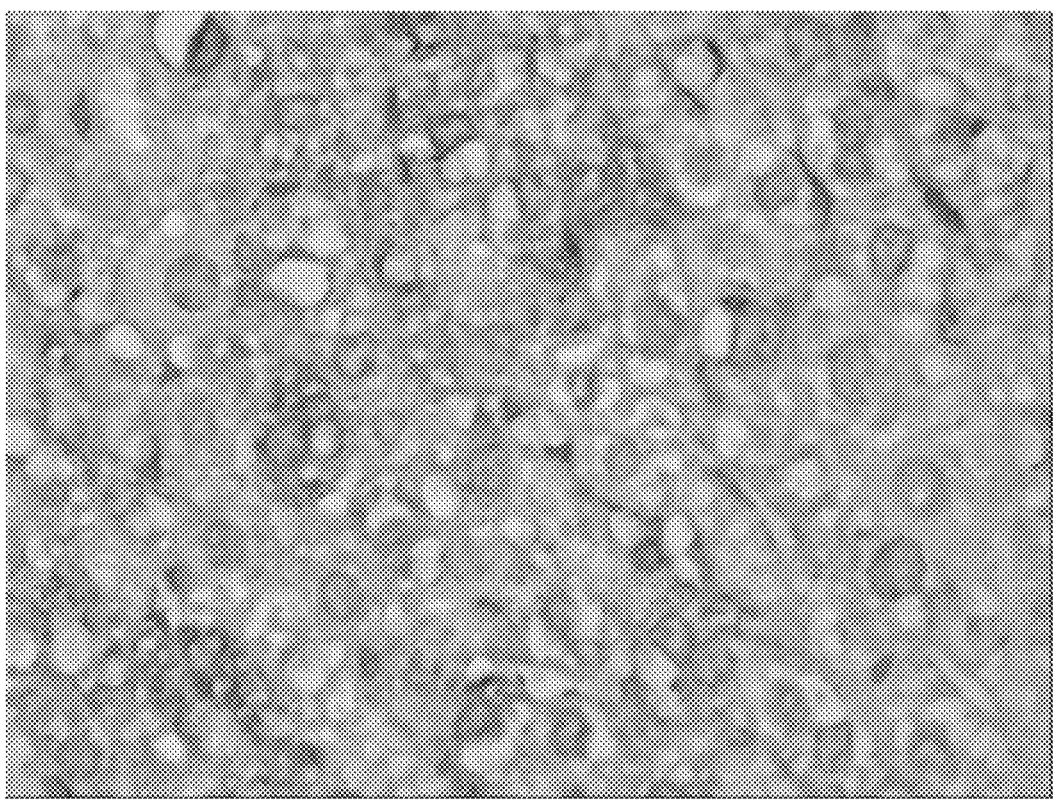
Figure 13D:
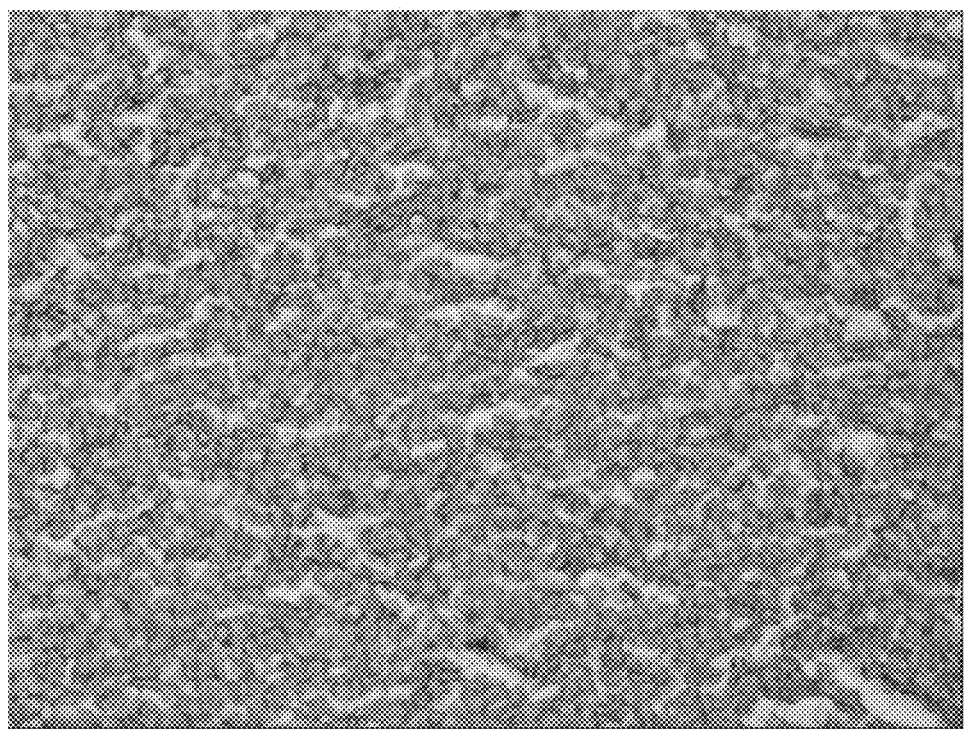

Results:

Antibodies that target the monomer binding site E200 within the trimer bind live cells within the 4T1 tumours (FIG. 13A) although they similarly bind to cells that are dead and dying along with cellular debris (FIG. 13B). In the case of the Lewis Lung tumours, binding to live cells (FIG. 13C) appears moderate and membranous but cells already destroyed (FIG. 13D) remain capable of sequestering such antibodies (2-2-1 hFc).

Figure 14A:
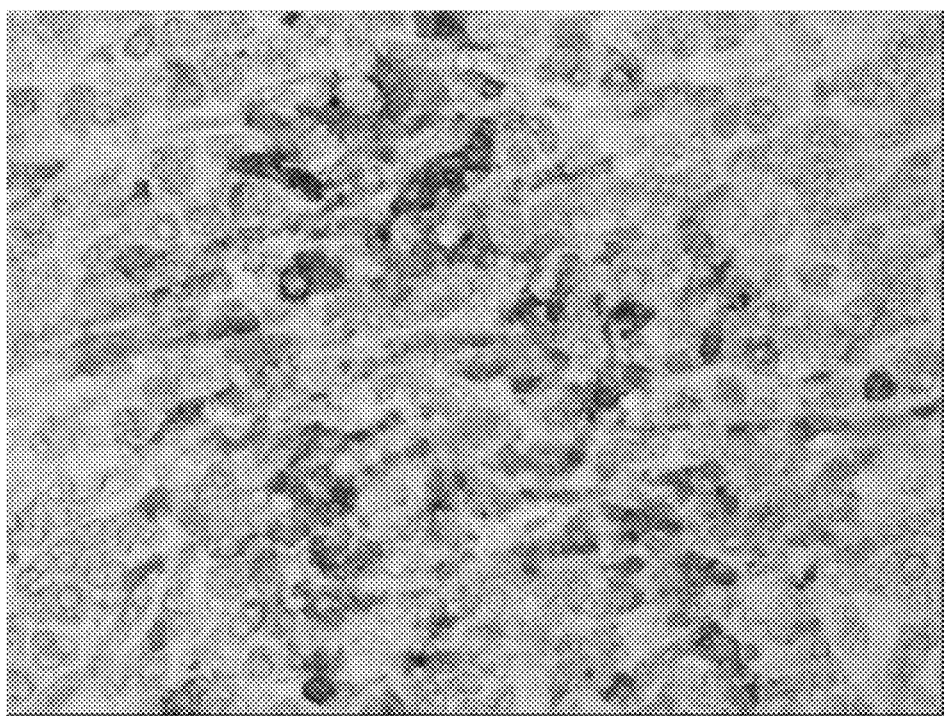
FIGS. 14A-D. (A) 2F6 hIgG1 bound to live 4T1 tumour cells showing clear membranous binding (×40 obj). (B) 2F6 hIgG1 bound only to dying cells. (C) 2F6 hIgG1 bound to live LL tumour cells showing clear membranous binding. (D) 2F6 hIgG1 bound to dying cells with no binding to adjacent red blood cells expressing function-capable P2X$_7$ receptor.
Figure 14B:
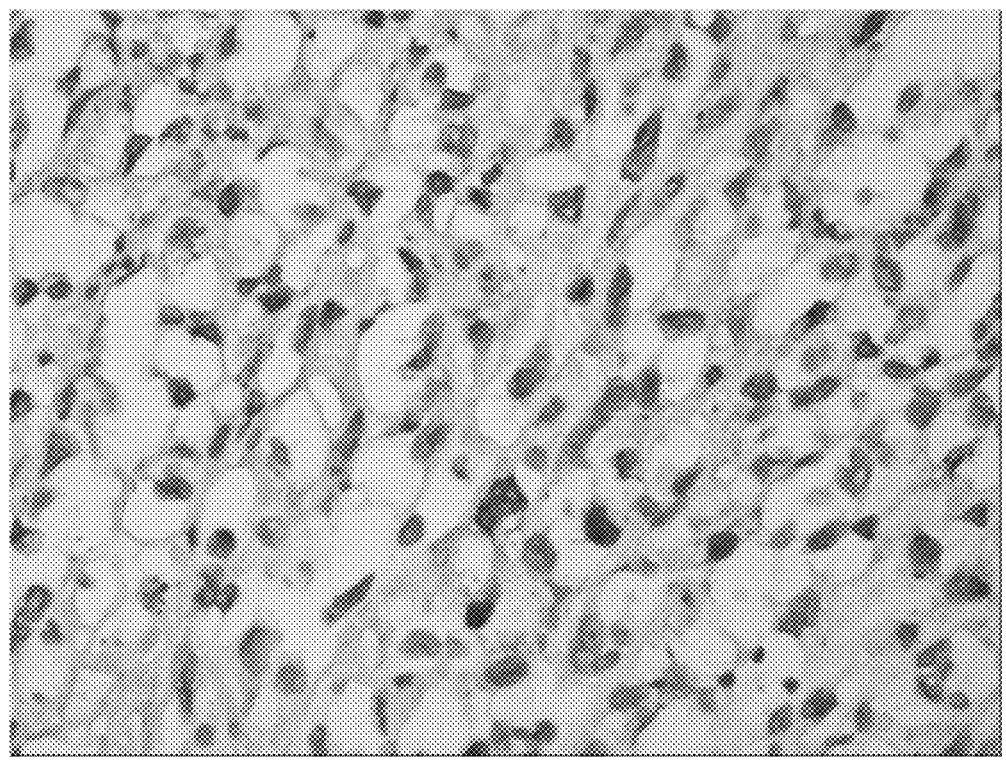
Figure 14C:
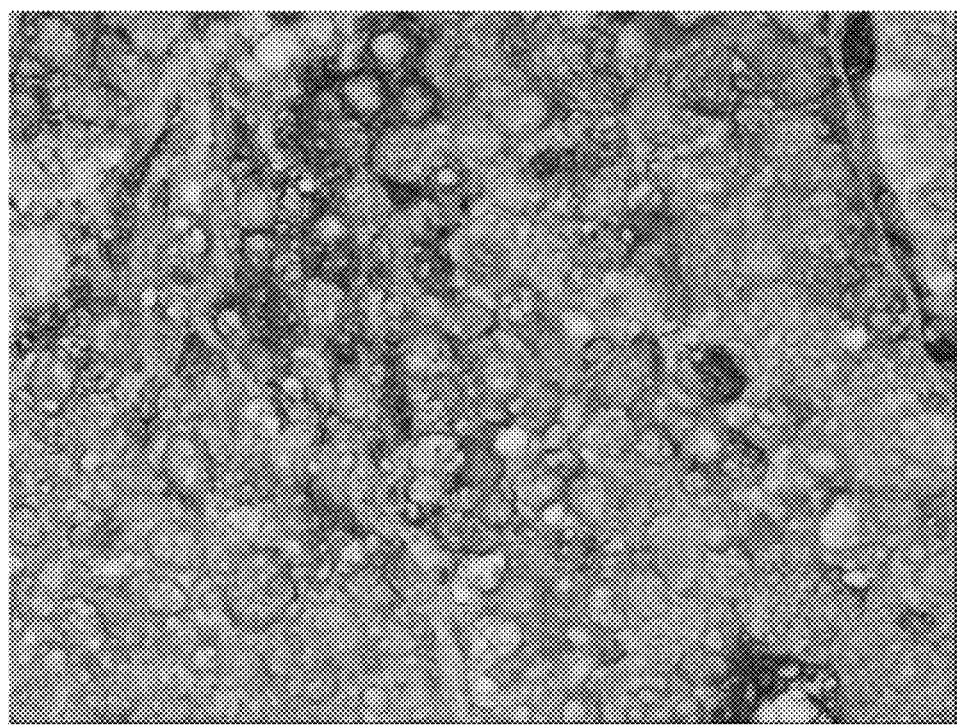
Figure 14D:
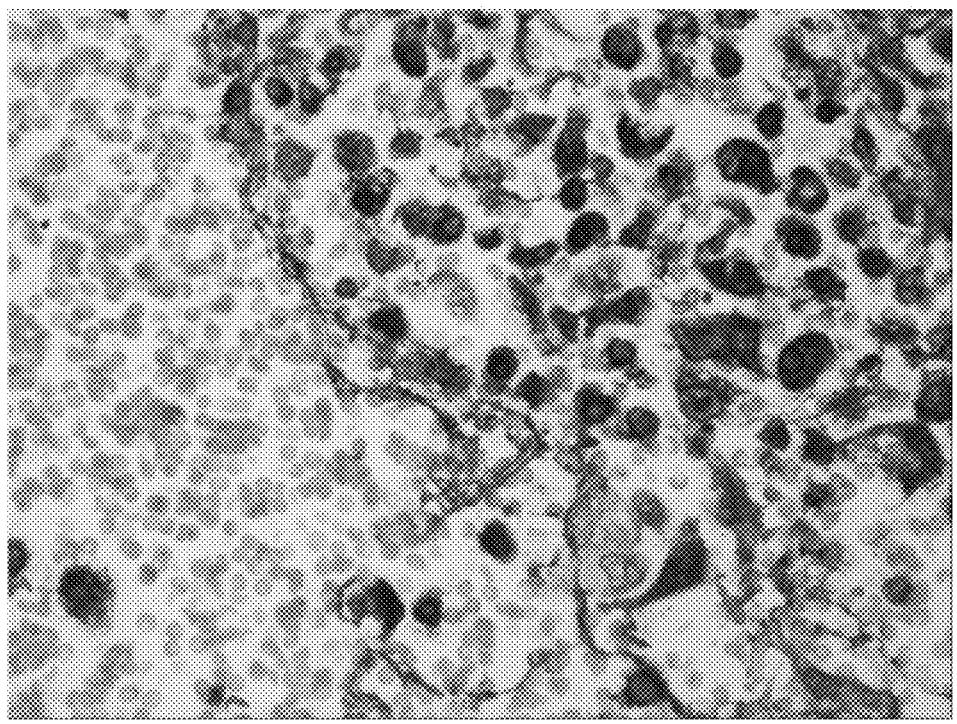

The same tumour types were investigated for residual live and dead cell binding using 2F6 hIgG1. Binding to live cells in 4T1 showed clear membranous label (FIG. 14A) and in contrast with the 2-2-1hFc monomeric binder, the antibody binding to the interface between monomers was largely inhibited from binding to cellular debris although it remained bound to dying cells (FIG. 14B). Similarly the binding to Lewis Lung tumours showed strong membranous binding (FIG. 14C). Dying cells had residual antibody label but cellular debris remained clear (FIG. 14D). The figure also shows red blood cells that remain entirely unlabelled, even though they express $P2X_7$ receptors, although in a function-capable conformation that does not expose the E200-300 epitope to the antibody.

Conclusion:

Antigen binding sites were produced such that an antibody directed against the complex target spanning the inter-monomer interface had an advantage over antibodies confined to a binding site on the monomer in that much less of the 2F6 antibody was misdirected by binding to cellular debris created from the death of live cells thereby reducing the required therapeutic dose.

Example 4

Therapeutic Efficacy of 2F6 hIgG1

Objective:

The therapeutic efficacy of 2F6 hIgG1 was determined in mouse xenograft tumour models and compared with a high affinity sheep polyclonal antibody raised to the same target and affinity purified.

Background:

Antibodies directed at the monomeric epitope target E200 in non-functional $P2X_7$ expressed on cancer cells have exhibited therapeutic effects of tumour cell killing and tumour growth inhibition. These therapeutic antibodies bound in the sub-nanomolar range, two logs higher binding constant than 2F6 hIgG1 exhibits. A similarly high affinity sheep polyclonal antibody was developed against the same compound E200-300 epitope to examine the likely efficacy of an antibody of the form of 2F6 after affinity maturation to improve the binding constant.

Materials and Methods:

Reagents for culture of 4T1 mouse breast tumour cells were obtained from the following suppliers: RPMI 1640 cell culture medium, FCS, Glutamax, HBSS and penicillin-streptomycin from Invitrogen Australia (Mt Waverley, VIC, Australia); and Trypan Blue from Sigma-Aldrich (Castle Hill, NSW, Australia). Matrigel™ was obtained from BD Biosciences (North Ryde, NSW, Australia).

Sterile saline (0.9% aqueous sodium chloride solution) was obtained from Baxter Healthcare Australia (Old Toongabbie, NSW, Australia). Phosphate buffered saline (PBS) was obtained from Sigma-Aldrich. Formalin (10% neutral buffered formalin) was obtained from Australian Biostain (Traralgon, VIC, Australia).

Materials for haematoxylin and eosin staining of tumour sections were obtained from the following suppliers: Superfrost Plus slides from Menzel (Germany); Alum haematoxylin and eosin from HD Scientific (NSW, Australia); Ethanol, concentrated hydrochloric acid and lithium carbonate from Sigma Aldrich; DePex mounting medium from BDH (UK).

Tumour cells were sourced from American Type Culture Collection (ATCC) (Rockville, Md., USA).

Tumour cells (Passage 2 from working stock) were cultured in RPMI 1640 cell culture medium, supplemented with 10% FCS, 1% Glutamax and 1% penicillin-streptomycin. The cells were harvested by trypsinisation, washed twice in HBSS and counted. The cells were then resuspended in HBSS:Matrigel™ (1:1, v/v) to a final concentration of $5 \times 10^7$ cells/mL.

Dosing occurred every 3 days at antibody concentrations of 1 or 10 mg/kg i.v. or with PBS for treatment control or Sorafenib at 5 mL/kg daily as a positive control in the Lewis Lung model. Mice were randomised into equal groups of 10 mice, based on tumour volume on Day 0 of the studies.

Any animal was to be removed from the study if its tumour volume reached 2,000 mm³. Treatment of any animal would cease if its body weight dropped to below 85% of that on entry into the study. Animals would also be culled if severe adverse reaction to the treatment was observed.

Mice were anaesthetised for blood collection and euthanised by exsanguination via terminal cardiac bleed 48 hours post-final dose, on Days 11 or 14 post-initial treatment.

Whole blood was collected via cardiac puncture from all mice in all groups at termination.

Blood samples were allowed to clot at room temperature for 30 minutes followed by 2 hours at 4° C., then centrifuged (2000×g) for 15 minutes at 4° C. The serum component was collected into fresh cryovials and stored at −20° C.

The tumour was excised from all mice in all groups, weighed and preserved in 10% neutral buffered formalin.

The lungs were excised from all mice. Lung surface metastases were counted and were categorised according to size: small (<1 mm), medium (≥1 mm and <3 mm) and large (≥3 mm). Excised lungs were preserved in 10% neutral buffered formalin.

All statistical calculations were performed using SigmaStat 3.0 (SPSS Australasia, North Sydney, NSW, Australia).

A paired t-test was used to determine the significance in body weight change within a treatment group between Day 0 and the final measurement day for the group. Only those mice surviving until termination day were included in the analysis.

A t-test was performed on tumour weights, histological tumour size, and lung and liver metastases counts in all animals.

A One-Way Analysis of Variance (ANOVA) was performed on tumour weights, histological tumour sizes, and lung and liver metastases counts on all groups surviving until the termination days of the studies (Day 14 for 4T1 and Day 11 Lewis Lung)

Where significant differences were found using the One Way ANOVA, Multiple Comparison versus Control Group Procedures (Holm-Sidak Method) were performed. The Pre-immune Control (Group 2) was used as the control group on Day 9. As the mice in this group had died the Vehicle Control (Group 1) was used as the control group on Day 14. Although in some cases the data failed the Normality Test or Equal Variance Test, statistical analyses were performed using absolute values.

A p value of less than 0.05 was considered significant.

Figure 15:
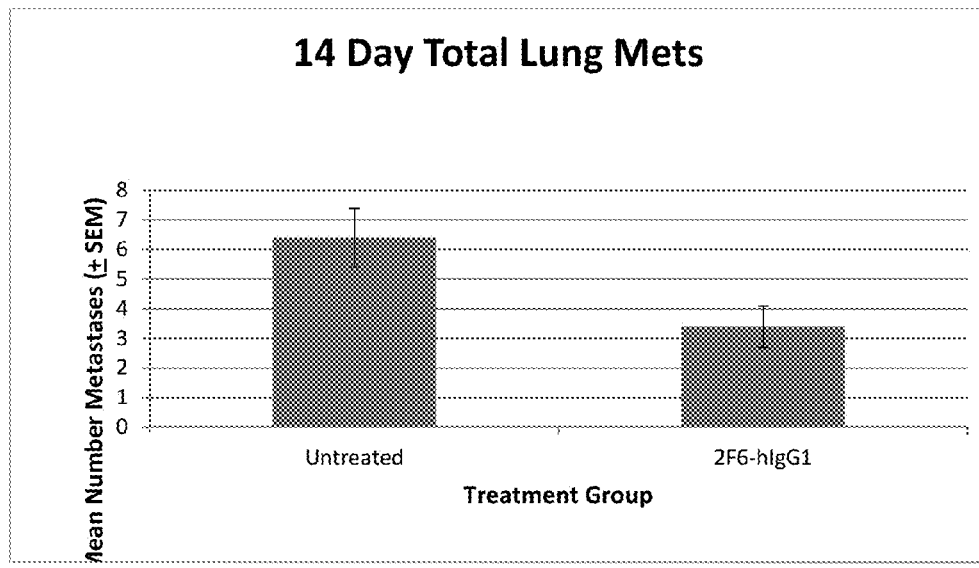
FIG. 15. Inhibition of the number of lung metastases by Day 14 in the 4T1 syngeneic xenograft model by 2F6hIgG1. The overall reduction in tumour volume was 89% with most metastases in the treatment group much smaller than in the untreated group.

Results:

After 14 days the 4T1 mouse lungs were excised from the BALBc mice to measure the number of lung metastases. The control group of 10 mice had 6.4±1.0 while the 2F6-hIgG1 treated group showed 3.4±0.7 or 53% of control as shown in FIG. 15. The average metastasis volume in the two groups was further reduced from 5.77 to 1.28 mm$^3$ or 22% and the total metastasis volume reduced by 88% from 369 to 43 mm$^3$ or 11.8% of control.

The syngeneic Lewis Lung model was used with additional control groups. Besides the PBS control group of ten mice (Group 1), a positive control group using daily Sorafenib at 5 mL/kg was included (Group 5) along with antibody treatment groups consisting of sheep affinity purified E200-300 polyclonal antibody at 10 mg/kg (Group 2), 2F6-hIgG1 at 1 mg/kg (Group 3) and 2F6-hIgG1 at 10 mg/kg (Group 4). The results obtained were:

|  | Mean Lung Surface Mets | SEM |
| --- | --- | --- |
| Group 1 | 2.3 | 0.4 |
| Group 2 | 0.1 | 0.1 |
| Group 3 | 0.9 | 0.2 |
| Group 4 | 0.2 | 0.1 |
| Group 5 | 0.1 | 0.1 |

Figure 16:
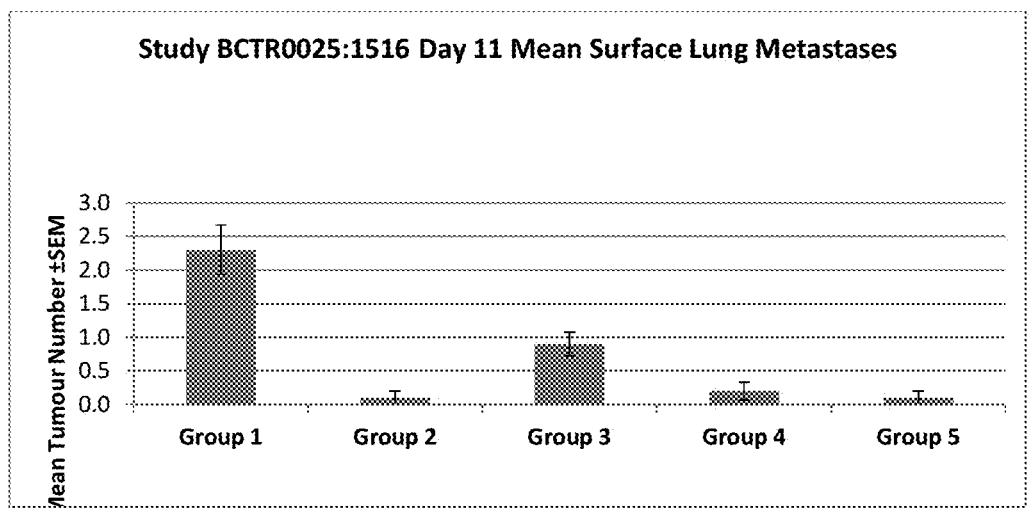
FIG. 16. Inhibition of the number of lung metastases in the Lewis Lung (LL) syngeneic xenograft model by Day 11. The five groups are the untreated control (Group 1), sheep polyclonal E200-300 at 10 mg/kg (Group 2), 2F6IgG1 at 1 mg/kg (Group 3) and at 10 mg/kg (Group 4) and Sorafenib at 5 mL/kg daily (Group 5). Both sheep polyclonal and 2F6 hIgG1 were equipotent with Sorafenib with 96% inhibition.

These results are summarised in FIG. 16. The reduction in tumour metastases between the control Group 1 and all other groups is significant at p<0.001. The high affinity sheep antibody inhibited tumour formation equally well with the much lower affinity monoclonal 2F6 at 10 mg/kg, both equal to the Sorafenib positive control, all 96% inhibition relative to PBS control.

Conclusion:

The targeted complex inter-monomer epitope binding site is accessible on tumour cells. Antibodies with a Kd ranging from 0.5 nM (sheep affinity purified polyclonal) to 50 nM (2F6-hIgG1) show similar efficacy, suggesting an optimum binding constant for a human therapeutic is in the low nM range.

Example 5

Generation and Purification of Affinity Matured Antigen Binding Sites

Objective:

The experiments described here were to develop antibody forms (i.e. scFv/Fab) that exhibited increased binding constants to improve both the specific binding to the non-functional P2X$_7$ receptors on cancer cells without binding functional receptors on any normal cells such as lymphocytes and thus obtain inhibition of cancer cell growth at a lower antibody concentration than was achieved with the WT recombinant 2F6 monoclonal.

Background:

The 2F6 antibody forms exhibited specific binding to P2X$_7$ receptors on live cancer cells however for use as a diagnostic or therapeutic an antibody may require improved affinity.

The CDR3 sequence HYSSRFFDV from 2F6 was used as a starting point for iterative rounds of randomization and screening because it was thought most likely to yield antibody leads with increased affinities that could be explored for test purposes in therapeutic test models.

Materials and Methods:

The 2F6 VH and VL gene fragments were amplified and assembled into an E. coli expression/secretion vector. Both the 2F6 scFv and Fab were transformed into E. coli and expression of the gene construct induced. The E. coli cultures were harvested 5 hours post induction and the scFv and Fab analysed for binding using ELISA and Biacore against immobilsed antigen E200-300.

Screening methods including SDS-PAGE and N-terminal sequencing were combined with ELISA, Biacore and flow cytometry against cancer cells to determine the biophysical characteristics of the antigen binding site on the control antibody binding domains prior to affinity maturation.

Mutagenesis of the 2F6 scFv was introduced through a combination of error prone PCR, NNK randomisation and sequence length variation of HCDR3. A mutated library in the phagemid vector was of order 1×10$^7$. Screening of the library for higher affinity mutants employed a combination of phage display with filter expression assays using biotinylated E200-300 antigen. A selection of higher affinity scFv lead phage clones underwent small scale expression of soluble antibody fragments with affinities measured using ELISA and Biacore.

Results:

The HCDR3 sequences of scFv/Fab derivatives obtained from the affinity maturation that showed enhanced binding over the 2F6 are shown in FIG. 17.

Figure 18:
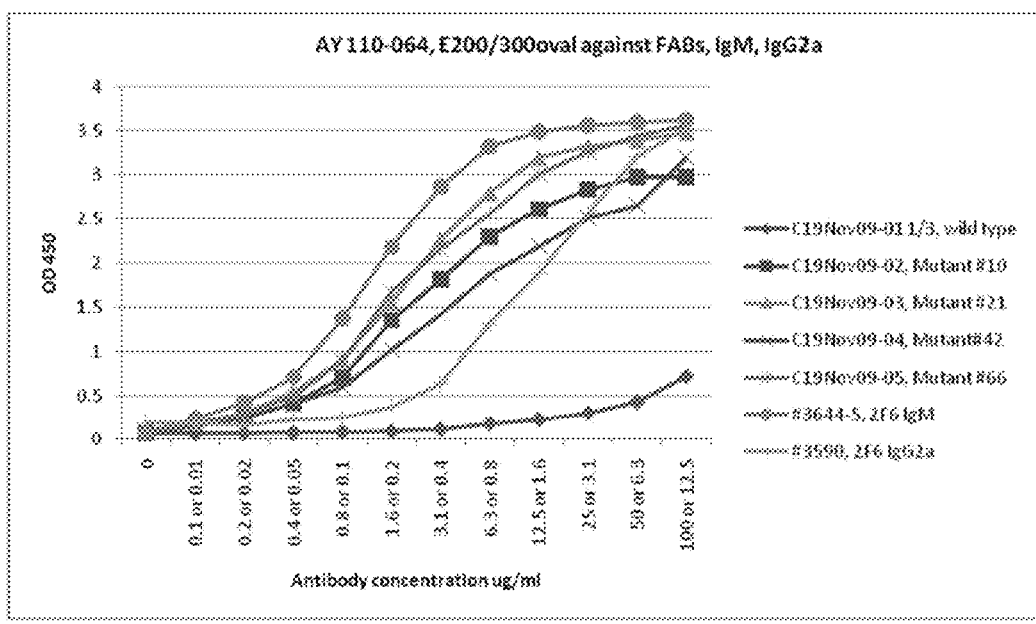
FIG. 18. ELISA of IgM, IgG2a and Fab Leads. Lead Affinity Matured 2F6-Derived Fab ELISA (scale 0.01-12.5 ug/mL for IgM and IgG2a, 0.1-100 ug/mL for Fabs). The $EC_{50}$ values for the original IgM and the recombinant $IgG_{2a}$ were measured to be 0.14 and 1.6 ug/mL respectively. The WT Fab exhibited a very low $EC_{50}$ while the lead affinity matured Fab species selected from ScFv screening (#10, #21, #42 and #66) bound much more tightly with an $EC_{50}$ in the range 2-4 ug/mL or about 125 times stronger than WT, matching the affinity of the fully formed $IgG_{2a}$ antibody.

Binding constants are shown in the ELISA and summary table in FIG. 18. The multi-valent IgM has a higher EC$_{50}$ than the IgG format to the epitope target. The 2F6 recombinant Fab exhibits much lower (2-logs) binding than the selected affinity matured leads.

Conclusion:

Murine antigen binding sites were produced such that in an Fab format the affinity relative to the recombinant 2F6 monoclonal antibody was improved.

Example 6

Biochemical Characterisation of Affinity Matured Fabs

Objective:

To determine whether the affinity matured Fabs exhibited specificity for non-functional $P2X_7$ receptors expressed on live cells.

Background:

The parent 2F6 antibody forms IgM and IgG2a only bound non-functional $P2X_7$ receptors expressed on live cells with high affinity, not monomeric $P2X_7$ receptors nor functional $P2X_7$ receptors. Experiments were performed to confirm that this specificity was not lost during affinity maturation.

Materials and Methods:

Flow cytometry was used to measure the enhanced binding of selected affinity matured recombinant Fabs in human COLO-205 and PC3 cell lines over that of the starting 2F6 sequence. Recombinant FLAG-tagged Fabs were bound to cells and detected using a Sigma F4049 murine monoclonal anti-FLAG antibody conjugated to FITC used at a concentration of 1:75. Affinity purified sheep 200-300 antibody was examined for direct comparison with the 2F6 mIgG2a WT by Flow to PC3 cells.

Figure 19A:
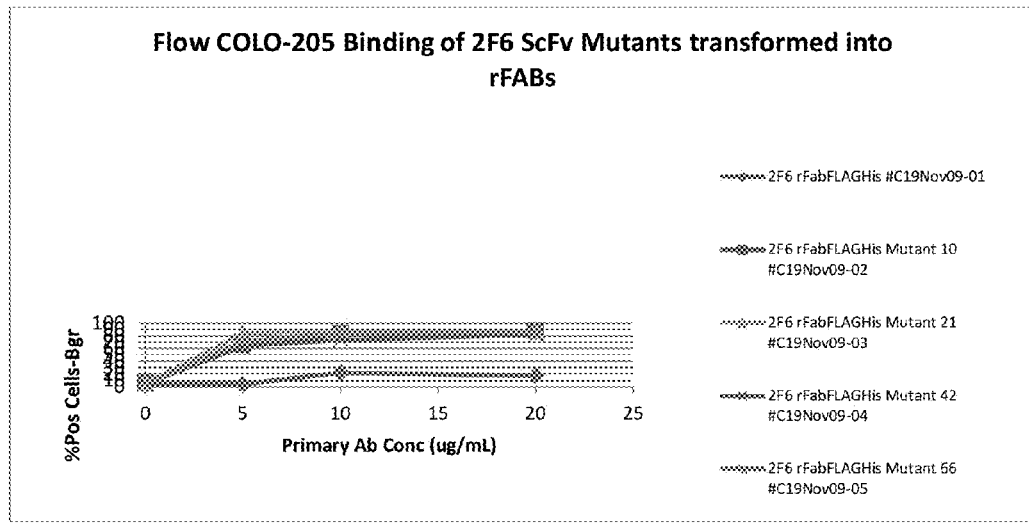
FIGS. 19A-B. (A) Flow cytometry results for binding recombinant Fabs to live colorectal COLO205 tumour cells. A Sigma anti-FLAG secondary antibody (#F4049) was used to detect the binding of the primary antibodies. WT 2F6 Fab bound weakly over the same concentration range. The EC50 for the four lead Fabs is very similar to the values obtained from ELISA measurements. (B) Very similar improved binding results were obtained for prostate PC3 cells.
Figure 19B:
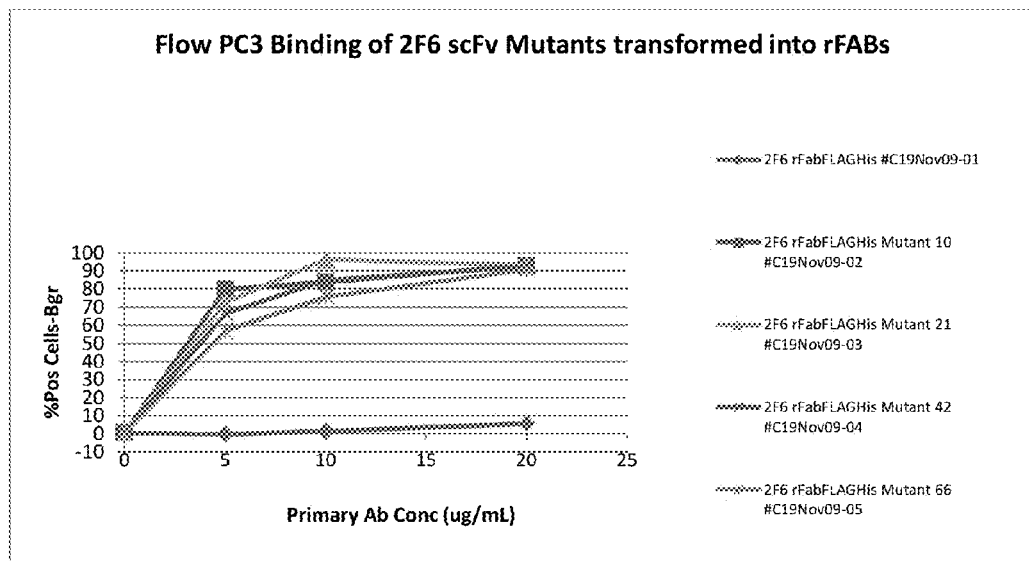
Figure 20:
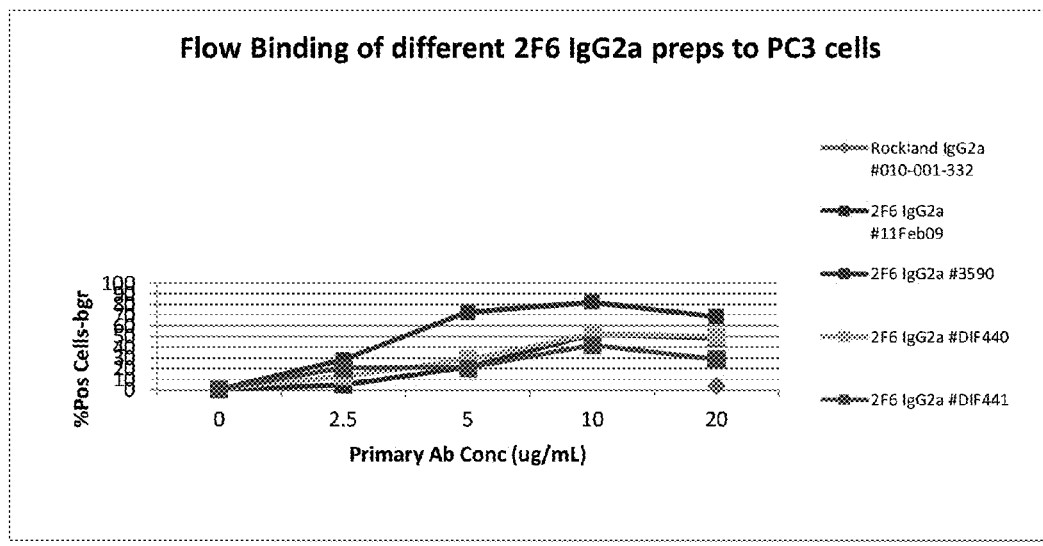
FIG. 20. A comparison was made with various preparations of recombinant 2F6 $IgG_{2a}$ to determine the relative binding strength of the WT formatted antibody to PC3 cells compared with the affinity matured Fabs. Rockland $IgG_{2a}$ #010-001-332 was used for control to determine background (diamond). Binding of the fully formatted WT antibody was comparable to the binding elicited by the lead Fabs.
Figure 21:
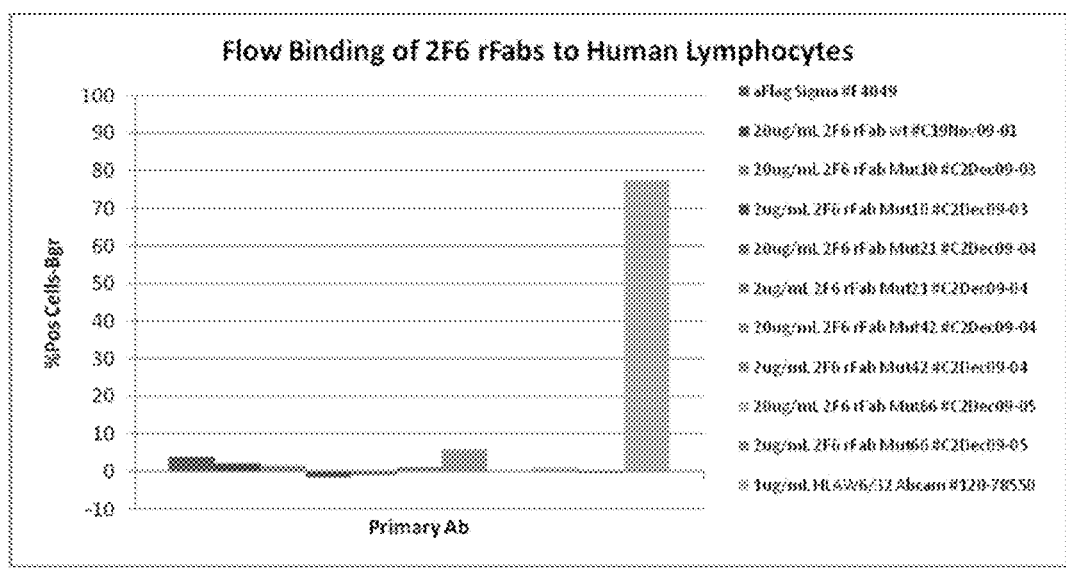
FIG. 21. Verification of the lack of binding to functional $P2X_7$ receptor on human lymphocytes by the lead Fabs was determined by flow cytometry. Sigma anti-FLAG antibody #F4049 was used as the secondary. Abcam HLA antibody was used as a control. No binding was detected above background as determined by the secondary only signal in the left hand column. The order or primary antibody from left to right along the x-axis is the same as the order of the legend from top to bottom.
Figure 22:
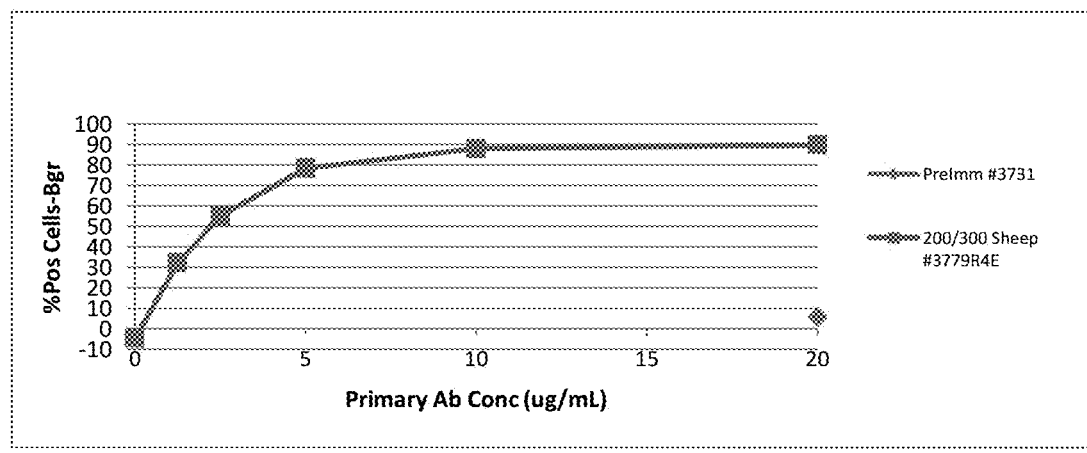
FIG. 22. Flow cytometry results for binding high affinity purified sheep polyclonal antibody to PC3 cells showing significantly stronger binding than WT 2F6 hIgG2a and indicates the improvements to be expected from a range of affinity matured Fabs once converted to divalent IgG binders.

Results:

Fabs bound selectively to non-functional receptors on live cells COLO-205 cells (FIG. 19A) and PC3 cells (FIG. 19B) with higher affinity than the 2F6 WT Fab. Similar affinities were observed using various 2F6 mIgG2a format preps further showing enhanced affinity over the WT sequence (FIG. 20). In contrast, when these same recombinant affinity purified Fabs were tested against human lymphocytes expressing functional $P2X_7$ receptors, negligible binding occurred. A positive HLA control was added (FIG. 21). In comparison with WT 2F6 mIgG2a, binding to PC3 cells by Flow using the affinity purified sheep polyclonal E200-300 showed much higher binding (FIG. 22), in line with the expected improvements from affinity maturation.

Conclusion:

High affinity, selective Fabs and scFvs have been generated which are useful for diagnostic and therapeutic purposes, in line with the level obtained from a polyclonal sheep antiserum titre that has itself exhibited significant therapeutic efficacy as shown in mouse xenograft studies.

It will be understood that the invention disclosed and defined in this specification extends to all alternative combinations of two or more of the individual features mentioned or evident from the text or drawings. All of these different combinations constitute various alternative aspects of the invention.

---

The invention claimed is:

1. An antigen binding site for binding to a P2X₇ receptor, the antigen binding site being defined by a general formula comprising:

FR1-CDR1-FR2-CDR2-FR3-CDR3-FR4-linker-FR1a-CDR1a-FR2a-CDR2a-FR3a-CDR3a-FR4a wherein:

FR1, FR2, FR3, FR4, FR1a, FR2a, FR3a and FR4a are each framework regions;

CDR1, CDR2, CDR3, CDR1a, CDR2a, CDR3a are each complementarity determining regions;

wherein:
CDR1 has an amino acid sequence of KASQNVGTNVA (SEQ ID NO: 5)
CDR2 has an amino acid sequence of SASFRYS (SEQ ID NO: 6)
CDR3 has an amino acid sequence of QQYNSYPFT (SEQ ID NO: 33)
CDR1a has an amino acid sequence of SYYMS (SEQ ID NO: 23)
CDR2a has an amino acid sequence of AINSNGGSTYYPDTVKG (SEQ ID NO: 24)
CDR3a has an amino acid sequence selected from the group consisting of HYSSRFFDV (SEQ ID NO: 34), NFKLMYYNV (SEQ ID NO: 13), NYRGDYYET (SEQ ID NO: 8), NFLESYFEA (SEQ ID NO: 7), NYLPMYYEV (SEQ ID NO: 12), HYIKVYYEA (SEQ ID NO: 15), HYSSRFFEV (SEQ ID NO: 16), NFRVMFFKA (SEQ ID NO: 17), HFQRGYYNI (SEQ ID NO: 10), YHVIQYLGP (SEQ ID NO: 19), HYSKEYYNI (SEQ ID NO: 9), YFPLVYYDV (SEQ ID NO: 11), DFTVPFYNA (SEQ ID NO: 20), NYDKKYFDV (SEQ ID NO: 21).

2. The antigen binding site according to claim 1, wherein:
FR1 has an amino acid sequence of MADIVMTQSQKFMSTSVGDRVSVTC (SEQ ID NO: 25);
FR2 has an amino acid sequence of WYQQKPGQSPKALIY(SEQ ID NO: 26);
FR3 has an amino acid sequence of GVPDRFTGSGSGTDFTLTISNVQSEDLAEFFC (SEQ ID NO: 27); and
FR4 has an amino acid sequence of FGSGTRLEIK (SEQ ID NO: 28).

3. The antigen binding site according to claim 1, wherein:
FR1a has an amino acid sequence of: DVKLVESGGGLVKLGGSLKLSCAASGFTFS (SEQ ID NO: 29);
FR2a has an amino acid sequence of: WVRQTPEKRLELVA (SEQ ID NO: 30);
FR3a has an amino acid sequence of: RFTISRDNAKNTLYLQMSSLKSEDTAFYYCTR (SEQ ID NO: 31); and
FR4a has an amino acid sequence of: WGAGTTVTVSS (SEQ ID NO: 32).

4. The antigen binding site according to claim 1, wherein the linker has an amino acid sequence of 15 amino acid residues.

5. The antigen binding site according to claim 4, wherein the linker has the amino acid sequence GGGGSGGGGSGGGGS (SEQ ID NO: 47).

6. The antigen binding site of claim 1, wherein the antigen binding site comprises a kappa light chain.

7. The antigen binding site of claim 1, wherein the antigen binding site comprises a lambda light chain.

8. The antigen binding site of claim 1, wherein the antigen binding site it selected from the group consisting of Fab, dAb, scFv, diabody and triabody.

9. The antigen binding site of claim 1, wherein the antigen binding site is selected from the group consisting of a monoclonal antibody, a humanised antibody, and a recombinant antibody.

10. The antigen binding site of claim 9, wherein the antibody is IgG1 isotype.

11. The antigen binding site of claim 10, wherein the antibody is bivalent or bispecific.

12. A method for the diagnosis of cancer associated with expression of non-functional $P2X_7$ receptor, including the step of contacting tissues or cells for which the presence or absence of cancer is to be determined with a reagent in the form of an antigen binding site according to claim 1; wherein the detection of the binding of the reagent is indicative of a diagnosis of cancer.

13. A method of treating a cancer associated with expression of a non-functional $P2X_7$ receptor comprising administering an effective amount of an antigen binding site according to claim 1.

* * * * *